(12) United States Patent
He et al.

(10) Patent No.: US 12,404,331 B2
(45) Date of Patent: Sep. 2, 2025

(54) ANTI-PD-1 ANTIBODIES AND USES THEREOF

(71) Applicants: TCRCURE BIOPHARMA CORP., Chapel Hill, NC (US); GUANGDONG TCRCURE BIOPHARMA TECHNOLOGY CO., LTD., Guangzhou (CN)

(72) Inventors: Wei-Wu He, Sugarland, TX (US); Paul Bryson, Alhambra, CA (US); Si Li, Alhambra, CA (US); Donghui Ma, North Potomac, MD (US)

(73) Assignees: TCRCURE BIOPHARMA CORP.; GUANGDONG TCRCURE BIOPHARMA TECHNOLOGY CO., LTD., Guangzhou (CN)

( * ) Notice: Subject to any disclaimer, the term of this patent is extended or adjusted under 35 U.S.C. 154(b) by 899 days.

(21) Appl. No.: 17/604,555

(22) PCT Filed: Apr. 17, 2020

(86) PCT No.: PCT/US2020/028773
§ 371 (c)(1),
(2) Date: Oct. 18, 2021

(87) PCT Pub. No.: WO2020/214957
PCT Pub. Date: Oct. 22, 2020

(65) Prior Publication Data
US 2022/0195047 A1   Jun. 23, 2022

Related U.S. Application Data

(60) Provisional application No. 62/836,177, filed on Apr. 19, 2019.

(51) Int. Cl.
*C07K 16/28* (2006.01)
*A61K 39/39* (2006.01)
*A61K 45/06* (2006.01)
*A61K 47/68* (2017.01)

(52) U.S. Cl.
CPC .......... *C07K 16/2818* (2013.01); *A61K 39/39* (2013.01); *A61K 45/06* (2013.01); *A61K 47/6849* (2017.08); *C07K 2317/24* (2013.01); *C07K 2317/565* (2013.01); *C07K 2317/622* (2013.01); *C07K 2317/73* (2013.01); *C07K 2317/92* (2013.01)

(58) Field of Classification Search
CPC ........... C07K 16/2818; C07K 2317/24; C07K 2317/565; C07K 2317/622; C07K 2317/73; C07K 2317/92; A61K 39/39; A61K 45/06; A61K 47/6849; A61P 35/00; A61P 35/02
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | DeCant et al. | |
| 4,447,233 A | 5/1984 | Mayfield | |
| 4,486,194 A | 12/1984 | Ferrara | |
| 4,487,603 A | 12/1984 | Harris | |
| 4,522,811 A | 6/1985 | Eppstein et al. | |
| 4,596,556 A | 6/1986 | Morrow et al. | |
| 4,676,980 A | 6/1987 | Segal et al. | |
| 4,690,915 A | 9/1987 | Rosenberg | |
| 4,790,824 A | 12/1988 | Morrow et al. | |
| 4,941,880 A | 7/1990 | Burns | |
| 5,064,413 A | 11/1991 | McKinnon et al. | |
| 5,087,616 A | 2/1992 | Myers et al. | |
| 5,225,539 A | 7/1993 | Winter | |
| 5,312,335 A | 5/1994 | McKinnon et al. | |
| 5,374,548 A | 12/1994 | Caras | |
| 5,383,851 A | 1/1995 | McKinnon et al. | |
| 5,399,163 A | 3/1995 | Peterson et al. | |
| 5,399,331 A | 3/1995 | Loughrey et al. | |
| 5,416,016 A | 5/1995 | Low et al. | |
| 5,530,101 A | 6/1996 | Queen et al. | |
| 5,585,089 A | 12/1996 | Queen et al. | |

(Continued)

FOREIGN PATENT DOCUMENTS

| CN | 101213297 | 7/2008 |
|---|---|---|
| CN | 105777906 | 7/2016 |

(Continued)

OTHER PUBLICATIONS

US 8,252,592 B2, 08/2012, Sadelain et al. (withdrawn)

(Continued)

*Primary Examiner* — Julie Wu
*Assistant Examiner* — Bryan William Heck
(74) *Attorney, Agent, or Firm* — Fish & Richardson P.C.

(57) ABSTRACT

This disclosure relates to isolated monoclonal antibodies or antigen-binding fragments thereof that specifically bind to PD-1 and block the interaction between PD-1 and PD-L1/PD-L2. The disclosure also relates to antibodies that are chimeric, humanized, bispecific, derivatized, single chain antibodies, portions of fusion proteins or bispecific antibodies. Nucleic acid molecules encoding the antibodies, hybridomas, and methods for expressing antibodies are also provided. Pharmaceutical compositions comprising the antibodies are also provided. This disclosure also provides use of these antibodies to enhance T-cell function and upregulate cell-mediated immune responses for the treatment and prevention of various diseases.

28 Claims, 24 Drawing Sheets

Specification includes a Sequence Listing.

(56) References Cited

U.S. PATENT DOCUMENTS

| | | |
|---|---|---|
| 5,641,870 A | 6/1997 | Rinderknecht et al. |
| 5,693,762 A | 12/1997 | Queen et al. |
| 5,811,097 A | 9/1998 | Allison et al. |
| 5,837,243 A | 11/1998 | Deo et al. |
| 5,877,293 A | 3/1999 | Adair et al. |
| 5,886,152 A | 3/1999 | Nakatani et al. |
| 5,922,845 A | 7/1999 | Deo et al. |
| 6,054,297 A | 4/2000 | Carter et al. |
| 6,180,370 B1 | 1/2001 | Queen et al. |
| 6,451,995 B1 | 9/2002 | Cheung et al. |
| 7,446,190 B2 | 11/2008 | Sadelain et al. |
| 7,569,664 B2 | 8/2009 | Karsten et al. |
| 8,728,474 B2 | 5/2014 | Honjo et al. |
| 9,642,906 B2 | 5/2017 | Ramos et al. |
| 9,834,606 B2 | 12/2017 | Li et al. |
| 10,174,098 B2 | 1/2019 | Hinrichs et al. |
| 11,072,658 B2 * | 7/2021 | Fayadat-Dilman ............ C07K 16/2818 |
| 2002/0131960 A1 | 9/2002 | Sadelain et al. |
| 2003/0064477 A1 | 4/2003 | Band et al. |
| 2003/0170238 A1 | 9/2003 | Gruenberg et al. |
| 2011/0256154 A1 | 10/2011 | Vincent et al. |
| 2013/0149337 A1 | 6/2013 | Cooper et al. |
| 2013/0287748 A1 | 10/2013 | June |
| 2017/0044259 A1 | 2/2017 | Tipton et al. |
| 2017/0247454 A1 | 8/2017 | Benz et al. |
| 2018/0030137 A1 | 2/2018 | Eenennaam et al. |
| 2018/0185482 A1 | 7/2018 | Sheng et al. |
| 2018/0208896 A1 | 7/2018 | Poirot et al. |
| 2020/0046769 A1 | 2/2020 | Wang |
| 2023/0077100 A1 | 3/2023 | Zhao et al. |

FOREIGN PATENT DOCUMENTS

| | | |
|---|---|---|
| CN | 107043420 | 8/2017 |
| CN | 107249605 | 10/2017 |
| CN | 107325180 | 11/2017 |
| CN | 107881185 | 4/2018 |
| CN | 108135998 | 6/2018 |
| CN | 110139873 | 8/2019 |
| CN | 110423757 | 11/2019 |
| CN | 110511960 | 11/2019 |
| EP | 404097 | 12/1990 |
| IN | 340060 | 7/2020 |
| WO | WO 1993/011161 | 6/1993 |
| WO | WO 1996/013593 | 5/1996 |
| WO | WO 1996/018105 | 6/1996 |
| WO | WO 1996/027011 | 9/1996 |
| WO | WO 1999/018129 | 4/1999 |
| WO | WO 2004/033685 | 4/2004 |
| WO | WO 2004/076646 | 9/2004 |
| WO | WO 2006/037960 | 4/2006 |
| WO | WO 2008/077546 | 7/2008 |
| WO | WO 2008/156712 | 12/2008 |
| WO | WO 2009/114335 | 9/2009 |
| WO | WO 2010/029434 | 3/2010 |
| WO | WO 2011/044186 | 4/2011 |
| WO | WO 2014/134165 | 9/2014 |
| WO | WO 2014/140904 | 9/2014 |
| WO | WO 2016/115274 | 7/2016 |
| WO | WO 2016/081518 | 8/2016 |
| WO | WO 2016/126608 | 8/2016 |
| WO | WO 2016/196388 | 12/2016 |
| WO | WO 2017/149515 | 9/2017 |
| WO | WO 2018/067618 | 4/2018 |
| WO | WO 2018/195348 | 10/2018 |
| WO | WO 2018/197492 | 11/2018 |
| WO | WO 2019/079777 | 4/2019 |
| WO | WO 2019/195486 | 10/2019 |

OTHER PUBLICATIONS

Kwok, Gerry, et al. "Pembrolizumab (keytruda)." Human vaccines & immunotherapeutics 12.11 (2016): 2777-2789. (Year: 2016).*

Kiyoshi, Masato, et al. "Affinity improvement of a therapeutic antibody by structure-based computational design: generation of electrostatic interactions in the transition state stabilizes the antibody-antigen complex." PloS one 9.1 (2014): e87099. (Year: 2014).*

Rudikoff, Stuart, et al. "Single amino acid substitution altering antigen-binding specificity." Proceedings of the National Academy of Sciences 79.6 (1982): 1979-1983. (Year: 1982).*

Sela-Culang, Inbal, Vered Kunik, and Yanay Ofran. "The structural basis of antibody-antigen recognition." Frontiers in immunology 4 (2013): 302. (Year: 2013).*

[No Author Listed] [online], "NCT02280811 T Cell Receptor Immunotherapy Targeting HPV-16 E6 for HPV-Associated Cancers," clinicaltrials.gov, 2017, retrieved from URL <https://clinicaltrials.gov/ct2/show/NCT02280811>, 12 pages.

Iwamura et al., "siRNA-mediated silencing of PD-1 ligands enhances tumor-specific human T-cell effector functions," Gene Therapy, 2012, 19:959-966.

Jin et al., "Engineered T cells targeting E7 mediate regression of human papillonnavirus cancers in a murine model," JCI Insight, 2018, 3(8):e99488, 12 pages.

Li et al., "Enhanced Cancer Immunotherapy by Chimeric Antigen Receptor—Modified T Cells Engineered to Secrete Checkpoint Inhibitors," Clin Cancer Res, 2017, 23(22):6982-6992.

Rafiq et al., "Enhancing CAR T Cell Anti-Tumor Efficacy through Secreted Single Chain Variable Fragment (scFv) Immune Checkpoint Blockade," Blood, 2017, 130(Suppl 1): 842, 3 pages.

Ramos et al., "Human Papillomavirus Type 16 E6/E7-Specific Cytotoxic T Lymphocytes for Adoptive Immunotherapy of HPV-Associated Malignancies," J Immunother., Jan. 2013, 36(1):66-76, 21 pages.

Rice et al., "An HPV-E6/E7 immunotherapy plus PD-1 checkpoint inhibition results in tumor regression and reduction in PD-L1 expression," Cancer Gene Therapy, 2015, 22:454-462.

Suarez et al., "Chimeric antigen receptor T cells secreting anti-PD-L1 antibodies more effectively regress renal cell carcinoma in a humanized mouse model," Oncotarget, 2016, 7(23):34341-34355.

Yeku et al. "Armored CAR T cells enhance antitumor efficacy and overcome the tumor microenvironment," Scientific reports, 2017, 7(1):1-14.

Doran et al., "T-cell receptor gene therapy for human papillomavirus—associated epithelial cancers: a first-in-human, phase I/II study," Journal of Clinical Oncology, Oct. 2019, 37(30):2759-2768.

International Preliminary Report on Patentability in International Appln. No. PCT/CN2021/075388, mailed on Jul. 28, 2022, 6 pages.

International Search Report and Written Opinion in International Appln. No. PCT/CN2020/074366, mailed on Nov. 9, 2020, 14 pages.

International Search Report and Written Opinion in International Appln. No. PCT/CN2021/075388, mailed on May 6, 2021, 10 pages.

Liu et al., "Combination immune checkpoint blockade strategies to maximize immune response in gynecological cancers," Current Oncology Reports, Dec. 2018, 20(12):1-11.

Nakagawa et al., "HLA class I binding promiscuity of the CD8 T-cell epitopes of human papillomavirus type 16 E6 protein," Journal of Virology, Nov. 2006, 81(3):1412-1423.

International Preliminary Report on Patentability in International Appln. No. PCT/CN2020/074366, mailed on Aug. 18, 2022, 7 pages.

Topalian et al., "Safety, Activity, and Immune Correlates of Anti-PD-1 Antibody in Cancer," The New England Journal of Medicine, Jun. 28, 2012, 366(26):2443-2454.

Wang et al., "Study on Preparation and Biological Function of Chicken PD-1 Monoclonal Antibody," China Animal Husbandry & Veterinary Medicine, Dec. 7, 2018, 45(12):3363-3370 (English Abstract).

Abhinandan et al., "Analysis and improvements to Kabat and structurally correct numbering of antibody variable domains," Molecular Immunology, Aug. 2008, 45(14):3832-3839.

Agata et al., "Expression of the PD-1 antigen on the surface of stimulated mouse T and B lymphocytes," Int. Immunol., May 1, 1996, 8(5):765-772.

(56) References Cited

OTHER PUBLICATIONS

Bansal et al., "Human papillomavirus-associated cancers: A growing globalproblem," International Journal of Applied and Basic Medical Research, 2016, 6(2):84-89.
Bennett et al., "Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses," J. Immunol., Jan. 15, 2003, 170(2):711-718.
Berge et al., "Pharmaceutical Salts," J. Pharm. Sci., Jan. 1977, 66(1):1-19.
Bernard et al., "Proteasomal degradation of p53 by human papillomavirus E6 oncoproteinrelies on the structural integrity of p53 core 5 domain," PloS one, 2011, 6(10):e25981, 10 pages.
Bird et al., "Single-Chain Antigen-Binding Proteins," Science, Oct. 21, 1988, 242(4877):423-426.
Blank et al., "Interaction of PD-L1 on tumor cells with PD-1 on tumor-specific T cells as a mechanism of immune evasion: implications for tumor immunotherapy," Cancer Immunol. Immunother., 2005, 54:307-314.
Bloeman et al., "Adhesion molecules: a new target for immunoliposome-mediated drug delivery," FEBS Lett., Jan. 3, 1995, 357(2):140-144.
Brennan et al., "Preparation of Bispecific Antibodies by Chemical Recombination of Monoclonal Immunoglobulin G1 Fragments," Science, Jul. 5, 1985, 229(4708):81-83.
Brianti et al., "Review of HPV-related diseases and cancers," New Microbiologica, 2017, 40(2):80-85.
Brown et al., "Blockade of Programmed Death-1 Ligands on Dendritic Cells Enhances T Cell Activation and Cytokine Production," J. Immunol., Feb. 1, 2003, 170(3):1257-1266.
Carter et al., "PD-1:PD-L inhibitory pathway affects both CD4+ and CD8+ T cells and is overcome by IL-2," Eur. J. Immunol., Feb. 12, 2002, 32(3):634-643.
Castellsague, "Natural History And Epidemiology of Hpv Infection and Cervical Cancer," Gynecologic Oncology, 2008, 110:S4-S7.
Chan et al., "Human Papillomavirus Infection and Cervical Cancer: Epidemiology, Screening, and Vaccination—Review of Current Perspectives," Journal of Oncology, 2019, 3257939:1-11.
Chothia et al., "Conformations of immunoglobulin hypervariable regions," Nature, Dec. 28, 1989, 342(6252):877-883.
Cox et al., "A Directory of Human Germ-line VH Segments Reveals a Strong Bias in their Usage," Eur. J. Immunol., Apr. 1994, 24(4):827-836.
Creelan, "Update on immune checkpoint inhibitors in lung cancer," Cancer Control, Jan. 1, 2014, 21(1):80-89.
Davila et al., "CD19 CAR-targeted T cells induce long20term remission and B Cell Aplasia in an immunocompetent mouse model of B cell acutelymphoblastic leukemia," PloS one, Apr. 9, 2013, 8(4):e61338, 14 pages.
Dong et al., "B7-H1 pathway and its role in the evasion of tumor immunity," J. Mol. Med., Apr. 30, 2003, 81:281-287.
Dong et al., "Tumor-associated B7-H1 promotes T-cell apoptosis: A potential mechanism of immune evasion," Nat. Med., Jun. 24, 2002, 8:793-800.
Dranoff et al., "Vaccination with irradiated tumor cells engineered to secrete murine granulocyte-macrophage colony-stimulating factor stimulates potent, specific, and long-lasting anti-tumor immunity," Proc. Natl. Acad. Sci. USA, Apr. 15, 1993, 90:3539-3543.
Draper et al., "Targeting of HPV-16+ Epithelial Cancer Cells by TCR Gene Engineered T Cells Directed against E6," Clinical Cancer Research, 2015, 21(19):4431-4443.
Estep et al. "High throughput solution-based measurement of antibody-antigen affinity and epitope binning," mAbs, Mar. 1, 2013, 5(2):270-278.
Freeman et al., "Engagement of the PD-1 Immunoinhibitory Receptor by a Novel B7 Family Member Leads to Negative Regulation of Lymphocyte Activation," J. Exp. Med., Oct. 2, 2000, 192(7):1027-1034.
Freeman et al., "Protect the killer: CTLs need defenses against the tumor," Nat. Med., Aug. 1, 2002, 8:787-789.

GenBank Accession No. AJ406678, "Homo sapiens partial VH 3-23 gene for rearranged immunoglobulin heavy chain variable region, isolate case3-Ki67--555," dated Jul. 14, 2016, 2 pages.
GenBank Accession No. BC070333.1, "Homo sapiens immunoglobulin heavy variable 1-69, mRNA (cDNA clone Image:6557369)," dated Mar. 24, 2009, 2 pages.
GenBank Accession No. NP_001107830.1, "Programmed cell death protein 1," dated Nov. 13, 2017, 3 pages.
GenBank Accession No. NP_001271065.1, "Programmed cell death protein 1," dated Apr. 24, 2016, 1 page.
GenBank Accession No. NP_032824.1, "Programmed cell death protein 1 precursor [Mus musculus]," dated Apr. 5, 2018, 3 pages.
GenBank Accession No. NT_024637, "Homo sapiens chromosome 14 working draft sequence segment, complete sequence," dated Nov. 16, 2000, 2 pages.
Ghetie et al., "Homodimerization of tumor-reactive monoclonal antibodies markedly increases their ability to induce growth arrest or apoptosis of tumor cells," Proc. Natl. Acad. Sci. USA, Jul. 8, 1997, 94(14):7509-7514.
Greenberg et al., "Deficient Cellular Immunity—Finding and Fixing the Defects," Science, Jul. 23, 1999, 285:546-551.
Hahne et al., "Melanoma Cell Expression of Fas(Apo-1/CD95) Ligand: Implications for Tumor Immune Escape," Science, Nov. 22, 1996, 274(5291):1363-1366.
He et al., "Blocking Programmed Death-1 Ligand-PD-1 Interactions by Local Gene Therapy Results in Enhancement of Antitumor Effect of Secondary Lymphoid Tissue Chemokine," J. Immunol., Oct. 15, 2004, 173(8):4919-4928.
Hermans et al., "The Vital assay: a versatile fluorometric technique for assessing CTL-and NKT-mediated cytotoxicity against multiple targets in vitro and in vivo," Journal of Immunological Methods, Feb. 2004, 285(1):25-40.
Hirano et al., "Blockade of B7-H1 and PD-1 by monoclonal antibodies potentiates cancer therapeutic immunity," Cancer Research, Feb. 2005, 65(3):1089-1096.
Holliger et al., ""Diabodies": small bivalent and bispecific antibody fragments," Proc. Natl. Acad. Sci. USA, Jul. 15, 1993, 90(14):6444-6448.
Howard et al., "Biological properties of interleukin 10," Immunology Today, Jun. 1, 1992, 13(6):198-200.
Huston et al., "Protein engineering of antibody binding sites: recovery of specific activity in an anti-digoxin single-chain Fv analogue produced in Escherichia coli," Proc. Natl. Acad. Sci. USA, 1988, 85(16):5879-5883.
Hutloff et al., "ICOS is an inducible T-cell co-stimulator structurally and functionally related to CD28," Nature, Jan. 21, 1999, 397:263-266.
International Preliminary Report in International Appln. No. PCT/US2019/46076, mail dated Feb. 25, 2021, 10 pages.
International Preliminary Report on Patentability in International Appln. No. PCT/US2020/028773, dated Sep. 28, 2021, 8 pages.
International Search Report and Written Opinion in International Appln. No. PCT/US2019/46076, dated Dec. 23, 2019, 17 pages.
International Search Report and Written Opinion in International Appln. No. PCT/US2020/028773, dated Sep. 29, 2020, 14 pages.
Irani et al., "Molecular properties of human IgG subclasses and their implications for designing therapeutic monoclonal antibodies against infectious diseases," Molecular Immunology, Oct. 2015, 67(2):171-182.
Ito et al., "Effective Priming of Cytotoxic T Lymphocyte Precursors by Subcutaneous Administration of Peptide Antigens in Liposomes Accompanied by Anti-CD40 and Anti-CTLA-4 Antibodies," Immunobiology, Apr. 2000, 201(5):527-540.
Iwai et al., "Involvement of PD-L1 on tumor cells in the escape from host immune system and tumor immunotherapy by PD-L1 blockade," Proc. Natl. Acad. Sci. USA, Sep. 17, 2002, 99(19):12293-12297.
Iwai et al., "PD-1 blockade inhibits hematogenous spread of poorly immunogenic tumor cells by enhanced recruitment of effector T cells," Int. Immunol., Feb. 2005, 17(2):133-144.
Jones et al., "Replacing the complementarity-determining regions in a human antibody with those from a mouse," Nature, May 29, 1986, 321:522-525.

(56) References Cited

OTHER PUBLICATIONS

Jones et al., "The INNs and outs of antibody nonproprietary names," mAbs, 2016, 8(1):1-9.
Kehrl et al., "Production of transforming growth factor beta by human T lymphocytes and its potential role in the regulation of T cell growth," J. Exp. Med., May 1, 1986, 163(5):1037-1050.
Keinanen et al., "Biosynthetic lipid-tagging of antibodies," FEBS Lett., Jun. 6, 1994, 346:123-126.
Killion et al., "Systemic Targeting of Liposome-Encapsulated Immunomodulators to Macrophages for Treatment of Cancer Metastasis," Immunomethods, Jun. 1994, 4(3):273-279.
Knudson et al., "M7824, a novel bifunctional anti-PD-L1/TGFβ Trap fusion protein, promotes anti-tumor efficacy as monotherapy and in combination with vaccine," Oncoimmunology, 2018, 7(5):e1426519, 15 pages.
Kochenderfer et al., "Construction and pre-clinical evaluation of an anti-CD19 chimeric antigen receptor," Journal of Immunotherapy, 2009, 32(7):689-702, 26 pages.
Kohler et al., "Derivation of specific antibody-producing tissue culture and tumor lines by cell fusion," Eur. J. Immunol. Jul. 1976, 6(7):511-9, 5 pages.
Kohler et al., "Pillars Article: Continuous cultures of fused cells secreting antibody of predefined specificity," Nature, Aug. 7, 1975, 256(5517):495-497.
Konishi et al., "B7-H1 Expression on Non-Small Cell Lung Cancer Cells and Its Relationship with Tumor-Infiltrating Lymphocytes and Their PD-1 Expression," Clin. Cancer Res., Aug. 2004, 10(15):5094-5100.
Kozbor et al., "The production of monoclonal antibodies from human lymphocytes," Immunol. Today, Mar. 1983, 4(3):72-79.
Kwok et al., "Pembrolizumab (Keytruda)," Human Vaccines and Immunotherapeutics, 2016, 12(11):2777-2789.
Latchman et al., "PD-L2 is a second ligand for PD-1 and inhibits T cell activation," Nat. Immunol., Mar. 2001, 2:261-268.
Lefranc et al., "IMGT unique numbering for immunoglobulin and T cell receptor variable domains and Ig superfamily V-like domains," Developmental & Comparative Immunology, Jan. 2003, 27(1):55-77.
Mannarini et al., "Human Papilloma Virus (HPV) In Head and Neck Region: Review of Literature," Acta Otorhinolaryngologica Italica, Jun. 2009, 29(3):119-126.
Martin et al., "Molecular modeling of antibody combining sites," Methods Enzymol., Jan. 1, 1991, 203:121-153.
Martin, "Protein sequence and structure analysis of antibody variable domains," Antibody Engineering, Springer Berlin Heidelberg, 2001, Chapter 31:422-439.
McLaughlin-Drubin et al., "Viruses Associated With Human Cancer," Biochimica et Biophysica Acta., Mar. 2008, 1782(3):127-150.
Melero et al., "Monoclonal antibodies against the 4-1BB T-cell activation molecule eradicate established tumors," Nature Medicine, Jun. 1, 1997, 3:682-685.
Mokyr et al., "Realization of the Therapeutic Potential of CTLA-4 Blockade in Low-Dose Chemotherapy-treated Tumor-bearing Mice," Cancer Research, Dec. 1998, 58(23):5301-5304.
Moore et al., "Antibody cross-competition analysis of the human immunodeficiency virus type 1 gp120 exterior envelope glycoprotein," Journal of Virology, Mar. 1996, 70(3):1863-1872, 13 pages.
Morea et al., "Antibody structure, prediction and redesign," Biophys. Chem., Oct. 1997, 68(1-3):9-16.
Morea et al., "Conformations of the third hypervariable region in the VH domain of immunoglobulins," J. Mol. Biol., Jan. 16, 1998, 275(2):269-294.
Okazaki et al., "New regulatory co-receptors: inducible co-stimulator and PD-1," Curr. Opin. Immunol., Dec. 2002, 14(6):779-782.
Owais et al., "Chloroquine encapsulated in malaria-infected erythrocyte-specific antibody-bearing liposomes effectively controls chloroquine-resistant Plasmodium berghei infections in mice," Antimicrob. Agents Chemother., Jan. 1995, 39(1):180-184.

Ping et al., "T-cell receptor engineered T cells for cancer treatment: current status and future directions," Protein & Cell, 2018, 9(3):254-266.
Poljak, "Production and structure of diabodies," Structure, Dec. 1994, 2(12):1121-1123.
Ponomarenko et al., "Antibody-protein interactions: benchmark datasets and prediction tools evaluation," BMC Structural Biology, Oct. 2, 2007, 7:64, 19 pages.
Queen et al., "A humanized antibody that binds to the interleukin 2 receptor," Proc. Natl. Acad. Sci. USA, Dec. 1, 1989, 86(24):10029-10033.
Raedler, "Keytruda (Pembrolizumab): First PD-1 Inhibitor Approved for Previously Treated Unresectable or Metastatic Melanoma," American Health & Drug Benefits, Mar. 2015, 8:96-100.
Ranade, "Drug Delivery Systems. 1. Site-Specific Drug Delivery Using Liposomes as Carriers," J. Clin. Pharmacol., Aug. 1989, 29:685-694.
Ridge et al., "A conditioned dendritic cell can be a temporal bridge between a CD4+ T-helper and a T-killer cell," Nature, Jun. 4, 1998, 393:474-478.
Riechmann et al., "Reshaping human antibodies for therapy," Nature, Mar. 24, 1998, 332:323-327.
Rosenberg, "Cell transfer immunotherapy for metastatic solid cancer—what clinicians need to know," Nature Reviews Clinical Oncology, Aug. 2, 2011, 8(10):577-585.
Schreier et al., "Targeting of liposomes to cells expressing CD4 using glycosylphosphatidylinositol-anchored gp120. Influence of liposome composition on intracellular trafficking," J. Biol. Chem., Mar. 1994, 269(12):9090-9098.
Silva et al. "The S228P Mutation Prevents in Vivo and in Vitro IgG4 Fab-arm Exchange as Demonstrated using a Combination of Novel Quantitative Immunoassays and Physiological Matrix Preparation," Journal of Biological Chemistry, Feb. 2015, 290(9):5462-5469.
Simon et al., "CAR-T cell therapy in melanoma: A future success story," Experimental Dermatology, Oct. 4, 2018, 27(12):1315-1321.
Songsivilai et al., "Bispecific antibody: a tool for diagnosis and treatment of disease," Clin. Exp. Immunol., Mar. 1990, 79:315-321.
Stanley et al., "HPV: From Infection to Cancer," Biochemical Society Transactions, Nov. 23, 2007, 35(6):1456-1460.
Themeli et al., "Generation of tumor-targeted human T lymphocytes from induced pluripotent stem cells for cancer therapy," Nature Biotechnology, Aug. 11, 2013, 31(10):928-933, 8 pages.
Thomas, "Of ITAMs and ITIMs: turning on and off the B cell antigen receptor," J. Exp. Med., Jun. 1, 1995, 181(6):1953-1956.
Tomlinson et al. "The Repertoire of Human Germline VH Sequences Reveals about Fifty Groups of VH Segments with Different Hypervariable Loops," J. Mol. Biol., Oct. 5, 1992, 227(3):776-798.
Topalian et al., "Safety, Activity, and Immune Correlates of Anti-PD-1 Antibody in Cancer," New England Journal of Medicine, Jun. 28, 2012, 366(26):2443-2454.
Tsukahara et al., "CD 19 target-engineered T-cells accumulate at tumor lesions in human B-cell lymphoma xenograft mouse models," Biochemical and Biophysical Research Communications, 2013, 438(1):84-89.
Umezawa et al., "Liposome targeting to mouse brain: Mannose as a recognition marker," Biochem. Biophys. Res. Commun., Jun. 30, 1988, 153(3):1038-1044.
Vidarsson et al., "IgG subclasses and allotypes: from structure to effector functions," Frontiers in Immunology, Oct. 20, 2014, 5(520):1-17.
Vivier et al., "Immunoreceptor tyrosine-based inhibition motifs," Immunol. Today, Jun. 1997, 18(6):286-291.
Wadhwa et al., "Receptor mediated glycotargeting," Journal of Drug Targeting, 1995, 3(2):111-127.
Ward et al., "Binding activities of a repertoire of single immunoglobulin variable domains secreted from *Escherichia coli*," Nature, Oct. 12, 1989, 341:544-546.
Weinberg et al., "Engagement of the OX-40 Receptor In Vivo Enhances Antitumor Immunity," J. Immunol., Feb. 15, 2000, 164(4):2160-2169.
Wolff et al., "Monoclonal antibody homodimers: enhanced antitumor activity in nude mice," Cancer Research, Jun. 1993, 53(11):2560-2565.

(56) References Cited

OTHER PUBLICATIONS

Wu et al., "An Analysis of the Sequences of the Variable Regions of Bence Jones Proteins and Myeloma Light Chains and their Implications for Antibody Complementarity," J. Exp. Med., Aug. 1, 1970, 132(2):211-250.
Zapata et al., "Engineering linear F(ab')2 fragments for efficient production in *Escherichia coli* and enhanced antiproliferative activity," Protein Eng., Oct. 1, 1995, 8(10):1057-1062.
Zhao et al., "Enhancing tumor targeting and apoptosis using non-covalent antibody homo-dimers," J. Immunol., Sep. 2002, 25(5):396-404.
Zur Hausen et al., "Human Papilloma Viruses," Annu. Rev. Microbiol., 1994, 48:427-447.
EP Search Report in European Appln. No. 19850035.7, dated Jun. 14, 2022, 9 pages.
Tang et al., "Original Article—The advantages of PD1 activating chimeric receptor (PD1-ACR) engineered lymphocytes for PDL1 + cancer therapy," Am J Transl Res, Jan. 1, 2015, pp. 460-473.

\* cited by examiner

F02 light chain variable domain cDNA: (SEQ ID NO: 1)

ATGGAGACAGACACACTCCTGCTATGGGTACTGCTGCTCTGGGTTCCAGGTTCCACTGGTGACACAGTCTCCTGCTTCCTTAGCTGT
ATCTCTGGGGCAGAGGGCCACCATCTCATGCAGGGCCAGCAAAAGTGTCAGTACTTCTGGCTTTAATTATATGCACTGGTACCAGCAGAC
AGCACCTCCAAACTCCTCATCTATCTTGCATCCAACCTAGATTCTGGGGTCCCTGCCAGTTCAGTGGCAGTGGGTCTGGGACAGAGACTTCACCCTCAAC
ATCCATCCCTGTGGAGGAGGATGCTGCAACTCCTGACCTTTCCGCTACACGGTAGCAGTTAACATCTGAGAGGTGCCTCAGTGGTGTGCCTTCTTGAACAACTTCT
ACGGGCTGATGCTGCACCAACTGTATCCATTCTCCCACCATCCAGTGAGCAGTTAACATCTGAGAGGTGCCTCAGTGGTGTGCCTTCTTGAACAACTTCT
ACCCCAAAG

F02 light chain variable domain (Kappa): (SEQ ID NO: 2)

DIVLTQSPASLAVSLGQRATISCRASKSVSTSGFNYMHWYQQKPGQPPKLLIYLASNLDSGVPARFSGSGSGTDFTLNIHPVEEEDAATYYCQHGREL
PLTFGAGTKLELRRADA

F02 heavy chain variable domain cDNA: (SEQ ID NO: 3)

ATGGGATGCAGCTGGGTAATGCTCTTTTTGGTAGCAACAGCTACAGGTGTCCACTCCCAGGTCCAACTGCAGCAGCCTGGGGCTGAACTGGTGAAACC
TGGGGCTTCAGTGAAGTTGTCCTGCAAGGCTTCTGGCTACACCTTCACCAACTACTATTTGTATTGGGTGAAGCAGCAGCCTGGACAAGGCCTTGAGT
GGATTGGGGGATTAATCCTAGCAATGGTGGTACTAACTTCAATGAGAAGTTCAGGGGCAAGGCCACACTGACTGTAGACAAATCCTCAGCACACAGCC
TACATGCAACTCCACTCTGACATCTGAGGACTCTGCCCTCTACTACTGTACAAGAGGACTATAACTACGGGGGCTTTGACTACTGGGGCCA
AGGCTCCACTCTCACAGTCTCCTCAGCCAAAACGACAACCCCATCTGTCTATCCACTGGCCCCTGACAGTCTGAACCTCTGGAATCCTCCCAGCGTGTGCCCTG
TGGGATGCCTGGTCAAGGCTATTTCCCTGAGCCAGTCAGTCTTGAGCCAGTCAGTGCCCTCCAGTGCCCAGACCACCTGGCCACTGCAACCGTGTGCCCACCCGGCCAGCAG
CAGTCTGACCTGACCTGACCCAAGAAAATTGTGCCCAGGATTGTGGGTTGTAA

F02 heavy chain variable domain: (SEQ ID NO: 4)

QQPGAELVKPGASVKLSCRASGYTFTNYYLYWVKQRPGQGLEWIGGINPSNGGTNFNEKFRGKATLTVDKSSSTAYMQLSSLTSEDSAVYFCTRRDYN
YDGGFDYWGQGSTLTVSSAKTT

FIG. 9

Light chain CDR1 of F02: (SEQ ID NO: 5)
RASKSVSTSGFNYMH

Light chain CDR2 of F02: (SEQ ID NO: 6)
LASNLDS

Light chain CDR3 of F02: (SEQ ID NO: 7)
QHGRELPLT

Heavy chain CDR1 of F02: (SEQ ID NO: 8)
GYTFTNY

Heavy chain CDR2 of F02: (SEQ ID NO: 9)
NPSNGG

Heavy chain CDR3 of F02: (SEQ ID NO: 10)
RDYNYDGGFDY

F02 light chain: (SEQ ID NO: 11)
DIVLTQSPASLAVSLGQRATISCRASKSVSTSGFNYMHWYQQKPGQPPKLLIYLASNLDSGVPARFSGSGSGTDFTLNIHPVEEDAATYYCQHGREL
PLTFGAGTKLELRRADAAPTVSIFPPSSEQLTSGGASVVCFLNNFYPKDINV KWKIDGSERQNGVLNSWTDQ DSKDSTYSMS STLTLTKDEY
ERHNSYTCEA THKTSTSPIV KSFNRNEC

F02 heavy chain: (SEQ ID NO: 12)
QQPGAELVKPGASVKLSCRASGYTFTNYYLYWVKQRPGQGLEWIGGINPSNGTNFNEKFRGKATLTVDKSSTAYMQLSSLTSEDSAVYFCTRRDYN
YDGGFDYWGQGSTLTVSSAKTTPPSVYPLAPGSAAQTNSMVTLGCLVKGYFPEPVTVTWNSGSLSSGVHTFPAVLQSDLYTLSSSVTVPSSTWPSETV

FIG. 9 (cont)

TCNVAHPASSTKVDKKIVPRDCGKPCICTVPEVSSVFIFPPKPKDVLTITLTPKVTCVVVDISKDDPEVQFSWFVDDVEVHTAQTKPREEQINSTFR
SVSELPIMHQDWLNGKEFKCRVNSAAFPAPIEKTISKTKGRPKAPQVYTIPPPKEQMAKDKVSLTCMITNFFPEDITVEWQWNGQPAENYKNTQPIMD
TDGSYFVYSKLNVQKSNWEAGNTFTCSVLHEGLHNHHTEKSLSHSPGK

F02 light chain with a signal peptide: (SEQ ID NO: 13)

METDTLLLWVLLLWVPGSTGDIVLTQSPASLAVSLGQRATISCRASKSVSTSGFNYMHWYQQKPGQPPKLLIYLASNLDSGVPARFSGSGSGTDFTLN
IHPVEEEDAATYYCQHGRELPLTFGAGTKLELRRADAAPTVSIFPPSSEQLTSGGASVVCFLNNFYPKDINV KWKIDGSERQNGVLNSWTDQ
DSKDSTYSMS STLTLTKDEY ERHNSYTCEA THKTSTSPIV KSFNRNEC

F02 heavy chain with a signal peptide (SEQ ID NO: 14)

MGCSWVMLFLVATATGVHSQVQLQQPGAELVKPGASVKLSCRASGYTFTNYLYWVKQRPGQGLEWIGGINPSNGGTNFNEKFRGKATLTVDKSSSTA
YMQLSSLTSEDSAVYFCTRRDYNYDGGFDYWGQGSTLTVSSAKTTPPSVYPLAPGSAAQTNSMVTLGCLVKGYFPEPVTVTWNSGSLSSGVHTFPAVL
QSDLYTLSSSVTVPSSTWPSETVTCNVAHPASSTKVDKKIVPRDCGKPCICTVPEVSSVFIFPPKPKDVLTITLTPKVTCVVVDISKDDPEVQFSWF
VDDVEVHTAQTKPREEQINSTFRSVSELPIMHQDWLNGKEFKCRVNSAAFPAPIEKTISKTKGRPKAPQVYTIPPPKEQMAKDKVSLTCMITNFFPED
ITVEWQWNGQPAENYKNTQPIMDTDGSYFVYSKLNVQKSNWEAGNTFTCSVLHEGLHNHHTEKSLSHSPGK

H11 (IgG1) light chain variable domain (Kappa) cDNA: (SEQ ID NO: 15)

GACATCGTCCTTACGCAAAGCCCGGCGACCCTCAGTTTGAGCCCTGGGGAAAGAGCAAGCTGTCTTGTAGAGCATCCAAATCAGTCTCAACTTCTGG
TTTTAATTACATGCACTGGTATCAACAGAAGCCAGGACAAGCACCTAGATTGCTGATCTTCTGGCGTCAAATCTGGCCTCTGGCGTTCCAGCCCGGT
TTAGCGGTTCTGGAAGCGGAACGGACTTTACCTTACCCATATCACTCGAACCAGAGGACTTTGCGATATTACTGCCAACATGGACGGGAGCTG
CCCTTGACGTTTGGTCAAGGAACGAAGTTGGAGATA

H11 light chain variable domain (Kappa): (SEQ ID NO: 16)

DIVLTQSPATLSLSPGERATLSCRASKSVSTSGFNYMHWYQQKPGQAPRLLIFLASNLASGVPARFSGSGSGTDFTLTISSLEPEDFAVYYCQHGREL
PLTFGQGTKLEI

H11 heavy chain variable domain cDNA: (SEQ ID NO: 17)

CAAGTCCAGCTTGTACAAAGCGGTGCCGAAGTGAAAAACCGGGCGCAAGCGTCAAGGTTCATGCAAGGCGAGTGGATACACCTTTACCAACTATTA
CATGTACTGGGGTGCGGCAGCACCCGGCCAGGACTGGAATGATCGGTGGTATTAACCAAGTAATGTGGTACAAATTTCAACGAAAAGTTTAAGA

FIG. 9 (cont)

ACAAAGGACGACGATGACAGTAGACACAAATCTACAAGTACCGCATACATGGAGCTGAGCTCACTGAGATCTGAGGACACCGCAGTCTATTACTGCACACGG
CGAGATTACAATTACGATGGAGGGTTCGACTACTGGGGCCAAGGGACTTTGGTGACTGTATCCTCC

H11 heavy chain variable domain: (SEQ ID NO: 18)

QVQLVQSGAEVKKPGASVKVSCKASGYTFTNYYMYWVRQAPGQGLEWIGGINPSNGGTNFNEKFKNKATMTVDKSTSTAYMELSSLRSEDTAVYYCTR
RDYNYDGGFDYWGQGTLVTVSS

Light chain CDR1 of H11: (SEQ ID NO: 19)

RASKSVSTSGFNYMH

Light chain CDR2 of H11: (SEQ ID NO: 20)

LASNLAS

Light chain CDR3 of H11: (SEQ ID NO: 21)

QHGRELPLT

Heavy chain CDR1 of H11: (SEQ ID NO: 22)

GYTFTNYYMY

Heavy chain CDR2 of H11: (SEQ ID NO: 23)

GINPSNGGTNFNEKFKN

Heavy chain CDR3 of H11: (SEQ ID NO: 24)

RDYNYDGGFDY

H11 light chain: (SEQ ID NO: 25)

FIG. 9 (cont)

DIVLTQSPATLSLSPGERATLSCRASKSVSTSGFNYMHWYQQKPGQAPRLLIFLASNLASGVPARFSGSGSGTDFTLTISSLEPEDFAVYYCQHGREL
PLTFGQGTKLEIRTVAAPSVFIFPPSDEQLKSGTASVVCLLNNFYPREAKVQWKVDNALQSGNSQESVTEQDSKDSTYSLSSTLTLSKADYEKHKVYA
CEVTHQGLSSPVTKSFNRGEC

H11 heavy chain: (SEQ ID NO: 26)

QVQLVQSGAEVKKPGASVKVSCKASGYTFTNYYMYWVRQAPGQGLEWIGGINPSNGGTNFNEKFKNKATMTVDKSTSTAYMELSSLRSEDTAVYYCTR
RDYNYDGGFDYWGQGTLVTVSSASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQKSLSLSPGK

Ab2 (IgG1) light chain variable domain (Kappa) cDNA: (SEQ ID NO: 27)

GATATTCAGATGACACAAAGCCCCTCAAGCCTTAGCGCCATCCGTTGGCGACCGTGTGACCATAACTTGCCGTGCATCAAAAAGCCGTGAGTACCTCTGG
TTTCAATTACATGCACTGGTACCAGCAGACACCTGGAAAAGCTCCAAACTTCTGATCTATCTTGCCTCTAACCTCGATAGTGGTGTACCATCCGCT
TTAGTGGAAGCGAAGTGGGACTGGATTCTCACTATTTCCTTGCAACCTGAAGACATTGCCACCTATTATTGTTTTCACGGCCGCGAACTG
CCCCTTACTTTCGGGCAG GGCACACAAAGTTGCAGATAACAAGG

Ab2 light chain variable domain (Kappa): (SEQ ID NO: 28)

DIQMTQSPSSLSASVGDRVTITCRASKSVSTSGFNYMHWYQQTPGKAPKLLIYLASNLDSGVPS
RFSGSGSGTDFTFTISSLQPEDIATYCFHGRELPLTFGQGTKLQITR

Ab2 heavy chain variable domain cDNA: (SEQ ID NO: 29)

CAGGTACAGCTCCAACAGAGCGGTGCTGAGGTAAAAAAACCAGGTTCAAGTGTTAAAGTCTCATGTAAGGCATCTGGGTACACATTCACAAACTACTA
TCTGTACTGGGTACGCCAGGCTCCAGGTCAGGGCCTTGAGTGGATAGGCGGAATTAACCCTAGTAATGGCGGGACCAACTTCAATGAAAAATTCGTG
GGCGTGTAACTATTACTGCCGACGAGAGTTCAACACCGCATATATGGAGTTGAGTTCTCTTCGTTCAGAGATACTGCTTTCTATTTTTGTACCCGC
CGGGACTACAATTACGATGGGGATTCGACTATTGGGGGCAGGAACCACCGTCACAGTGAGTTCT

Ab2 heavy chain variable domain: (SEQ ID NO: 30)

QVQLQQSGAEVKKPGSSVKVSCKASGYTFTNYYLYWVRQAPGQGLEWIGGINPSNGGTNFNEKFRGRVTITADESSTTAYMELSSLRSEDTAFYFCTR
RDYNYDGGFDYWGQGTTVTVSS

FIG. 9 (cont)

Light chain CDR1 of Ab2: (SEQ ID NO: 31)
RASKSVSTSGFNYMH

Light chain CDR2 of Ab2: (SEQ ID NO: 32)
LASNLDS

Light chain CDR3 of Ab2: (SEQ ID NO: 33)
FHGRELPLT

Heavy chain CDR1 of Ab2: (SEQ ID NO: 34)
GYTFTNYYLY

Heavy chain CDR2 of Ab2: (SEQ ID NO: 35)
GINPSNGGTNFNEKFRG

Heavy chain CDR3 of Ab2: (SEQ ID NO: 36)
RDYNYDGGFDY

Ab4 (IgG1) light chain variable domain (Kappa) cDNA: (SEQ ID NO: 37)
GATATACAGATGACTCAGTCTCCCTCATCACTGAGCGCTTCAGTGGGTGATCGAGTGACCATCACTTGTGTCGTGCTTCAAAGTCCGTATCCACAAGTGG
CTTTAACTACTACATGCACTGGTATCAGCAGAAGCCAGGAAAGCTCCAAAACTGCTTATATATCTGGCCTCTAACTTGGACTCTGGAGTACCTGCTAGAT
TTAGCGGAAGTGGTTCAGGGACAGACTTCACTCTCACCATCTCAAGAAGAAGATATAGCCACTTACTACTGTCTTCCACGGAAGAGAATTG
CCCCTGACCTTCGGTCAAGGAACCAAGCTCCAAATAACCCGA Ab4 light chain variable domain (Kappa): (SEQ ID NO: 38)

FIG. 9 (cont)

DIQMTQSPSSLSASVGDRVTITCRASKSVSTSGFNYMHWYQQTPGKAPKLLIYLASNLDSGVPARFSGSGSGTDFTFTISSLQEEDIATYYCFHGREL
PLTFGQGTKLQITR

Ab4 heavy chain variable domain cDNA: (SEQ ID NO: 39)

CAGGTACAGCTCCAACAGAGCGGTGCTGAGTAAAAAACCAGTTCAAGTGTTAAAGTCTCATGTAAGGCATCTGGGTACACATTCACAAACTACTA
TCTGTACTGGGTACGCCAGGCTCCAGGTCAGGGCTTGAGTGGATAGGGGAATTAACCCTAGTAATGGCGGAACTTCAATGAAAAATTTCGTG
GGCGTGTAACTATTACTGCCGACGAGAGTTCAACAACCGCATATATGGAGTTGAGTTCTCTCGTTCAGAGGATACTGCTTTCTATTTTGTACCGC
CGGGACTACAATTACGATGGGGGATTCGACTATTGGGGCCAGGGAACCACCGTCACAGTGAGTTCT

Ab4 heavy chain variable domain: (SEQ ID NO: 40)

QVQLQQSGAEVKKPGSSVKVSCKASGYTFTNYYLYWVRQAPGQGLEWIGGINPSNGGTNFNEKFRGRVTITADESSTTAYMELSSLRSEDTAFYFCTR
RDYNYDGGFDYWGQGTTVTVSS

Light chain CDR1 of Ab4: (SEQ ID NO: 41)

RASKSVSTSGFNYMH

Light chain CDR2 of Ab4: (SEQ ID NO: 42)

LASNLDS

Light chain CDR3 of Ab4: (SEQ ID NO: 43)

FHGRELPLT

Heavy chain CDR1 of Ab4: (SEQ ID NO: 44)

GYTFTNYYLY

Heavy chain CDR2 of Ab4: (SEQ ID NO: 45)

GINPSNGGTNFNEKFRG

FIG. 9 (cont)

Heavy chain CDR3 of Ab4: (SEQ ID NO: 46)

RDYNYDGGFDY

Ab5 (IgG1) light chain variable domain (Kappa) cDNA: (SEQ ID NO: 47)

GACATCGTCATGACACAGTCTCCGCCAGCGTTGTCCGCCAGTCTAGTTTGTCCGCCAGCGTTGTCCGCCAGCGTTCCAAATCAGTATCCACCTCCGG
GTTTAATTATATGCACTGGTACCAGCAGACACCTGGAAAGGCACCCAAACTGTTGATCTATTTGGCCTCAAACCTGGACTCTGGCGTGCCAGCGCT
TCAGTGGGTCAGGTTCAGGAACTGACTTACTTTCACTATATCCAGCCTCCAAGAAGATATTGCAACACATATATTGTTTTCACGGCAGAGAATTG
CCACTGACTTTCGGACAGGGAACCAAATTGCAAATCACTAGG

Ab5 light chain variable domain (Kappa): (SEQ ID NO: 48)

DIVMTQSPSSLSASVGDRVTITCRASKSVSTSGFNYMHWYQQTPGKAPKLLIYLASNLDSGVPARFSGSGSGTDFTFTISSLQEEDIATYYCFHGREL
PLTFGQGTKLQITR

Ab5 heavy chain variable domain cDNA: (SEQ ID NO: 49)

CAGGTACAGCTCCAACAGAGCCGGTGCAGCTGCTGAGGTAAAAAACCAGGTTCAAGTGTTAAAGTCTCATGTAAGGCATCTGGGTACACATTCACAAAACTACTA
TCTGTACTGGGTACGCCAGGCTCCAGGTCAGGTGAATTAACCCTAGTAGTAATGGCGGAAACTTCAATGAAAAATTTCGTG
GCCGTGTAACTATTACTGCCGACGAGAGTTCAACAACCGCATATATGGAGTTGAGTTCTCTCTTCGTTCAGAGAGATACTGCTTTCTATTTTTGTACCCGC
CGGGACTACAATTACGATGGGGGATTCGACTATTGGGGCCAGGGAACCACCGTCACAGTGAGTTCT

Ab5 heavy chain variable domain: (SEQ ID NO: 50)

QVQLQQSGAEVKKPGSSVKVSCKASGYTFTNYYLYWVRQAPGQGLEWIGGINPSNGGTNFNEKFRGRVTITADESSTAYMELSSLRSEDTAFYFCTR
RDYNYDGGFDYWGQGTTVTVSS

Light chain CDR1 of Ab5: (SEQ ID NO: 51)

RASKSVSTSGFNYMH

Light chain CDR2 of Ab5: (SEQ ID NO: 52)

LASNLDS

FIG. 9 (cont)

Light chain CDR3 of Ab5: (SEQ ID NO: 53)
FHGRELPLT

Heavy chain CDR1 of Ab5: (SEQ ID NO: 54)
GYTFTNYYLY

Heavy chain CDR2 of Ab5: (SEQ ID NO: 55)
GINPSNGGTNFNEKFRG

Heavy chain CDR3 of Ab5: (SEQ ID NO: 56)
RDYNYDGGFDY

Ab7 (IgG1) light chain variable domain (Kappa) cDNA: (SEQ ID NO: 57)
GACATCGTCATGACACAATCACCATCTAGTTTGTCCGCCAGCGTCGGTGATCGGTTACCATCACATGCAGAGCTTCCAAATCAGTATCCACCTCCGG
GTTAATTATATGCACTGGTACCAGCAGACAGGAAAGGCACCCAAACTGGAAAGGCACCCAAACTGTTGATCTATTTGGCCTCAAACCTGGACTCTGGCGTGCCAGCACGCT
TCAGTGGGTCAGGTCAGGATCAGGAACTGACTTTCACTTTCACTATATCCAAGAAGAAGATATTATTGTTTTCACGGCAGAGAATTG
CCACTGACTTTCGGACAGGGAACCAAATTGCAAATCACTAGG Ab7 light chain variable domain (Kappa): (SEQ ID NO: 58)
DIVMTQSPSSLSASVGDRVTITCRASKSVSTSGFNYMHWYQQTPGKAPKLLIYLASNLDSGVPARFSGSGSGTDFTFTISSLQEEDIATYYCFHGREL
PLTFGQGTKLQITR Ab7 heavy chain variable domain cDNA: (SEQ ID NO: 59)
CAAGTGCAACTGCAACTGGAGTCGGCAGCAAAGCGGGGCCCGAAGTTAAAAAGCCAGGGAGCAGTGTCAAGGTAAGTTGTCGTGCTTCTGGTTATACCTTCACAAATTATTA
TCTTTATTGGGTTCGACAGGCTCCAGGACAAGGGCTTGAATGGATTGGCGGGATCAATCCAAGTAACGGCGACCAACTTTAATGAGAAGTTTCGGG

FIG. 9 (cont)

GTAGAGTCACTACTATTACTGCCGACGACGAATCATCAACAACCGCATACACATGGAGCTGAGTTCCTTGCCGATCAGAAGATACCGCTTTTATTTTGCACACGC
CGCGGATTACAATTATGATGGTGGCTTTGATTATTGGGGGCAAGAACTACTGTCACAGTCAGTTCC

Ab7 heavy chain variable domain: (SEQ ID NO: 60)
QVQLQQSGAEVKKPGSSVKVSCRASGYTFTNYYLYWVRQAPGQGLEWIGGINPSNGGTNFNEKFRGRVTITADESSTTAYMELSSLRSEDTAFYFCTR
RDYNYDGGFDYWGQGTTVTVSS Light chain CDR1 of Ab7: (SEQ ID NO: 61)
RASKSVSTSGFNYMH Light chain CDR2 of Ab7: (SEQ ID NO: 62)
LASNLDS Light chain CDR3 of Ab7: (SEQ ID NO: 63)
FHGRELPLT Heavy chain CDR1 of Ab7: (SEQ ID NO: 64)
GYTFTNYYLY Heavy chain CDR2 of Ab7: (SEQ ID NO: 65)
GINPSNGGTNFNEKFRG Heavy chain CDR3 of Ab7: (SEQ ID NO: 66)
RDYNYDGGFDY Ab8 (IgG1) light chain variable domain (Kappa) cDNA: (SEQ ID NO: 67)

FIG. 9 (cont)

GACATTGTAATGACTCAAAGTCCTGACTCCCTTGCCGTTAGTCTGGGGAGCGGGCAACCATAAATTGTCGCGCCTCAAAGAGTGTGAGCACATCCGG
CTTCAACTATATGCATTGGTACCAGCAGAAACCAGGACAACCTCCTAAATTGCTGATATCTTGCATCTAATCTGATTCAGGCGTGCCTGATCGTT
TCTCAGGCAGCGGGAGCGGGACTGATTTCACTCTGACTATTCGCCCCTTTGCAAGCCGAGGACGTTGCTGTTTACTATTGTCAACATGGCCGAACTT
CCACTTACTTTCGGCCAAGGCACAAAGCTGGAGATCAAG

Ab8 light chain variable domain (Kappa): (SEQ ID NO: 68)

DIVMTQSPDSLAVSLGERATINCRASKSVSTSGFNYMHWYQQKPGQPPKLLIYLASNLDSGVPDRFSGSGSGTDFTLTIRPLQAEDVAVYYCQHGREL
PLTFGQGTKLEIK

Ab8 heavy chain variable domain cDNA: (SEQ ID NO: 69)

GAGGTTCAGTTGCAAGAAGTGGAGCAGAGTGAAGAAGCCTGGTTCTTCCGTGAAGGTTAGTTGTAAAGCATCCGGCTATACTTTTACTAACTACTA
CCTGTACTGGGTACGACAAGCACCTGGGCAAGGCCTGAATGGATGGGCGGAATTAACCCCAGCAACGGAGGCACAAACTTTAATGAAAAATTCCGTG
GCCGTGTTGACCATTACCGCTGACGAATCTACCAGTACACAGCATATATGGAATTGAGCTCTCGCTAGTGAAGATACAGCTGTCTATTATTGTGCCCGA
AGAGACTATAATTATGATGGGGCTTCGATTACTGGAGGCTTCAAGGACACAACAGTGACCGTGTCTTCA

Ab8 heavy chain variable domain: (SEQ ID NO: 70)

EVQLQESGAEVKKPGSSVKVSCKASGYTFTNYYLYWVRQAPGQGLEWMGGINPSNGGTNFNEKFRGRVTITADESTSTAYMELSSLRSEDTAVYYCAR
RDYNYDGFDYWGQGTTVTVSS

Light chain CDR1 of Ab8: (SEQ ID NO: 71)

RASKSVSTSGFNYMH

Light chain CDR2 of Ab8: (SEQ ID NO: 72)

LASNLDS

Light chain CDR3 of Ab8: (SEQ ID NO: 73)

QHGRELPLT

FIG. 9 (cont)

Heavy chain CDR1 of Ab8: (SEQ ID NO: 74)
GYTFTNYYLY

Heavy chain CDR2 of Ab8: (SEQ ID NO: 75)
GINPSNGGTNFNEKFRG

Heavy chain CDR3 of Ab8: (SEQ ID NO: 76)
RDYNYDGGFDY

Human PD-1 NP_005009.2 (SEQ ID NO: 77)

| | | | | | |
|---|---|---|---|---|---|
| MQIPQAPWPV | VWAVLQLGWR | PGWFLDSPDR | PWNPPTFSPA | LLVVTEGDNA | TFTCSFSNTS |
| ESFVLNWYRM | SPSNQTDKLA | AFPEDRSQPG | QDCRFRVTQL | PNGRDFHMSV | VRARRNDSGT |
| YLCGAISLAP | KAQIKESLRA | ELRVTERRAE | VPTAHPSPSP | RPAGQFQTLV | VGVVGGLLGS |
| LVLLVWVLAV | ICSRAARGTI | GARRTGQPLK | EDPSAVPVFS | VDYGELDFQW | REKTPEPPVP |
| CVPEQTEYAT | IVFPSGMGTS | SPARRGSADG | PRSAQPLRPE | DGHCSWP | |

Signal Peptide (SEQ ID NO: 78)
METDTLLLWVLLLWVPGSTG

Signal Peptide (SEQ ID NO: 79)
MGCSWVMLFLVATATGVHS

FIG. 9 (cont)

SEQUENCE LISTING

```
<160> NUMBER OF SEQ ID NOS: 79

<210> SEQ ID NO 1
<211> LENGTH: 499
<212> TYPE: DNA
<213> ORGANISM: Mus musculus

<400> SEQUENCE: 1
atggagacag acacactcct gctatgggta ctgctgctct gggttccagg ttccactggt      60
gacattgtgc tgacacagtc tcctgcttcc ttagctgtat ctctggggca gagggccacc     120
atctcatgca gggccagcaa aagtgtcagt acttctggct ttaattatat gcactggtac     180
caacagaaac caggacagcc acccaaactc ctcatctatc ttgcatccaa cctagattct     240
ggggtccctg ccaggttcag tggcagtggg tctgggacag acttcaccct caacatccat     300
cctgtggagg aggaggatgc tgcgacctat tactgtcagc acggtaggga acttccgctc     360
acgttcggtg ctgggaccaa gctggagctg agacgggctg atgctgcacc aactgtatcc     420
atcttcccac catccagtga gcagttaaca tctggaggtg cctcagtcgt gtgcttcttg     480
aacaacttct accccaaag                                                  499

<210> SEQ ID NO 2
<211> LENGTH: 115
<212> TYPE: PRT
<213> ORGANISM: Mus musculus

<400> SEQUENCE: 2
```

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Phe Asn Tyr Met His Trp Tyr Gln Gln Lys Pro Gly Gln Pro Pro
        35                  40                  45

Lys Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Gly Arg
            85                  90                  95

Glu Leu Pro Leu Thr Phe Gly Ala Gly Thr Lys Leu Glu Leu Arg Arg
            100                 105                 110

Ala Asp Ala
        115

<210> SEQ ID NO 3
<211> LENGTH: 732
<212> TYPE: DNA
<213> ORGANISM: Mus musculus

<400> SEQUENCE: 3
atgggatgca gctgggtaat gctcttttg gtagcaacag ctacaggtgt ccactcccag        60
gtccaactgc agcagcctgg ggctgaactg gtgaaacctg ggcttcagt gaagttgtcc      120
tgcagggctt ctggctacac cttcaccaac tactatttgt attgggtgaa gcagaggcct     180
ggacaaggcc ttgagtggat tggggggatt aatcctagca atggtggtac taacttcaat     240
gagaagttca ggggcaaggc cacactgact gtagacaaat cctccagcac agcctacatg     300
caactcagca gcctgacatc tgaggactct gcggtctatt tctgtacaag aagggactat     360
aactacgacg ggggctttga ctactgggc caaggctcca ctctcacagt ctcctcagcc     420
aaaacgacac ccccatctgt ctatccactg gcccctggat ctgctgccca actaactcc     480
atggtgaccc tgggatgcct ggtcaagggc tatttccctg agccagtgac agtgacctgg     540
aactctggat ccctgtccag cggtgtgcac accttcccag ctgtcctgca gtctgacctc     600
tacactctga gcagctcagt gactgtcccc tccagcacct ggcccagcga gaccgtcacc     660
tgcaacgttg cccacccggc cagcagcacc aaggtggaca gaaaattgt gcccagggat      720
tgtgggttgt aa                                                        732

<210> SEQ ID NO 4
<211> LENGTH: 120
<212> TYPE: PRT
<213> ORGANISM: Mus musculus

<400> SEQUENCE: 4

Gln Gln Pro Gly Ala Glu Leu Val Lys Pro Gly Ala Ser Val Lys Leu
1               5                   10                  15

Ser Cys Arg Ala Ser Gly Tyr Thr Phe Thr Asn Tyr Tyr Leu Tyr Trp
            20                  25                  30

Val Lys Gln Arg Pro Gly Gln Gly Leu Glu Trp Ile Gly Gly Ile Asn
            35                  40                  45

Pro Ser Asn Gly Gly Thr Asn Phe Asn Glu Lys Phe Arg Gly Lys Ala
    50                  55                  60

```
Thr Leu Thr Val Asp Lys Ser Ser Ser Thr Ala Tyr Met Gln Leu Ser
 65                  70                  75                  80

Ser Leu Thr Ser Glu Asp Ser Ala Val Tyr Phe Cys Thr Arg Arg Asp
                 85                  90                  95

Tyr Asn Tyr Asp Gly Gly Phe Asp Tyr Trp Gly Gln Gly Ser Thr Leu
            100                 105                 110

Thr Val Ser Ser Ala Lys Thr Thr
        115                 120

<210> SEQ ID NO 5
<211> LENGTH: 15
<212> TYPE: PRT
<213> ORGANISM: Mus musculus

<400> SEQUENCE: 5

Arg Ala Ser Lys Ser Val Ser Thr Ser Gly Phe Asn Tyr Met His
 1               5                  10                  15

<210> SEQ ID NO 6
<211> LENGTH: 7
<212> TYPE: PRT
<213> ORGANISM: Mus musculus

<400> SEQUENCE: 6

Leu Ala Ser Asn Leu Asp Ser
 1               5

<210> SEQ ID NO 7
<211> LENGTH: 9
<212> TYPE: PRT
<213> ORGANISM: Mus musculus

<400> SEQUENCE: 7

Gln His Gly Arg Glu Leu Pro Leu Thr
 1               5

<210> SEQ ID NO 8
<211> LENGTH: 7
<212> TYPE: PRT
<213> ORGANISM: Mus musculus

<400> SEQUENCE: 8

Gly Tyr Thr Phe Thr Asn Tyr
 1               5

<210> SEQ ID NO 9
<211> LENGTH: 6
<212> TYPE: PRT
<213> ORGANISM: Mus musculus

<400> SEQUENCE: 9

Asn Pro Ser Asn Gly Gly
 1               5

<210> SEQ ID NO 10
<211> LENGTH: 11
<212> TYPE: PRT
<213> ORGANISM: Mus musculus

<400> SEQUENCE: 10

Arg Asp Tyr Asn Tyr Asp Gly Gly Phe Asp Tyr
 1               5                  10
```

```
<210> SEQ ID NO 11
<211> LENGTH: 218
<212> TYPE: PRT
<213> ORGANISM: Mus musculus

<400> SEQUENCE: 11

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Phe Asn Tyr Met His Trp Tyr Gln Gln Lys Pro Gly Gln Pro Pro
        35                  40                  45

Lys Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Gly Arg
                85                  90                  95

Glu Leu Pro Leu Thr Phe Gly Ala Gly Thr Lys Leu Glu Leu Arg Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 12
<211> LENGTH: 440
<212> TYPE: PRT
<213> ORGANISM: Mus musculus

<400> SEQUENCE: 12

Gln Gln Pro Gly Ala Glu Leu Val Lys Pro Gly Ala Ser Val Lys Leu
1               5                   10                  15

Ser Cys Arg Ala Ser Gly Tyr Thr Phe Thr Asn Tyr Leu Tyr Trp
            20                  25                  30

Val Lys Gln Arg Pro Gly Gln Gly Leu Glu Trp Ile Gly Gly Ile Asn
        35                  40                  45

Pro Ser Asn Gly Gly Thr Asn Phe Asn Glu Lys Phe Arg Gly Lys Ala
    50                  55                  60

Thr Leu Thr Val Asp Lys Ser Ser Ser Thr Ala Tyr Met Gln Leu Ser
65                  70                  75                  80

Ser Leu Thr Ser Glu Asp Ser Ala Val Tyr Phe Cys Thr Arg Arg Asp
                85                  90                  95

Tyr Asn Tyr Asp Gly Gly Phe Asp Tyr Trp Gly Gln Gly Ser Thr Leu
            100                 105                 110

Thr Val Ser Ser Ala Lys Thr Thr Pro Pro Ser Val Tyr Pro Leu Ala
```

```
            115                 120                 125
Pro Gly Ser Ala Ala Gln Thr Asn Ser Met Val Thr Leu Gly Cys Leu
            130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
            195                 200                 205

Val Asp Lys Lys Ile Val Pro Arg Asp Cys Gly Cys Lys Pro Cys Ile
210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Lys Pro Arg Glu Glu Gln
            275                 280                 285

Ile Asn Ser Thr Phe Arg Ser Val Ser Glu Leu Pro Ile Met His Gln
            290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
                325                 330                 335

Lys Ala Pro Gln Val Tyr Thr Ile Pro Pro Lys Glu Gln Met Ala
            340                 345                 350

Lys Asp Lys Val Ser Leu Thr Cys Met Ile Thr Asn Phe Phe Pro Glu
            355                 360                 365

Asp Ile Thr Val Glu Trp Gln Trp Asn Gly Gln Pro Ala Glu Asn Tyr
370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His His Thr Glu Lys
            420                 425                 430

Ser Leu Ser His Ser Pro Gly Lys
            435                 440

<210> SEQ ID NO 13
<211> LENGTH: 238
<212> TYPE: PRT
<213> ORGANISM: Mus musculus

<400> SEQUENCE: 13

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Arg Ala Ser Lys Ser
            35                  40                  45
```

```
Val Ser Thr Ser Gly Phe Asn Tyr Met His Trp Tyr Gln Gln Lys Pro
 50                  55                  60
Gly Gln Pro Pro Lys Leu Leu Ile Tyr Leu Ala Ser Asn Leu Asp Ser
 65                  70                  75                  80
Gly Val Pro Ala Arg Phe Ser Gly Ser Gly Ser Gly Thr Asp Phe Thr
                 85                  90                  95
Leu Asn Ile His Pro Val Glu Glu Asp Ala Ala Thr Tyr Tyr Cys
                100                 105                 110
Gln His Gly Arg Glu Leu Pro Leu Thr Phe Gly Ala Gly Thr Lys Leu
                115                 120                 125
Glu Leu Arg Arg Ala Asp Ala Ala Pro Thr Val Ser Ile Phe Pro Pro
130                 135                 140
Ser Ser Glu Gln Leu Thr Ser Gly Gly Ala Ser Val Val Cys Phe Leu
145                 150                 155                 160
Asn Asn Phe Tyr Pro Lys Asp Ile Asn Val Lys Trp Lys Ile Asp Gly
                165                 170                 175
Ser Glu Arg Gln Asn Gly Val Leu Asn Ser Trp Thr Asp Gln Asp Ser
                180                 185                 190
Lys Asp Ser Thr Tyr Ser Met Ser Ser Thr Leu Thr Leu Thr Lys Asp
                195                 200                 205
Glu Tyr Glu Arg His Asn Ser Tyr Thr Cys Glu Ala Thr His Lys Thr
210                 215                 220
Ser Thr Ser Pro Ile Val Lys Ser Phe Asn Arg Asn Glu Cys
225                 230                 235

<210> SEQ ID NO 14
<211> LENGTH: 463
<212> TYPE: PRT
<213> ORGANISM: Mus musculus

<400> SEQUENCE: 14

Met Gly Cys Ser Trp Val Met Leu Phe Leu Val Ala Thr Ala Thr Gly
 1                   5                  10                  15
Val His Ser Gln Val Gln Leu Gln Gln Pro Gly Ala Glu Leu Val Lys
                 20                  25                  30
Pro Gly Ala Ser Val Lys Leu Ser Cys Arg Ala Ser Gly Tyr Thr Phe
                 35                  40                  45
Thr Asn Tyr Tyr Leu Tyr Trp Val Lys Gln Arg Pro Gly Gln Gly Leu
 50                  55                  60
Glu Trp Ile Gly Gly Ile Asn Pro Ser Asn Gly Gly Thr Asn Phe Asn
 65                  70                  75                  80
Glu Lys Phe Arg Gly Lys Ala Thr Leu Thr Val Asp Lys Ser Ser Ser
                 85                  90                  95
Thr Ala Tyr Met Gln Leu Ser Ser Leu Thr Ser Glu Asp Ser Ala Val
                100                 105                 110
Tyr Phe Cys Thr Arg Arg Asp Tyr Asn Tyr Asp Gly Phe Asp Tyr
                115                 120                 125
Trp Gly Gln Gly Ser Thr Leu Thr Val Ser Ser Ala Lys Thr Thr Pro
130                 135                 140
Pro Ser Val Tyr Pro Leu Ala Pro Gly Ser Ala Ala Gln Thr Asn Ser
145                 150                 155                 160
Met Val Thr Leu Gly Cys Leu Val Lys Gly Tyr Phe Pro Glu Pro Val
                165                 170                 175
Thr Val Thr Trp Asn Ser Gly Ser Leu Ser Ser Gly Val His Thr Phe
                180                 185                 190
```

Pro Ala Val Leu Gln Ser Asp Leu Tyr Thr Leu Ser Ser Val Thr
        195                 200                 205
Val Pro Ser Ser Thr Trp Pro Ser Glu Thr Val Thr Cys Asn Val Ala
210                 215                 220
His Pro Ala Ser Ser Thr Lys Val Asp Lys Lys Ile Val Pro Arg Asp
225                 230                 235                 240
Cys Gly Cys Lys Pro Cys Ile Cys Thr Val Pro Glu Val Ser Ser Val
                245                 250                 255
Phe Ile Phe Pro Pro Lys Pro Lys Asp Val Leu Thr Ile Thr Leu Thr
            260                 265                 270
Pro Lys Val Thr Cys Val Val Asp Ile Ser Lys Asp Asp Pro Glu
        275                 280                 285
Val Gln Phe Ser Trp Phe Val Asp Asp Val Glu Val His Thr Ala Gln
    290                 295                 300
Thr Lys Pro Arg Glu Glu Gln Ile Asn Ser Thr Phe Arg Ser Val Ser
305                 310                 315                 320
Glu Leu Pro Ile Met His Gln Asp Trp Leu Asn Gly Lys Glu Phe Lys
                325                 330                 335
Cys Arg Val Asn Ser Ala Ala Phe Pro Ala Pro Ile Glu Lys Thr Ile
            340                 345                 350
Ser Lys Thr Lys Gly Arg Pro Lys Ala Pro Gln Val Tyr Thr Ile Pro
        355                 360                 365
Pro Pro Lys Glu Gln Met Ala Lys Asp Lys Val Ser Leu Thr Cys Met
    370                 375                 380
Ile Thr Asn Phe Phe Pro Glu Asp Ile Thr Val Glu Trp Gln Trp Asn
385                 390                 395                 400
Gly Gln Pro Ala Glu Asn Tyr Lys Asn Thr Gln Pro Ile Met Asp Thr
                405                 410                 415
Asp Gly Ser Tyr Phe Val Tyr Ser Lys Leu Asn Val Gln Lys Ser Asn
            420                 425                 430
Trp Glu Ala Gly Asn Thr Phe Thr Cys Ser Val Leu His Glu Gly Leu
        435                 440                 445
His Asn His His Thr Glu Lys Ser Leu Ser His Ser Pro Gly Lys
    450                 455                 460

<210> SEQ ID NO 15
<211> LENGTH: 330
<212> TYPE: DNA
<213> ORGANISM: Artificial Sequence
<220> FEATURE:
<223> OTHER INFORMATION: cDNA encoding light chain variable domain (VL)

<400> SEQUENCE: 15
gacatcgtcc ttacgcaaag cccggcgacc ctcagtttga gccctgggga agagcaacg    60 ctgtcttgta gagcatccaa atcagtctca acttctggtt ttaattacat gcactggtat  120
caacagaagc caggacaagc acctagattg ctgatctttc tggcgtcaaa tctggcctct  180
ggcgttccag cccggtttag cggttctgga agcggaacgg actttaccct taccatatca  240
tcactcgaac cagaggactt tgcggtatat tactgccaac atggacggga gctgcccttg  300
acgtttggtc aaggaacgaa gttggagata                                    330

<210> SEQ ID NO 16
<211> LENGTH: 110
<212> TYPE: PRT
<213> ORGANISM: Artificial Sequence

<220> FEATURE:
<223> OTHER INFORMATION: VL

<400> SEQUENCE: 16

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
                20                  25                  30

Gly Phe Asn Tyr Met His Trp Tyr Gln Gln Lys Pro Gly Gln Ala Pro
            35                  40                  45

Arg Leu Leu Ile Phe Leu Ala Ser Asn Leu Ala Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Gly Arg
                85                  90                  95

Glu Leu Pro Leu Thr Phe Gly Gln Gly Thr Lys Leu Glu Ile
            100                 105                 110

<210> SEQ ID NO 17
<211> LENGTH: 360
<212> TYPE: DNA
<213> ORGANISM: Artificial Sequence
<220> FEATURE:
<223> OTHER INFORMATION: cDNA encoding heavy chain variable domain (VH)

<400> SEQUENCE: 17
caagtccagc ttgtacaaag cggtgccgaa gtgaaaaaac cgggcgcaag cgtcaaggtt      60
tcatgcaagg cgagtggata ccctttacc aactattaca tgtactgggt gcggcaggca      120
cccgggcagg gactggaatg gatcggtggt attaacccaa gtaatggtgg tacaaatttc     180
aacgaaaagt ttaagaacaa agcgacgatg acagtagaca atctacaag taccgcatac      240 atggagctga gctcactgag atctgaggac accgcagtct attactgcac acggcgagat     300
tacaattacg atggagggtt cgactactgg ggccaaggga ctttggtgac tgtatcctcc     360

<210> SEQ ID NO 18
<211> LENGTH: 120
<212> TYPE: PRT
<213> ORGANISM: Artificial Sequence
<220> FEATURE:
<223> OTHER INFORMATION: VH

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Ile
            35                  40                  45

Gly Gly Ile Asn Pro Ser Asn Gly Gly Thr Asn Phe Asn Glu Lys Phe
        50                  55                  60

Lys Asn Lys Ala Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Arg Asp Tyr Asn Tyr Asp Gly Gly Phe Asp Tyr Trp Gly Gln
            100                 105                 110

```
Gly Thr Leu Val Thr Val Ser Ser
        115             120

<210> SEQ ID NO 19
<211> LENGTH: 15
<212> TYPE: PRT
<213> ORGANISM: Artificial Sequence
<220> FEATURE:
<223> OTHER INFORMATION: CDR sequence

<400> SEQUENCE: 19

Arg Ala Ser Lys Ser Val Ser Thr Ser Gly Phe Asn Tyr Met His
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: CDR sequence

<400> SEQUENCE: 20

Leu Ala Ser Asn Leu Ala Ser
1               5

<210> SEQ ID NO 21
<211> LENGTH: 9
<212> TYPE: PRT
<213> ORGANISM: Artificial Sequence
<220> FEATURE:
<223> OTHER INFORMATION: CDR sequence

<400> SEQUENCE: 21

Gln His Gly Arg Glu Leu Pro Leu Thr
1               5

<210> SEQ ID NO 22
<211> LENGTH: 10
<212> TYPE: PRT
<213> ORGANISM: Artificial Sequence
<220> FEATURE:
<223> OTHER INFORMATION: CDR sequence

<400> SEQUENCE: 22

Gly Tyr Thr Phe Thr Asn Tyr Tyr Met Tyr
1               5                   10

<210> SEQ ID NO 23
<211> LENGTH: 17
<212> TYPE: PRT
<213> ORGANISM: Artificial Sequence
<220> FEATURE:
<223> OTHER INFORMATION: CDR sequence

<400> SEQUENCE: 23

Gly Ile Asn Pro Ser Asn Gly Gly Thr Asn Phe Asn Glu Lys Phe Lys
1               5                   10                  15

Asn

<210> SEQ ID NO 24
<211> LENGTH: 11
<212> TYPE: PRT
<213> ORGANISM: Artificial Sequence
<220> FEATURE:
<223> OTHER INFORMATION: CDR sequence

<400> SEQUENCE: 24
```

Arg Asp Tyr Asn Tyr Asp Gly Gly Phe Asp Tyr
1               5                   10

<210> SEQ ID NO 25
<211> LENGTH: 217
<212> TYPE: PRT
<213> ORGANISM: Artificial Sequence
<220> FEATURE:
<223> OTHER INFORMATION: light chain

<400> SEQUENCE: 25

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
                20                  25                  30

Gly Phe Asn Tyr Met His Trp Tyr Gln Gln Lys Pro Gly Gln Ala Pro
            35                  40                  45

Arg Leu Leu Ile Phe Leu Ala Ser Asn Leu Ala Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Gly Arg
                85                  90                  95

Glu Leu Pro Leu Thr Phe Gly Gln Gly Thr Lys Leu Glu Ile Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 26
<211> LENGTH: 450
<212> TYPE: PRT
<213> ORGANISM: Artificial Sequence
<220> FEATURE:
<223> OTHER INFORMATION: heavy chain

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Ile
            35                  40                  45

Gly Gly Ile Asn Pro Ser Asn Gly Gly Thr Asn Phe Asn Glu Lys Phe
        50                  55                  60

Lys Asn Lys Ala Thr Met Thr Val Asp Lys Ser Thr Ser Thr Ala Tyr

```
                65                  70                  75                  80
            Met Glu Leu Ser Ser Leu Arg Ser Glu Asp Thr Ala Val Tyr Tyr Cys
                                85                  90                  95

Thr Arg Arg Asp Tyr Asn Tyr Asp Gly Gly Phe Asp Tyr Trp Gly Gln
                            100                 105                 110

Gly Thr Leu Val Thr Val Ser Ser Ala Ser Thr Lys Gly Pro Ser Val
                        115                 120                 125

Phe Pro Leu Ala Pro Ser Ser Lys Ser Thr Ser Gly Gly Thr Ala Ala
                    130                 135                 140

Leu Gly Cys Leu Val Lys Asp Tyr Phe Pro Glu Pro Val Thr Val Ser
            145                 150                 155                 160

Trp Asn Ser Gly Ala Leu Thr Ser Gly Val His Thr Phe Pro Ala Val
                                165                 170                 175

Leu Gln Ser Ser Gly Leu Tyr Ser Leu Ser Ser Val Val Thr Val Pro
                            180                 185                 190

Ser Ser Ser Leu Gly Thr Gln Thr Tyr Ile Cys Asn Val Asn His Lys
                        195                 200                 205

Pro Ser Asn Thr Lys Val Asp Lys Lys Val Glu Pro Lys Ser Cys Asp
                    210                 215                 220

Lys Thr His Thr Cys Pro Pro Cys Pro Ala Pro Glu Leu Leu Gly Gly
            225                 230                 235                 240

Pro Ser Val Phe Leu Phe Pro Pro Lys Pro Lys Asp Thr Leu Met Ile
                                245                 250                 255

Ser Arg Thr Pro Glu Val Thr Cys Val Val Val Asp Val Ser His Glu
                            260                 265                 270

Asp Pro Glu Val Lys Phe Asn Trp Tyr Val Asp Gly Val Glu Val His
                        275                 280                 285

Asn Ala Lys Thr Lys Pro Arg Glu Glu Gln Tyr Asn Ser Thr Tyr Arg
                    290                 295                 300

Val Val Ser Val Leu Thr Val Leu His Gln Asp Trp Leu Asn Gly Lys
            305                 310                 315                 320

Glu Tyr Lys Cys Lys Val Ser Asn Lys Ala Leu Pro Ala Pro Ile Glu
                                325                 330                 335

Lys Thr Ile Ser Lys Ala Lys Gly Gln Pro Arg Glu Pro Gln Val Tyr
                            340                 345                 350

Thr Leu Pro Pro Ser Arg Asp Glu Leu Thr Lys Asn Gln Val Ser Leu
                        355                 360                 365

Thr Cys Leu Val Lys Gly Phe Tyr Pro Ser Asp Ile Ala Val Glu Trp
                    370                 375                 380

Glu Ser Asn Gly Gln Pro Glu Asn Asn Tyr Lys Thr Thr Pro Pro Val
            385                 390                 395                 400

Leu Asp Ser Asp Gly Ser Phe Phe Leu Tyr Ser Lys Leu Thr Val Asp
                                405                 410                 415

Lys Ser Arg Trp Gln Gln Gly Asn Val Phe Ser Cys Ser Val Met His
                            420                 425                 430

Glu Ala Leu His Asn His Tyr Thr Gln Lys Ser Leu Ser Leu Ser Pro
                        435                 440                 445

Gly Lys
                450

<210> SEQ ID NO 27
<211> LENGTH: 336
<212> TYPE: DNA
<213> ORGANISM: Artificial Sequence
```

<220> FEATURE:
<223> OTHER INFORMATION: cDNA encoding VL

<400> SEQUENCE: 27

```
gatattcaga tgacacaaag cccctcaagc cttagcgcat ccgttggcga ccgtgtgacc    60
ataacttgcc gtgcatcaaa aagcgtgagt acctctggtt tcaattacat gcactggtac   120
caacaaacac ctggaaaagc tcccaaactt ctgatctatc ttgcctctaa cctcgatagt   180
ggtgtaccat cccgctttag tggaagcgga agtgggactg actttacctt tactatttct   240
tccttgcaac tgaagacat tgccacctat tattgttttc acggccgcga actgccccctt   300
actttcgggc agggcacaaa gttgcagata acaagg                              336
```

<210> SEQ ID NO 28
<211> LENGTH: 112
<212> TYPE: PRT
<213> ORGANISM: Artificial Sequence
<220> FEATURE:
<223> OTHER INFORMATION: VL

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Phe Asn Tyr Met His Trp Tyr Gln Gln Thr Pro Gly Lys Ala Pro
        35                  40                  45

Lys Leu Leu Ile Tyr Leu Ala Ser Asn Leu Asp Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Phe His Gly Arg
                85                  90                  95

Glu Leu Pro Leu Thr Phe Gly Gln Gly Thr Lys Leu Gln Ile Thr Arg
            100                 105                 110
```

<210> SEQ ID NO 29
<211> LENGTH: 360
<212> TYPE: DNA
<213> ORGANISM: Artificial Sequence
<220> FEATURE:
<223> OTHER INFORMATION: cDNA encoding VH

<400> SEQUENCE: 29

```
caggtacagc tccaacagag cggtgctgag gtaaaaaaac caggttcaag tgttaaagtc    60
tcatgtaagg catctgggta cacattcaca aactactatc tgtactgggt acgccaggct   120
ccaggtcagg gccttgagtg gataggcgga attaaccctta gtaatggcgg gaccaacttc   180
aatgaaaaat tcgtgggcg tgtaactatt actgccgacg agagttcaac aaccgcatat   240
atggagttga gttctcttcg ttcagaggat actgctttct attttttgtac ccgccgggac   300
tacaattacg atgggggatt cgactattgg gggcagggaa ccaccgtcac agtgagttct   360
```

<210> SEQ ID NO 30
<211> LENGTH: 120
<212> TYPE: PRT
<213> ORGANISM: Artificial Sequence
<220> FEATURE:
<223> OTHER INFORMATION: VH

<400> SEQUENCE: 30

Gln Val Gln Leu Gln Gln Ser Gly Ala Glu Val Lys Pro Gly Ser
1               5                   10                  15

Ser Val Lys Val Ser Cys Lys Ala Ser Gly Tyr Thr Phe Thr Asn Tyr
            20                  25                  30

Tyr Leu Tyr Trp Val Arg Gln Ala Pro Gly Gln Gly Leu Glu Trp Ile
            35                  40                  45

Gly Gly Ile Asn Pro Ser Asn Gly Gly Thr Asn Phe Asn Glu Lys Phe
        50                  55                  60

Arg Gly Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Arg Asp Tyr Asn Tyr Asp Gly Gly Phe Asp Tyr Trp Gly Gln
            100                 105                 110

Gly Thr Thr Val Thr Val Ser Ser
        115                 120

<210> SEQ ID NO 31
<211> LENGTH: 15
<212> TYPE: PRT
<213> ORGANISM: Artificial Sequence
<220> FEATURE:
<223> OTHER INFORMATION: CDR sequence

<400> SEQUENCE: 31

Arg Ala Ser Lys Ser Val Ser Thr Ser Gly Phe Asn Tyr Met His
1               5                   10                  15

<210> SEQ ID NO 32
<211> LENGTH: 7
<212> TYPE: PRT
<213> ORGANISM: Artificial Sequence
<220> FEATURE:
<223> OTHER INFORMATION: CDR sequence

<400> SEQUENCE: 32

Leu Ala Ser Asn Leu Asp Ser
1               5

<210> SEQ ID NO 33
<211> LENGTH: 9
<212> TYPE: PRT
<213> ORGANISM: Artificial Sequence
<220> FEATURE:
<223> OTHER INFORMATION: CDR sequence

<400> SEQUENCE: 33

Phe His Gly Arg Glu Leu Pro Leu Thr
1               5

<210> SEQ ID NO 34
<211> LENGTH: 10
<212> TYPE: PRT
<213> ORGANISM: Artificial Sequence
<220> FEATURE:
<223> OTHER INFORMATION: CDR sequence

<400> SEQUENCE: 34

Gly Tyr Thr Phe Thr Asn Tyr Tyr Leu Tyr
1               5                   10

<210> SEQ ID NO 35

```
<211> LENGTH: 17
<212> TYPE: PRT
<213> ORGANISM: Artificial Sequence
<220> FEATURE:
<223> OTHER INFORMATION: CDR sequence

<400> SEQUENCE: 35

Gly Ile Asn Pro Ser Asn Gly Gly Thr Asn Phe Asn Glu Lys Phe Arg
1               5                   10                  15
Gly

<210> SEQ ID NO 36
<211> LENGTH: 11
<212> TYPE: PRT
<213> ORGANISM: Artificial Sequence
<220> FEATURE:
<223> OTHER INFORMATION: CDR sequence

<400> SEQUENCE: 36

Arg Asp Tyr Asn Tyr Asp Gly Gly Phe Asp Tyr
1               5                   10

<210> SEQ ID NO 37
<211> LENGTH: 336
<212> TYPE: DNA
<213> ORGANISM: Artificial Sequence
<220> FEATURE:
<223> OTHER INFORMATION: cDNA encoding VL

<400> SEQUENCE: 37
gatatacaga tgactcagtc tccctcatca ctgagcgctt cagtgggtga tcgagtgacc      60
atcacttgtc gtgcttcaaa gtccgtatcc acaagtggct taactacat gcactggtat     120
cagcagaccc ctgggaaagc tccaaaactg cttatatatc tggcctctaa cttggactct    180
ggagtacctg ctagatttag cggaagtggt tcagggacag acttcacctt taccatctca    240
tccctccaag aagaagatat agccacttac tactgcttcc acggaagaga attgcccctg    300
accttcggtc aaggaaccaa gctccaaata acccga                              336

<210> SEQ ID NO 38
<211> LENGTH: 112
<212> TYPE: PRT
<213> ORGANISM: Artificial Sequence
<220> FEATURE:
<223> OTHER INFORMATION: VL

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Phe Asn Tyr Met His Trp Tyr Gln Gln Thr Pro Gly Lys Ala Pro
        35                  40                  45

Lys Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Phe Thr Ile Ser
65                  70                  75                  80

Ser Leu Gln Glu Glu Asp Ile Ala Thr Tyr Tyr Cys Phe His Gly Arg
                85                  90                  95

Glu Leu Pro Leu Thr Phe Gly Gln Gly Thr Lys Leu Gln Ile Thr Arg
            100                 105                 110
```

<210> SEQ ID NO 39
<211> LENGTH: 360
<212> TYPE: DNA
<213> ORGANISM: Artificial Sequence
<220> FEATURE:
<223> OTHER INFORMATION: cDNA encoding VH

<400> SEQUENCE: 39

```
caggtacagc tccaacagag cggtgctgag gtaaaaaaac caggttcaag tgttaaagtc    60
tcatgtaagg catctgggta cacattcaca aactactatc tgtactgggt acgccaggct   120
ccaggtcagg gccttgagtg ataggcgga attaacccta gtaatggcgg gaccaacttc   180
aatgaaaaat ttcgtgggcg tgtaactatt actgccgacg agagttcaac aaccgcatat   240
atggagttga gttctcttcg ttcagaggat actgctttct attttgtac ccgccgggac   300 tacaattacg atgggggatt cgactattgg gggcaggaa ccaccgtcac agtgagttct   360
```

<210> SEQ ID NO 40
<211> LENGTH: 120
<212> TYPE: PRT
<213> ORGANISM: Artificial Sequence
<220> FEATURE:
<223> OTHER INFORMATION: VH

<400> SEQUENCE: 40

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Leu Tyr Trp Val Arg Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Arg Gly Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Arg Asp Tyr Asn Tyr Asp Gly Gly Phe Asp Tyr Trp Gly Gln
            100                 105                 110

Gly Thr Thr Val Thr Val Ser Ser
        115                 120

<210> SEQ ID NO 41
<211> LENGTH: 15
<212> TYPE: PRT
<213> ORGANISM: Artificial Sequence
<220> FEATURE:
<223> OTHER INFORMATION: CDR sequence

<400> SEQUENCE: 41

Arg Ala Ser Lys Ser Val Ser Thr Ser Gly Phe Asn Tyr Met His
1               5                   10                  15

<210> SEQ ID NO 42
<211> LENGTH: 7
<212> TYPE: PRT
<213> ORGANISM: Artificial Sequence
<220> FEATURE:
<223> OTHER INFORMATION: CDR sequence

<400> SEQUENCE: 42

Leu Ala Ser Asn Leu Asp Ser
1               5

<210> SEQ ID NO 43
<211> LENGTH: 9
<212> TYPE: PRT
<213> ORGANISM: Artificial Sequence
<220> FEATURE:
<223> OTHER INFORMATION: CDR sequence

<400> SEQUENCE: 43

Phe His Gly Arg Glu Leu Pro Leu Thr
1               5

<210> SEQ ID NO 44
<211> LENGTH: 10
<212> TYPE: PRT
<213> ORGANISM: Artificial Sequence
<220> FEATURE:
<223> OTHER INFORMATION: CDR sequence

<400> SEQUENCE: 44

Gly Tyr Thr Phe Thr Asn Tyr Tyr Leu Tyr
1               5                   10

<210> SEQ ID NO 45
<211> LENGTH: 17
<212> TYPE: PRT
<213> ORGANISM: Artificial Sequence
<220> FEATURE:
<223> OTHER INFORMATION: CDR sequence

<400> SEQUENCE: 45

Gly Ile Asn Pro Ser Asn Gly Gly Thr Asn Phe Asn Glu Lys Phe Arg
1               5                   10                  15

Gly

<210> SEQ ID NO 46
<211> LENGTH: 11
<212> TYPE: PRT
<213> ORGANISM: Artificial Sequence
<220> FEATURE:
<223> OTHER INFORMATION: CDR sequence

<400> SEQUENCE: 46

Arg Asp Tyr Asn Tyr Asp Gly Gly Phe Asp Tyr
1               5                   10

<210> SEQ ID NO 47
<211> LENGTH: 336
<212> TYPE: DNA
<213> ORGANISM: Artificial Sequence
<220> FEATURE:
<223> OTHER INFORMATION: cDNA encoding VL

<400> SEQUENCE: 47
gacatcgtca tgacacaatc accatctagt ttgtccgcca gcgtcggtga tcgggttacc      60
atcacatgca gagcttccaa atcagtatcc acctccgggt ttaattatat gcactggtac     120
cagcagacac ctggaaaggc acccaaactg ttgatctatt ggcctcaaa cctggactct      180 ggcgtgccag cacgcttcag tgggtcaggt tcaggaactg actttacttt cactatatcc     240
agcctccaag aagaagatat tgcaacatat tattgttttc acggcagaga attgccactg     300
actttcggac agggaaccaa attgcaaatc actagg                               336

<210> SEQ ID NO 48
<211> LENGTH: 112
<212> TYPE: PRT
<213> ORGANISM: Artificial Sequence
<220> FEATURE:
<223> OTHER INFORMATION: VL

<400> SEQUENCE: 48

```
Asp Ile Val Met Thr Gln Ser Pro Ser Leu Ser Ala Ser Val Gly
1               5                   10                  15

Asp Arg Val Thr Ile Thr Cys Arg Ala Ser Lys Ser Val Ser Thr Ser
                20                  25                  30

Gly Phe Asn Tyr Met His Trp Tyr Gln Gln Thr Pro Gly Lys Ala Pro
            35                  40                  45

Lys Leu Leu Ile Tyr Leu Ala Ser Asn Leu Asp Ser Gly Val Pro Ala
        50                  55                  60

Arg Phe Ser Gly Ser Gly Ser Gly Thr Asp Phe Thr Phe Thr Ile Ser
65                  70                  75                  80

Ser Leu Gln Glu Glu Asp Ile Ala Thr Tyr Tyr Cys Phe His Gly Arg
                85                  90                  95

Glu Leu Pro Leu Thr Phe Gly Gly Gly Thr Lys Leu Gln Ile Thr Arg
            100                 105                 110
```

<210> SEQ ID NO 49
<211> LENGTH: 360
<212> TYPE: DNA
<213> ORGANISM: Artificial Sequence
<220> FEATURE:
<223> OTHER INFORMATION: cDNA encoding VH

<400> SEQUENCE: 49

```
caggtacagc tccaacagag cggtgctgag gtaaaaaaac caggttcaag tgttaaagtc      60
tcatgtaagg catctgggta cacattcaca aactactatc tgtactgggt acgccaggct     120
ccaggtcagg gccttgagtg gataggcgga attaacccta gtaatggcgg gaccaacttc     180
aatgaaaaat tcgtgggcg tgtaactatt actgccgacg agagttcaac aaccgcatat     240
atggagttga gttctcttcg ttcagaggat actgctttct attttgtac ccgccgggac     300 tacaattacg atgggggatt cgactattgg gggcagggaa ccaccgtcac agtgagttct     360
```

<210> SEQ ID NO 50
<211> LENGTH: 120
<212> TYPE: PRT
<213> ORGANISM: Artificial Sequence
<220> FEATURE:
<223> OTHER INFORMATION: VH

<400> SEQUENCE: 50

```
Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
                20                  25                  30

Tyr Leu Tyr Trp Val Arg Gln Ala Pro Gly Gln Gly Leu Glu Trp Ile
            35                  40                  45

Gly Gly Ile Asn Pro Ser Asn Gly Gly Thr Asn Phe Asn Glu Lys Phe
        50                  55                  60

Arg Gly Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
```

```
                85                  90                  95
Thr Arg Arg Asp Tyr Asn Tyr Asp Gly Gly Phe Asp Tyr Trp Gly Gln
            100                 105                 110

Gly Thr Thr Val Thr Val Ser Ser
        115                 120

<210> SEQ ID NO 51
<211> LENGTH: 15
<212> TYPE: PRT
<213> ORGANISM: Artificial Sequence
<220> FEATURE:
<223> OTHER INFORMATION: CDR sequence

<400> SEQUENCE: 51

Arg Ala Ser Lys Ser Val Ser Thr Ser Gly Phe Asn Tyr Met His
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: CDR sequence

<400> SEQUENCE: 52

Leu Ala Ser Asn Leu Asp Ser
1               5

<210> SEQ ID NO 53
<211> LENGTH: 9
<212> TYPE: PRT
<213> ORGANISM: Artificial Sequence
<220> FEATURE:
<223> OTHER INFORMATION: CDR sequence

<400> SEQUENCE: 53

Phe His Gly Arg Glu Leu Pro Leu Thr
1               5

<210> SEQ ID NO 54
<211> LENGTH: 10
<212> TYPE: PRT
<213> ORGANISM: Artificial Sequence
<220> FEATURE:
<223> OTHER INFORMATION: CDR sequence

<400> SEQUENCE: 54

Gly Tyr Thr Phe Thr Asn Tyr Tyr Leu Tyr
1               5                   10

<210> SEQ ID NO 55
<211> LENGTH: 17
<212> TYPE: PRT
<213> ORGANISM: Artificial Sequence
<220> FEATURE:
<223> OTHER INFORMATION: CDR sequence

<400> SEQUENCE: 55

Gly Ile Asn Pro Ser Asn Gly Gly Thr Asn Phe Asn Glu Lys Phe Arg
1               5                   10                  15

Gly

<210> SEQ ID NO 56
<211> LENGTH: 11
<212> TYPE: PRT
```

<213> ORGANISM: Artificial Sequence
<220> FEATURE:
<223> OTHER INFORMATION: CDR sequence

<400> SEQUENCE: 56

Arg Asp Tyr Asn Tyr Asp Gly Gly Phe Asp Tyr
1               5                   10

<210> SEQ ID NO 57
<211> LENGTH: 336
<212> TYPE: DNA
<213> ORGANISM: Artificial Sequence
<220> FEATURE:
<223> OTHER INFORMATION: cDNA encoding VL

<400> SEQUENCE: 57

```
gacatcgtca tgacacaatc accatctagt ttgtccgcca gcgtcggtga tcgggttacc      60
atcacatgca gagcttccaa atcagtatcc acctccgggt ttaattatat gcactggtac    120
cagcagacac ctggaaaggc acccaaactg ttgatctatt tggcctcaaa cctggactct    180
ggcgtgccag cacgcttcag tgggtcaggt tcaggaactg actttacttt cactatatcc    240
agcctccaag aagaagatat tgcaacatat tattgttttc acggcagaga attgccactg    300
actttcggac agggaaccaa attgcaaatc actagg                              336
```

<210> SEQ ID NO 58
<211> LENGTH: 112
<212> TYPE: PRT
<213> ORGANISM: Artificial Sequence
<220> FEATURE:
<223> OTHER INFORMATION: VL

<400> SEQUENCE: 58

Asp Ile Val Met Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Phe Asn Tyr Met His Trp Tyr Gln Gln Thr Pro Gly Lys Ala Pro
        35                  40                  45

Lys Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Phe Thr Ile Ser
65                  70                  75                  80

Ser Leu Gln Glu Glu Asp Ile Ala Thr Tyr Tyr Cys Phe His Gly Arg
                85                  90                  95

Glu Leu Pro Leu Thr Phe Gly Gln Gly Thr Lys Leu Gln Ile Thr Arg
            100                 105                 110

<210> SEQ ID NO 59
<211> LENGTH: 360
<212> TYPE: DNA
<213> ORGANISM: Artificial Sequence
<220> FEATURE:
<223> OTHER INFORMATION: cDNA encoding VH

<400> SEQUENCE: 59

```
caagtgcaac tgcagcaaag cggggccgaa gttaaaaagc cagggagcag tgtcaaggta      60
agttgtcgtg cttctggtta taccttcaca aattattatc tttattgggt cgacaggct    120
ccagggcagg gcttgaatg gattggcggg atcaatccaa gtaacggcgg caccaacttt    180
aatgagaagt tcggggtag agtcactatt actgccgacg aatcatcaac aaccgcatac    240
```

-continued

```
atggagctga gttccttgcg atcagaagat accgcttttt attttgcac acgccgcgat        300 tacaattatg atggtggctt tgattattgg gggcaaggaa ctactgtcac agtcagttcc        360
```

<210> SEQ ID NO 60
<211> LENGTH: 120
<212> TYPE: PRT
<213> ORGANISM: Artificial Sequence
<220> FEATURE:
<223> OTHER INFORMATION: VH

<400> SEQUENCE: 60

Gln Val Gln Leu Gln Gln Ser Gly Ala Glu Val Lys Lys Pro Gly Ser
1               5                   10                  15

Ser Val Lys Val Ser Cys Arg Ala Ser Gly Tyr Thr Phe Thr Asn Tyr
            20                  25                  30

Tyr Leu Tyr Trp Val Arg Gln Ala Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Arg Gly Arg Val Thr Ile Thr Ala Asp Glu Ser Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Arg Asp Tyr Asn Tyr Asp Gly Gly Phe Asp Tyr Trp Gly Gln
            100                 105                 110

Gly Thr Thr Val Thr Val Ser Ser
        115                 120

<210> SEQ ID NO 61
<211> LENGTH: 15
<212> TYPE: PRT
<213> ORGANISM: Artificial Sequence
<220> FEATURE:
<223> OTHER INFORMATION: CDR sequence

<400> SEQUENCE: 61

Arg Ala Ser Lys Ser Val Ser Thr Ser Gly Phe Asn Tyr Met His
1               5                   10                  15

<210> SEQ ID NO 62
<211> LENGTH: 7
<212> TYPE: PRT
<213> ORGANISM: Artificial Sequence
<220> FEATURE:
<223> OTHER INFORMATION: CDR sequence

<400> SEQUENCE: 62

Leu Ala Ser Asn Leu Asp Ser
1               5

<210> SEQ ID NO 63
<211> LENGTH: 9
<212> TYPE: PRT
<213> ORGANISM: Artificial Sequence
<220> FEATURE:
<223> OTHER INFORMATION: CDR sequence

<400> SEQUENCE: 63

Phe His Gly Arg Glu Leu Pro Leu Thr
1               5

```
<210> SEQ ID NO 64
<211> LENGTH: 10
<212> TYPE: PRT
<213> ORGANISM: Artificial Sequence
<220> FEATURE:
<223> OTHER INFORMATION: CDR sequence

<400> SEQUENCE: 64

Gly Tyr Thr Phe Thr Asn Tyr Tyr Leu Tyr
1               5                   10

<210> SEQ ID NO 65
<211> LENGTH: 17
<212> TYPE: PRT
<213> ORGANISM: Artificial Sequence
<220> FEATURE:
<223> OTHER INFORMATION: CDR sequence

<400> SEQUENCE: 65

Gly Ile Asn Pro Ser Asn Gly Gly Thr Asn Phe Asn Glu Lys Phe Arg
1               5                   10                  15

Gly

<210> SEQ ID NO 66
<211> LENGTH: 11
<212> TYPE: PRT
<213> ORGANISM: Artificial Sequence
<220> FEATURE:
<223> OTHER INFORMATION: CDR sequence

<400> SEQUENCE: 66

Arg Asp Tyr Asn Tyr Asp Gly Gly Phe Asp Tyr
1               5                   10

<210> SEQ ID NO 67
<211> LENGTH: 333
<212> TYPE: DNA
<213> ORGANISM: Artificial Sequence
<220> FEATURE:
<223> OTHER INFORMATION: cDNA encoding VL

<400> SEQUENCE: 67
gacattgtaa tgactcaaag tcctgactcc cttgccgtta gtctggggga gcgggcaacc     60
ataaattgtc gcgcctcaaa gagtgtgagc acatccggct caactatat gcattggtac    120 caacagaaac caggacaacc tcctaaattg ctgatatatc ttgcatctaa tctcgattca    180
ggcgtgcctg atcgtttctc aggcagcgga agcgggactg atttcactct gactatccgc    240
cctttgcaag ccgaggacgt tgctgtttac tattgtcaac atggccgcga acttccactt    300
actttcggcc aaggcacaaa gctggagatc aag                                 333

<210> SEQ ID NO 68
<211> LENGTH: 111
<212> TYPE: PRT
<213> ORGANISM: Artificial Sequence
<220> FEATURE:
<223> OTHER INFORMATION: VL

<400> SEQUENCE: 68

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Phe Asn Tyr Met His Trp Tyr Gln Gln Lys Pro Gly Gln Pro Pro
```

```
                35                  40                  45
Lys Leu Leu Ile Tyr Leu Ala Ser Asn Leu Asp Ser Gly Val Pro Asp
 50                  55                  60

Arg Phe Ser Gly Ser Gly Ser Gly Thr Asp Phe Thr Leu Thr Ile Arg
 65                  70                  75                  80

Pro Leu Gln Ala Glu Asp Val Ala Val Tyr Tyr Cys Gln His Gly Arg
                 85                  90                  95

Glu Leu Pro Leu Thr Phe Gly Gln Gly Thr Lys Leu Glu Ile Lys
            100                 105                 110
```

<210> SEQ ID NO 69
<211> LENGTH: 360
<212> TYPE: DNA
<213> ORGANISM: Artificial Sequence
<220> FEATURE:
<223> OTHER INFORMATION: cDNA encoding VH

<400> SEQUENCE: 69

```
gaggttcagt tgcaagaaag tggagcagag gtgaagaagc ctggttcttc cgtgaaggtt      60
agttgtaaag catccggcta tactttact aactactacc tgtactgggt acgacaagca      120
cctgggcaag gcctggaatg gatgggcgga attaaccca gcaacggagg cacaaacttt      180
aatgaaaaat tccgtggccg tgtgaccatt accgctgacg aatctaccag tacagcatat      240
atggaattga gctctctgcg tagtgaagat acagctgtct attattgtgc ccgaagagac      300
tataattatg atggaggctt cgattactgg ggtcaaggga caacagtgac cgtgtcttca      360
```

<210> SEQ ID NO 70
<211> LENGTH: 120
<212> TYPE: PRT
<213> ORGANISM: Artificial Sequence
<220> FEATURE:
<223> OTHER INFORMATION: VH

<400> SEQUENCE: 70

```
Glu Val Gln Leu Gln Glu Ser Gly Ala Glu Val Lys Lys Pro Gly Ser
 1               5                  10                  15

Ser Val Lys Val Ser Cys Lys Ala Ser Gly Tyr Thr Phe Thr Asn Tyr
             20                  25                  30

Tyr Leu Tyr Trp Val Arg Gln Ala Pro Gly Gln Gly Leu Glu Trp Met
         35                  40                  45

Gly Gly Ile Asn Pro Ser Asn Gly Gly Thr Asn Phe Asn Glu Lys Phe
 50                  55                  60

Arg Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Asp Tyr Asn Tyr Asp Gly Gly Phe Asp Tyr Trp Gly Gln
            100                 105                 110

Gly Thr Thr Val Thr Val Ser Ser
            115                 120
```

<210> SEQ ID NO 71
<211> LENGTH: 15
<212> TYPE: PRT
<213> ORGANISM: Artificial Sequence
<220> FEATURE:
<223> OTHER INFORMATION: CDR sequence

<400> SEQUENCE: 71

```
Arg Ala Ser Lys Ser Val Ser Thr Ser Gly Phe Asn Tyr Met His
1               5                   10                  15
```

<210> SEQ ID NO 72
<211> LENGTH: 7
<212> TYPE: PRT
<213> ORGANISM: Artificial Sequence
<220> FEATURE:
<223> OTHER INFORMATION: CDR sequence

<400> SEQUENCE: 72

```
Leu Ala Ser Asn Leu Asp Ser
1               5
```

<210> SEQ ID NO 73
<211> LENGTH: 9
<212> TYPE: PRT
<213> ORGANISM: Artificial Sequence
<220> FEATURE:
<223> OTHER INFORMATION: CDR sequence

<400> SEQUENCE: 73

```
Gln His Gly Arg Glu Leu Pro Leu Thr
1               5
```

<210> SEQ ID NO 74
<211> LENGTH: 10
<212> TYPE: PRT
<213> ORGANISM: Artificial Sequence
<220> FEATURE:
<223> OTHER INFORMATION: CDR sequence

<400> SEQUENCE: 74

```
Gly Tyr Thr Phe Thr Asn Tyr Tyr Leu Tyr
1               5                   10
```

<210> SEQ ID NO 75
<211> LENGTH: 17
<212> TYPE: PRT
<213> ORGANISM: Artificial Sequence
<220> FEATURE:
<223> OTHER INFORMATION: CDR sequence

<400> SEQUENCE: 75

```
Gly Ile Asn Pro Ser Asn Gly Gly Thr Asn Phe Asn Glu Lys Phe Arg
1               5                   10                  15

Gly
```

<210> SEQ ID NO 76
<211> LENGTH: 11
<212> TYPE: PRT
<213> ORGANISM: Artificial Sequence
<220> FEATURE:
<223> OTHER INFORMATION: CDR sequence

<400> SEQUENCE: 76

```
Arg Asp Tyr Asn Tyr Asp Gly Gly Phe Asp Tyr
1               5                   10
```

<210> SEQ ID NO 77
<211> LENGTH: 287
<212> TYPE: PRT
<213> ORGANISM: Homo sapiens

<400> SEQUENCE: 77

Met Gln Ile Pro Gln Ala Pro Trp Pro Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro
            275                 280                 285

<210> SEQ ID NO 78
<211> LENGTH: 20
<212> TYPE: PRT
<213> ORGANISM: Mus musculus

<400> SEQUENCE: 78

Met Glu Thr Asp Thr Leu Leu Leu Trp Val Leu Leu Leu Trp Val Pro
1               5                   10                  15

Gly Ser Thr Gly
            20

<210> SEQ ID NO 79

```
<211> LENGTH: 19
<212> TYPE: PRT
<213> ORGANISM: Mus musculus

<400> SEQUENCE: 79

Met Gly Cys Ser Trp Val Met Leu Phe Leu Val Ala Thr Ala Thr Gly
1               5                   10                  15

Val His Ser
```

ANTI-PD-1 ANTIBODIES AND USES THEREOF

CLAIM OF PRIORITY

This application is a National Stage Application under 35 U.S.C. § 371 and claims the benefit of International Application No. PCT/US2020/028773, filed Apr. 17, 2020, which claims the benefit of U.S. Provisional Application No. 62/836,177, filed on Apr. 19, 2019. The entire contents of the foregoing are incorporated herein by reference.

TECHNICAL FIELD

This disclosure relates to anti-PD-1 (Programmed Cell Death 1) antibodies, antigen-binding fragments, and the uses thereof.

BACKGROUND

The protein Programmed Death 1 (PD-1 or PDCD1) is an inhibitory member of the CD28 family of receptors, which also includes CD28, CTLA-4, ICOS and BTLA. PD-1 is expressed on activated B cells, T cells, and myeloid cells (Agata et al., supra; Okazaki et al. (2002) Curr. Opin. Immunol. 14: 391779-82; Bennett et al. (2003) J Immunol 1 70:711-8). The PD-1 gene is a 55 kDa type I transmembrane protein that is part of the Ig gene superfamily (Agata et al. (1996) Int Immunol 8:765-72). PD-1 contains a membrane proximal immunoreceptor tyrosine inhibitory motif (ITIM) and a membrane distal tyrosine-based switch motif (ITSM) (Thomas, M. L. (1995) J Exp Med 181:1953-6; Vivier, E and Daeron, M (1997) Immunol Today 18:286-91). Although structurally similar to CTLA-4, PD-1 lacks the MYPPY motif that is critical for B7-1 and B7-2 binding.

T-cells receive both positive and negative secondary co-stimulatory signals. The regulation of such positive and negative signals is critical to maximize the host's protective immune responses while maintaining immune tolerance and preventing autoimmunity. Negative secondary signals seem necessary for induction of T-cell tolerance, while positive signals promote T-cell activation. While the simple two-signal model provides a valid explanation for naive lymphocytes, a host's immune response is a dynamic process, and co-stimulatory signals can also be provided to antigen-exposed T-cells. PD-1 is an inhibitory member of the CD28 family expressed on activated B cells, T cells, and myeloid cells (Agata et al., supra; Okazaki et al. (2002) Curr Opin Immunol 14: 391779-82; Bennett et al. (2003) J Immunol 1 70:711-8) and provides negative signals.

Two ligands for PD-1 have been identified, PD-L1 and PD-L2. They have been shown to downregulate T cell activation upon binding to PD-1 (Freeman et al. (2000) J Exp Med 192: 1027-34; Latchman et al. (2001) Nat Immunol 2:261-8; Carter et al. (2002) Eur J Immunol 32:634-43). Both PD-L1 and PD-L2 are B7 homologs that bind to PD-1, but do not bind to other CD28 family members. PD-L1 is abundant in a variety of human cancers (Dong et al. (2002) Nat. Med. 8:787-9). The interaction between PD-1 and PD-L1 results in a decrease in tumor infiltrating lymphocytes, a decrease in T-cell receptor-mediated proliferation, and immune evasion by the cancerous cells (Dong et al. (2003) J. Mal. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well (Iwai et al. (2002) Proc. Nat'l. Acad. Sci. USA 99:12293-7; Brown et al. (2003) J. Immunol. 170: 1257-66).

There exists a need in the field for antibodies or antigen-binding portions thereof, including chimeric and humanized antibodies, that neutralize/block PD-1 negative signal and stimulate an immune response, and that can have applications in the treatment of cancer and many other diseases.

SUMMARY

The present disclosure provides monoclonal antibodies, or antigen-binding portions thereof that specifically bind to and neutralizes human PD-1. Monoclonal antibodies that are developed in mice can be immunogenic in humans. The present disclosure also provides humanized antibodies that were redesigned from the mouse antibody to reduce the immunogenicity in humans. These antibodies have improved efficacy and safety in humans.

In one aspect, provided herein is an antibody or antigen-binding fragment thereof that binds to PD-1 (Programed Cell Death Protein 1) comprising a heavy chain variable region (VH) comprising complementarity determining regions (CDRs) 1, 2, and 3. In some embodiments, the VH CDR1 region comprises an amino acid sequence that is at least 80% identical to a selected VH CDR1 amino acid sequence, the VH CDR2 region comprises an amino acid sequence that is at least 80% identical to a selected VH CDR2 amino acid sequence, and the VH CDR3 region comprises an amino acid sequence that is at least 80% identical to a selected VH CDR3 amino acid sequence; and a light chain variable region (VL) comprising CDRs 1, 2, and 3. In some embodiments, the VL CDR1 region comprises an amino acid sequence that is at least 80% identical to a selected VL CDR1 amino acid sequence, the VL CDR2 region comprises an amino acid sequence that is at least 80% identical to a selected VL CDR2 amino acid sequence, and the VL CDR3 region comprises an amino acid sequence that is at least 80% identical to a selected VL CDR3 amino acid sequence.

In some embodiments, the selected VH CDRs 1, 2, and 3 amino acid sequences and the selected VL CDRs, 1, 2, and 3 amino acid sequences are one of the following:
(1) the selected VH CDRs 1, 2, 3 amino acid sequences are set forth in SEQ ID NOs: 8, 9, 10, respectively, and the selected VL CDRs 1, 2, 3 amino acid sequences are set forth in SEQ ID NOs: 5, 6, 7, respectively;
(2) the selected VH CDRs 1, 2, 3 amino acid sequences are set forth in SEQ ID NOs: 22, 23, 24, respectively, and the selected VL CDRs 1, 2, 3 amino acid sequences are set forth in SEQ ID NOs: 19, 20, 21, respectively;
(3) the selected VH CDRs 1, 2, 3 amino acid sequences are set forth in SEQ ID NOs: 74, 75, 76, respectively, and the selected VL CDRs 1, 2, 3 amino acid sequences are set forth in SEQ ID NOs: 71, 72, 73, respectively;
(4) the selected VH CDRs 1, 2, 3 amino acid sequences are set forth in SEQ ID NOs: 34, 35, 36, respectively, and the selected VL CDRs 1, 2, 3 amino acid sequences are set forth in SEQ ID NOs: 31, 32, 33, respectively;
(5) the selected VH CDRs 1, 2, 3 amino acid sequences are set forth in SEQ ID NOs: 54, 55, 56, respectively, and the selected VL CDRs 1, 2, 3 amino acid sequences are set forth in SEQ ID NOs: 51, 52, 53, respectively;
(6) the selected VH CDRs 1, 2, 3 amino acid sequences are set forth in SEQ ID NOs: 64, 65, 66, respectively, and the selected VL CDRs 1, 2, 3 amino acid sequences are set forth in SEQ ID NOs: 61, 62, 63, respectively;

(7) the selected VH CDRs 1, 2, 3 amino acid sequences are set forth in SEQ ID NOs: 44, 45, 46, respectively, and the selected VL CDRs 1, 2, 3 amino acid sequences are set forth in SEQ ID NOs: 41, 42, 43, respectively.

In some embodiments, the VH comprises CDRs 1, 2, 3 with the amino acid sequences set forth in SEQ ID NOs: 8, 9, and 10, respectively, and the VL comprises CDRs 1, 2, 3 with the amino acid sequences set forth in SEQ ID NOs: 5, 6, and 7, respectively.

In some embodiments, the VH comprises CDRs 1, 2, 3 with the amino acid sequences set forth in SEQ ID NOs: 22, 23, and 24, respectively, and the VL comprises CDRs 1, 2, 3 with the amino acid sequences set forth in SEQ ID NOs: 19, 20, and 21, respectively.

In some embodiments, the VH comprises CDRs 1, 2, 3 with the amino acid sequences set forth in SEQ ID NOs: 74, 75, and 76, respectively, and the VL comprises CDRs 1, 2, 3 with the amino acid sequences set forth in SEQ ID NOs: 71, 72, and 73, respectively.

In some embodiments, the VH comprises CDRs 1, 2, 3 with the amino acid sequences set forth in SEQ ID NOs: 34, 35, and 36, respectively, and the VL comprises CDRs 1, 2, 3 with the amino acid sequences set forth in SEQ ID NOs: 31, 32, and 33, respectively.

In some embodiments, the antibody or antigen-binding fragment specifically binds to human PD-1.

In some embodiments, the antibody or antigen-binding fragment is a humanized antibody or antigen-binding fragment thereof.

In some embodiments, the antibody or antigen-binding fragment is a single-chain variable fragment (scFv).

In one aspect, provided herein is a nucleic acid comprising a polynucleotide encoding a polypeptide comprising:

(1) an immunoglobulin heavy chain or a fragment thereof comprising a heavy chain variable region (VH) comprising complementarity determining regions (CDRs) 1, 2, and 3 comprising the amino acid sequences set forth in SEQ ID NOs: 8, 9, and 10, respectively, and in some embodiments, the VH, when paired with a light chain variable region (VL) comprising the amino acid sequence set forth in SEQ ID NO: 2, 16, 28, 38, 48, 58 or 68 binds to PD-1;

(2) an immunoglobulin light chain or a fragment thereof comprising a VL comprising CDRs 1, 2, and 3 comprising the amino acid sequences set forth in SEQ ID NOs: 5, 6, and 7, respectively, and in some embodiments, the VL, when paired with a VH comprising the amino acid sequence set forth in SEQ ID NO: 4, 18, 30, 40, 50, 60, or 70 binds to PD-1;

(3) an immunoglobulin heavy chain or a fragment thereof comprising a heavy chain variable region (VH) comprising CDRs 1, 2, and 3 comprising the amino acid sequences set forth in SEQ ID NOs: 22, 23, and 24, respectively, and in some embodiments, the VH, when paired with a light chain variable region (VL) comprising the amino acid sequence set forth in SEQ ID NO: 2, 16, 28, 38, 48, 58 or 68 binds to PD-1;

(4) an immunoglobulin light chain or a fragment thereof comprising a VL comprising CDRs 1, 2, and 3 comprising the amino acid sequences set forth in SEQ ID NOs: 19, 20, and 21, respectively, and in some embodiments, the VL, when paired with a VH comprising the amino acid sequence set forth in SEQ ID NO: 4, 18, 30, 40, 50, 60, or 70 binds to PD-1;

(5) an immunoglobulin heavy chain or a fragment thereof comprising a heavy chain variable region (VH) comprising CDRs 1, 2, and 3 comprising the amino acid sequences set forth in SEQ ID NOs: 74, 75, and 76, respectively, and in some embodiments, the VH, when paired with a light chain variable region (VL) comprising the amino acid sequence set forth in SEQ ID NO: 2, 16, 28, 38, 48, 58 or 68 binds to PD-1;

(6) an immunoglobulin light chain or a fragment thereof comprising a VL comprising CDRs 1, 2, and 3 comprising the amino acid sequences set forth in SEQ ID NOs: 71, 72, and 73, respectively, and in some embodiments, the VL, when paired with a VH comprising the amino acid sequence set forth in SEQ ID NO: 4, 18, 30, 40, 50, 60, or 70 binds to PD-1;

(7) an immunoglobulin heavy chain or a fragment thereof comprising a VH comprising CDRs 1, 2, and 3 comprising the amino acid sequences set forth in SEQ ID NOs: 34, 35, and 36, respectively, and in some embodiments, the VH, when paired with a VL comprising the amino acid sequence set forth in SEQ ID NO: 2, 16, 28, 38, 48, 58 or 68 binds to PD-1;

(8) an immunoglobulin light chain or a fragment thereof comprising a VL comprising CDRs 1, 2, and 3 comprising the amino acid sequences set forth in SEQ ID NOs: 31, 32, and 33, respectively, and in some embodiments, the VL, when paired with a VH comprising the amino acid sequence set forth in SEQ ID NO: 4, 18, 30, 40, 50, 60, or 70 binds to PD-1;

(9) an immunoglobulin heavy chain or a fragment thereof comprising a VH comprising CDRs 1, 2, and 3 comprising the amino acid sequences set forth in SEQ ID NOs: 54, 55, and 56, respectively, and in some embodiments, the VH, when paired with a VL comprising the amino acid sequence set forth in SEQ ID NO: 2, 16, 28, 38, 48, 58 or 68 binds to PD-1;

(10) an immunoglobulin light chain or a fragment thereof comprising a VL comprising CDRs 1, 2, and 3 comprising the amino acid sequences set forth in SEQ ID NOs: 51, 52, and 53, respectively, and in some embodiments, the VL, when paired with a VH comprising the amino acid sequence set forth in SEQ ID NO: 4, 18, 30, 40, 50, 60, or 70 binds to PD-1;

(11) an immunoglobulin heavy chain or a fragment thereof comprising a VH comprising CDRs 1, 2, and 3 comprising the amino acid sequences set forth in SEQ ID NOs: 64, 65, and 66, respectively, and in some embodiments, the VH, when paired with a VL comprising the amino acid sequence set forth in SEQ ID NO: 2, 16, 28, 38, 48, 58 or 68 binds to PD-1;

(12) an immunoglobulin light chain or a fragment thereof comprising a VL comprising CDRs 1, 2, and 3 comprising the amino acid sequences set forth in SEQ ID NOs: 61, 62, and 63, respectively, and in some embodiments, the VL, when paired with a VH comprising the amino acid sequence set forth in SEQ ID NO: 4, 18, 30, 40, 50, 60, or 70 binds to PD-1;

(13) an immunoglobulin heavy chain or a fragment thereof comprising a VH comprising CDRs 1, 2, and 3 comprising the amino acid sequences set forth in SEQ ID NOs: 44, 45, and 46, respectively, and in some embodiments, the VH, when paired with a VL comprising the amino acid sequence set forth in SEQ ID NO: 2, 16, 28, 38, 48, 58 or 68 binds to PD-1;

(14) an immunoglobulin light chain or a fragment thereof comprising a VL comprising CDRs 1, 2, and 3 comprising the amino acid sequences set forth in SEQ ID NOs: 41, 42, and 43, respectively, and in some embodiments, the VL, when paired with a VH comprising the amino acid sequence set forth in SEQ ID NO: 4, 18, 30, 40, 50, 60, or 70 binds to PD-1.

In some embodiments, the nucleic acid comprises a polynucleotide encoding a polypeptide comprising an immunoglobulin heavy chain or a fragment thereof comprising a VH comprising CDRs 1, 2, and 3 comprising the amino acid sequences set forth in SEQ ID NOs: 8, 9, and 10, respectively.

In some embodiments, the nucleic acid comprises a polynucleotide encoding a polypeptide comprising an immunoglobulin light chain or a fragment thereof comprising a VL comprising CDRs 1, 2, and 3 comprising the amino acid sequences set forth in SEQ ID NOs: 5, 6, and 7, respectively.

In some embodiments, the nucleic acid comprises a polynucleotide encoding a polypeptide comprising an immunoglobulin heavy chain or a fragment thereof comprising a VH comprising CDRs 1, 2, and 3 comprising the amino acid sequences set forth in SEQ ID NOs: 22, 23, and 24, respectively.

In some embodiments, the nucleic acid comprises a polynucleotide encoding a polypeptide comprising an immunoglobulin light chain or a fragment thereof comprising a VL comprising CDRs 1, 2, and 3 comprising the amino acid sequences set forth in SEQ ID NOs: 19, 20, and 21, respectively.

In some embodiments, the nucleic acid comprises a polynucleotide encoding a polypeptide comprising an immunoglobulin heavy chain or a fragment thereof comprising a VH comprising CDRs 1, 2, and 3 comprising the amino acid sequences set forth in SEQ ID NOs: 74, 75, and 76, respectively.

In some embodiments, the nucleic acid comprises a polynucleotide encoding a polypeptide comprising an immunoglobulin light chain or a fragment thereof comprising a VL comprising CDRs 1, 2, and 3 comprising the amino acid sequences set forth in SEQ ID NOs: 71, 72, and 73, respectively.

In some embodiments, the nucleic acid comprises a polynucleotide encoding a polypeptide comprising an immunoglobulin heavy chain or a fragment thereof comprising a VH comprising CDRs 1, 2, and 3 comprising the amino acid sequences set forth in SEQ ID NOs: 34, 35, and 36, respectively.

In some embodiments, the nucleic acid comprises a polynucleotide encoding a polypeptide comprising an immunoglobulin light chain or a fragment thereof comprising a VL comprising CDRs 1, 2, and 3 comprising the amino acid sequences set forth in SEQ ID NOs: 31, 32, and 33, respectively.

In some embodiments, the VH when paired with a VL specifically binds to human PD-1, or the VL when paired with a VH specifically binds to human PD-1.

In some embodiments, the immunoglobulin heavy chain or the fragment thereof is a humanized immunoglobulin heavy chain or a fragment thereof, and the immunoglobulin light chain or the fragment thereof is a humanized immunoglobulin light chain or a fragment thereof.

In some embodiments, the nucleic acid encodes a single-chain variable fragment (scFv).

In some embodiments, the nucleic acid is cDNA.

In one aspect, provided herein is a vector comprising one or more of the nucleic acids as described herein.

In one aspect, provided herein is a vector comprising two of the nucleic acids as described herein. In some embodiments, the vector encodes the VL region and the VH region that together bind to PD-1.

In one aspect, provided herein is a pair of vectors. In some embodiments, each vector comprises one of the nucleic acids as described herein. In some embodiments, together the pair of vectors encodes the VL region and the VH region that together bind to PD-1.

In one aspect, provided herein is a cell comprising the vector as described herein, or the pair of vectors as described herein.

In some embodiments, the cell is a CHO cell.

In one aspect, provided herein is a cell comprising one or more of the nucleic acids as described herein.

In one aspect, provided herein a cell comprising two of the nucleic acids as described herein.

In some embodiments, the two nucleic acids together encode the VL region and the VH region that together bind to PD-1.

In one aspect, provided herein is a method of producing an antibody or an antigen-binding fragment thereof, the method comprising (a) culturing the cell as described herein under conditions sufficient for the cell to produce the antibody or the antigen-binding fragment; and (b) collecting the antibody or the antigen-binding fragment produced by the cell.

In one aspect, provided herein is an antibody or antigen-binding fragment thereof that binds to PD-1 comprising a heavy chain variable region (VH) comprising an amino acid sequence that is at least 90% identical to a selected VH sequence, and a light chain variable region (VL) comprising an amino acid sequence that is at least 90% identical to a selected VL sequence. In some embodiments, the selected VH sequence is selected from SEQ ID NO: 4, 18, 30, 40, 50, 60, or 70, and the selected VL sequence is selected from SEQ ID NO: 2, 16, 28, 38, 48, 58 or 68.

In some embodiments, the VH comprises the sequence of SEQ ID NO: 4 and the VL comprises the sequence of SEQ ID NO: 2.

In some embodiments, the VH comprises the sequence of SEQ ID NO: 18 and the VL comprises the sequence of SEQ ID NO: 16.

In some embodiments, the VH comprises the sequence of SEQ ID NO: 70 and the VL comprises the sequence of SEQ ID NO: 68.

In some embodiments, the VH comprises the sequence of SEQ ID NO: 30 and the VL comprises the sequence of SEQ ID NO: 28.

In some embodiments, the VH comprises the sequence of SEQ ID NO: 50 and the VL comprises the sequence of SEQ ID NO: 48.

In some embodiments, the VH comprises the sequence of SEQ ID NO: 60 and the VL comprises the sequence of SEQ ID NO: 58.

In some embodiments, the VH comprises the sequence of SEQ ID NO: 40 and the VL comprises the sequence of SEQ ID NO: 38.

In some embodiments, the antibody or antigen-binding fragment specifically binds to human PD-1.

In some embodiments, the antibody or antigen-binding fragment is a humanized antibody or antigen-binding fragment thereof.

In some embodiments, the antibody or antigen-binding fragment is a single-chain variable fragment (scFv).

In one aspect, provided herein is an antibody or antigen-binding fragment thereof comprising the VH CDRs 1, 2, 3, and the VL CDRs 1, 2, 3 of the antibody or antigen-binding fragment thereof as described herein.

In one aspect, provided herein is an antibody-drug conjugate comprising the antibody or antigen-binding fragment thereof as described herein covalently bound to a therapeutic agent.

In some embodiments, the therapeutic agent is a cytotoxic or cytostatic agent.

In one aspect, provided herein is a method of treating a subject having cancer, the method comprising administering a therapeutically effective amount of a composition comprising the antibody or antigen-binding fragment thereof as described herein, or the antibody-drug conjugate as described herein, to the subject.

In some embodiments, the subject has a solid tumor or a hematologic cancer (e.g., lymphoma).

In some embodiments, the cancer is melanoma, non-small cell lung cancer, head and neck squamous cell carcinoma, relapsed or refractory classical Hodgkin lymphoma, squamous cell lung cancer, renal cell carcinoma, or cutaneous squamous cell carcinoma.

In some embodiments, the cancer is urothelial carcinoma, merkel-cell carcinoma, or mesothelioma.

In one aspect, provided herein is a method of decreasing the rate of tumor growth, the method comprising contacting an immune cell with an effective amount of a composition comprising an antibody or antigen-binding fragment thereof as described herein, or the antibody-drug conjugate as described herein, to the subject.

In one aspect, provided herein is a method of killing a tumor cell, the method comprising contacting an immune cell with an effective amount of a composition comprising the antibody or antigen-binding fragment thereof as described herein, or the antibody-drug conjugate as described herein, to the subject.

In one aspect, provided herein is a method of treating or reducing the risk of developing an infectious disease, the method comprising administering a therapeutically effective amount of a composition comprising the antibody or antigen-binding fragment thereof as described herein to the subject.

In some embodiments, provided herein is the method that further comprises administering a vaccine to the subject.

In one aspect, provided herein is a pharmaceutical composition comprising the antibody or antigen-binding fragment thereof as described herein, and a pharmaceutically acceptable carrier.

In one aspect, provided herein is a pharmaceutical composition comprising the antibody drug conjugate as described herein, and a pharmaceutically acceptable carrier.

In some embodiments, the antibody is an IgG1, IgG2, or IgG4 antibody. In some embodiments, the antibody is a human IgG1 antibody.

In an aspect, an isolated monoclonal antibody, or antigen-binding portion thereof comprises: (a) a light chain variable domain CDR1 comprising SEQ ID NO:5; (b) a light chain variable domain CDR2 comprising SEQ ID NO:6; and (c) a light chain variable domain CDR3 comprising SEQ ID NO:7; (d) a heavy chain variable domain CDR1 comprising SEQ ID NO:8; (e) a heavy chain variable domain CDR2 comprising SEQ ID NO:9; (0 a heavy chain variable domain CDR3 comprising SEQ ID NO:10.

In an aspect, the monoclonal antibody, or antigen-binding portion thereof blocks the interaction of PD-1 with both PD-L1 and PD-L2. Therefore the antibody, or antigen-binding portion can stimulate an anti-tumor immune response.

In yet another aspect, the disclosure further provides a monoclonal antibody, or an antigen-binding portion thereof, which comprises: a light chain variable domain comprising SEQ ID NO:2 and a heavy chain variable domain comprising SEQ ID NO:4.

The antibodies of the disclosure can be further engineered into formats suitable for human therapeutics by modifications that minimize immunogenicity. Suitable antibodies include, but are not limited to chimeric antibodies and humanized antibodies. The affinity, stability and specificity of the disclosed antibodies can also be further optimized by techniques known to one of skill in the art. Other formats can involve oligomerization, drug conjugation and fusion of the disclosed antibodies with other functional proteins.

In yet another aspect, the humanized monoclonal antibody, or antigen-binding portion thereof, comprises a light chain variable domain amino acid sequence has at least 95% identity to SEQ ID NO:2 and a heavy chain variable domain amino acid sequence has at least 95% identity to SEQ ID NO:4.

In yet another aspect, the disclosure further provides an isolated monoclonal antibody, or antigen-binding portion thereof comprising (a) a light chain variable domain CDR1 comprising SEQ ID NO: 5; (b) a light chain variable domain CDR2 comprising SEQ ID NO:6; (c) a light chain variable domain CDR3 comprising SEQ ID NO:7; and a heavy chain variable domain amino acid sequence with at least 95% identity to SEQ ID NO:4.

In yet another aspect, the disclosure further provides an isolated monoclonal antibody, or antigen-binding portion thereof comprising (a) a heavy chain variable domain CDR1 comprising SEQ ID NO:8; (b) a heavy chain variable domain CDR2 comprising SEQ ID NO:9; (c) a heavy chain variable domain CDR3 comprising SEQ ID NO:10 and a light chain variable domain amino acid sequence with at least 95% identity to SEQ ID NO:2.

The antibodies of the disclosure can be, for example, full-length antibodies, for example of an IgG1, IgG2, IgG3, or IgG4 isotype. Alternatively, the disclosed antibodies can be antibody fragments, such as Fab, Fab' and F(ab')2 fragments, diabody, triabody, tetrabody, single-chain variable region fragment (scFv), disulfide-stabilized variable region fragment (dsFv), and half antibodies. Alternatively, the disclosed antibodies can be bispecific antibodies.

In another aspect of the disclosure, an isolated monoclonal antibody or an antigen-binding portion thereof comprises: a light chain comprising SEQ ID NO:11 and a heavy chain comprising SEQ ID NO:12. In a preferred embodiment, the isolated monoclonal antibody comprises a light chain with the amino acid sequence of SEQ ID NO:13 and a heavy chain with the amino acid sequence of SEQ ID NO:14.

In another aspect of the disclosure, a pharmaceutical composition comprising isolated monoclonal antibody, or antigen-binding portion thereof and a pharmaceutically acceptable carrier are also provided. Compositions comprising an immunoconjugate of the disclosure and a pharmaceutically acceptable carrier are also provided.

In another aspect of the disclosure, an isolated nucleic acid molecule encoding the antibody, or antigen-binding portion thereof, and a host cell comprising a sequence of the nucleic acid molecule encoding the antibody, or antigen-binding portion thereof is also provided. In a preferred embodiment, the isolated nucleic acid molecule further comprises a sequence encoding a signal peptide. In a preferred embodiment, an isolated nucleic acid molecule encoding the antibody, or antigen-binding portion thereof, comprises the nucleic acid sequence of SEQ ID NO:1 and/or SEQ ID NO:3. In a preferred embodiment, the host cell is a hybridoma cell.

The present disclosure further provides a method of stimulating immune responses using the anti-PD-1 antibodies of the disclosure. For example, in one embodiment, the disclosure provides a method for treating a subject in need thereof, comprising the step of administering to the subject an effective amount of the antibody or antigen-binding portion as described herein.

In another aspect, the disclosure provides a method for treating cancer in a human comprising the step of administering to the human the antibody or antigen-binding portion as described herein in an amount effective to treat said cancer.

In another aspect, the disclosure provides a method for treating infectious diseases in a human comprising the step of administering to the human the antibody or antigen-binding portion as described herein in an amount effective to treat said infectious diseases.

In one aspect, the antibody or portion specifically binds to human PD-1 blocks the interaction between PD-1 and PD-L1.

In one aspect, provided herein is a pharmaceutical composition comprising the antibody, or antigen-binding portion thereof as described herein and a pharmaceutically acceptable carrier.

In one aspect, provided herein is a method of stimulating immune responses in a subject, comprising the step of administering to the subject the pharmaceutical composition as described herein in an amount effective to stimulate immune response in said subject.

In one aspect, provided herein is a method of treating an infectious disease in a subject, comprising the step of administering to the subject the pharmaceutical composition as described herein in an amount effective to treat said infectious disease.

In one aspect, provided herein is a method of treating cancer in a subject, comprising the step of administering to the subject the pharmaceutical composition as described herein in an amount effective to treat said cancer.

In some embodiments, the monoclonal antibody, or antigen-binding portion thereof as described herein is a Fab fragment, an F(ab')2 fragment, an Fv fragment, a single chain antibody, or a bispecific antibody.

In some embodiments, the monoclonal antibody as described herein is a chimeric antibody or humanized antibody.

In some embodiments, the monoclonal antibody as described herein is an immunoglobulin G (IgG), an IgM, an IgE, an IgA or an IgD molecule, or a derivative thereof In some embodiments, the monoclonal antibody described herein is an IgG1, IgG2, IgG3, or IgG4, or a derivative thereof.

In some embodiments, the monoclonal antibody, or antigen-binding portion thereof as described herein blocks the interaction between PD-1 and PD-L2.

In one aspect, provided herein is a monoclonal antibody comprising a light chain variable domain comprising the amino acid sequence of SEQ ID NO:2 and a heavy chain variable domain comprising the amino acid sequence of SEQ ID NO:4.

In some embodiments, the monoclonal antibody as described herein is an immunoglobulin G (IgG), an IgM, an IgE, an IgA or an IgD molecule, or a derivative thereof. In some embodiments, the monoclonal antibody as described herein is an IgG1, IgG2, IgG3, or IgG4, or a derivative thereof.

In some embodiments, the monoclonal antibody as described herein is a chimeric antibody.

In some embodiments, the monoclonal antibody, or antigen-binding portion thereof as described herein comprises a light chain variable domain amino acid sequence having at least 95% identity to SEQ ID NO:2 and a heavy chain variable domain amino acid sequence having at least 95% identity to SEQ ID NO:4.

In one aspect, provided herein is an isolated nucleic acid molecule encoding the antibody, or antigen-binding portion thereof as described herein.

In one aspect, provided herein is a host cell comprising a sequence of the nucleic acid molecule as described herein.

In one aspect, provided herein is an immunoconjugate comprising the antibody, or antigen-binding portion thereof as described herein, linked to a therapeutic agent.

In one aspect, provided herein is a monoclonal antibody, or antigen-binding portion thereof, which comprises a light chain comprising SEQ ID NO:11 and a heavy chain comprising SEQ ID NO:12.

In one aspect, the methods described herein can also be used for treating T cell dysfunctional disorders, including infection (e.g., acute and chronic) and tumor immunity.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

Exemplary embodiments are illustrated in referenced figures. It is intended that the embodiments and figures disclosed herein are to be considered illustrative rather than restrictive.

FIG. 9 lists sequences that are described in the present disclosure.

DETAILED DESCRIPTION

Figure 1:
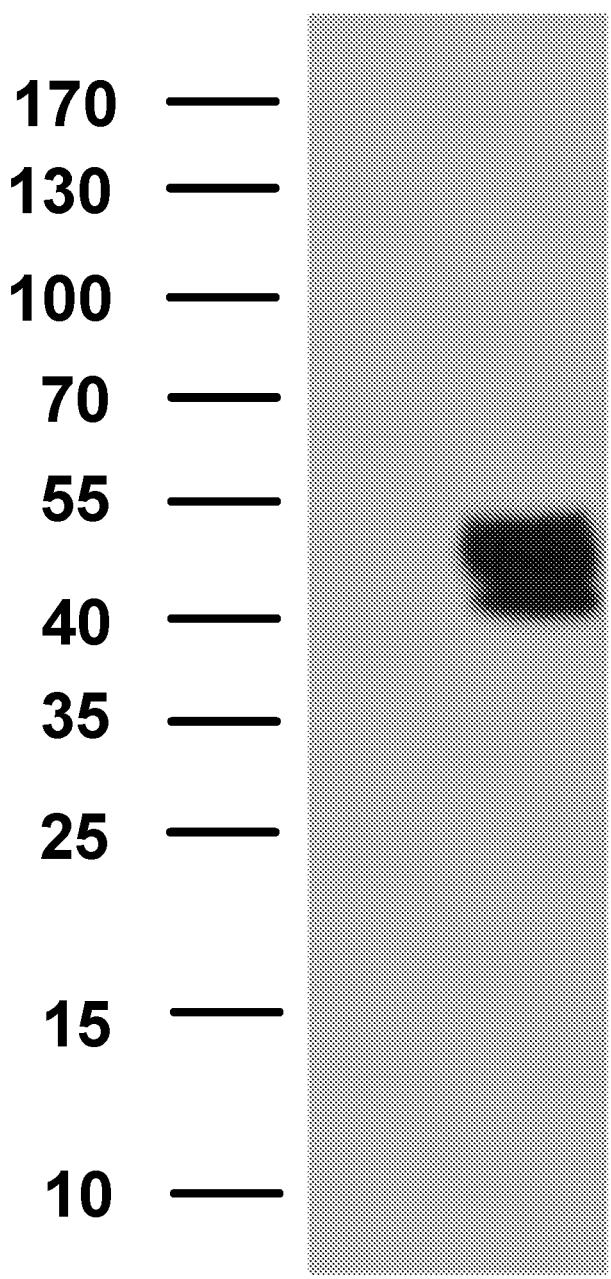
FIG. 1 shows the Western Blot analysis with the anti-PD-1 antibody (clone #11). HEK293T cells were transfected with the pCMV6-ENTRY control (Left lane) or pCMV6-ENTRY PDCD1 (RC210364, Right lane) cDNA for 48 hours and then were lysed. Equivalent amounts of cell lysates (5 µg per lane) were separated by SDS-PAGE and immunoblotted with anti-PD-1 antibodies (1:2000).

The present disclosure relates to an isolated monoclonal antibody which binds to PD-1 and blocks interaction between PD-1 and PD-L1. In certain embodiments, the monoclonal antibody or antigen-binding portion thereof also blocks the interaction between PD-1 and PD-L2. In certain embodiments, the antibodies of the disclosure are derived from identified heavy and light chain germline sequences and/or comprise identified structural features such as CDR regions comprising identified amino acid sequences. This disclosure provides isolated antibodies, methods of making such antibodies and antigen-binding portions thereof of the disclosure. This disclosure also relates to methods of using the antibodies, such as using the anti-PD-1 antibodies of the disclosure to stimulate immune responses, alone or in combination with other immunostimulatory antibodies. Accordingly, also provided are methods of using the anti-PD-1 antibodies of the disclosure for example, including but not limited to, treating cancer in a human.

Therapeutic mouse antibodies sometimes can cause human anti-mouse antibody (HAMA) response. In this situation, therapeutic antibodies can lose their efficacy. The disclosure also provides humanized antibodies that have reduced HAMA response and prolonged therapeutic efficacy.

In some embodiments, the humanized antibodies can be used in anticancer therapies. In some embodiments, the humanized antibodies can be used as a standalone therapeutic. In some embodiments, the humanized antibodies can be used as in combination with cell therapies. In some embodiments, the humanized antibodies described herein can be further refined into single-chain variable fragment (e.g., scFv).

As used herein, the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the term "about" refers to a measurable value such as an amount, a time duration, and the like, and encompasses variations of ±20%, ±10%, ±5%, ±1%, ±0.5% or ±0.1% from the specified value.

As used herein, the term "epitope" can include any protein determinant capable of specific binding to an immunoglobulin or T-cell receptor. Epitopic determinants usually consist of chemically active surface groupings of molecules such as amino acids or sugar side chains and usually have specific three-dimensional structural characteristics, as well as specific charge characteristics. An antibody is said to specifically bind an antigen when the equilibrium dissociation constant is <1 µM, preferably <100 nM and most preferably <10 nM.

As used herein, the term "immune response" can refer to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from an organism of invading pathogens, cells or tissues infected with pathogens, cancerous cells, or, in cases of autoimmunity or pathological inflammation, normal organismal cells or tissues.

As used herein, the term "antigen-specific T cell response" can refer to responses by a T cell that result from stimulation of the T cell with the antigen for which the T cell is specific. Non-limiting examples of responses by a T cell upon antigen-specific stimulation include, but are not limited to, proliferation and cytokine production (e.g., IL-2 production).

As used herein, the term "antibody" refers to an intact immunoglobulin, or to a monoclonal or polyclonal antigen-binding fragment with the Fc (crystallizable fragment) region or FcRn binding fragment of the Fc region, referred to herein as the "Fc fragment" or "Fc domain". Antigen-binding fragments can be produced by recombinant DNA techniques or by enzymatic or chemical cleavage of intact antibodies. Antigen-binding fragments include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The Fc domain includes portions of two heavy chains contributing to two or three classes of the antibody. The Fc domain can be produced by recombinant DNA techniques or by enzymatic (e.g. papain cleavage) or via chemical cleavage of intact antibodies.

As used herein, the term "antibody fragment" or "antigen-binding fragment" refers to a protein fragment that comprises only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 341, 544-546 (1989)) which consists of a VH domain; (vii) isolated CDR regions; (viii) F(ab')2 fragments, a bivalent fragment including two Fab' fragments linked by a disulfide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. Protein Eng. 8(10):1057-1062 (1995); and U.S. Pat. No. 5,641,870).

As used herein, "single-chain variable fragment", "single-chain antibody variable fragments" or "scFv" antibodies refers to forms of antibodies comprising the variable regions of only the heavy (VH) and light (VL) chains, connected by a linker peptide. The scFvs are capable of being expressed as a single chain polypeptide. The scFvs retain the specificity of the intact antibody from which it is derived. The light and heavy chains can be in any order, for example, VH-linker-VL or VL-linker-VH, so long as the specificity of the scFv to the target antigen is retained.

As used herein, an "isolated antibody" can refer to an antibody that is substantially free of other antibodies having different antigenic specificities (e.g., an isolated antibody that specifically binds a PD-1 protein can be substantially free of antibodies that specifically bind antigens other than PD-1 proteins). An isolated antibody that specifically binds a human PD-1 protein can, however, have cross-reactivity to other antigens, such as PD-1 proteins from other species. Moreover, an isolated antibody can be substantially free of other cellular material and/or chemicals.

Anti-PD-1 antibody-producing cells, e.g., hybridomas, can be selected, cloned and further screened for desirable characteristics, including robust growth, high antibody production and desirable antibody characteristics. Hybridomas can be expanded in vivo in syngeneic animals, in animals that lack an immune system, e.g., nude mice, or in cell culture in vitro. Methods of selecting, cloning and expanding hybridomas are well known to those of ordinary skill in the art.

As used herein, the terms "monoclonal antibody" or "monoclonal antibody composition" can refer to a preparation of antibody molecules of single molecular composition. A monoclonal antibody composition displays a single binding specificity and affinity for a particular epitope.

As used herein, the term "recombinant human antibody", can refer to all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, the term "isotype" can refer to the antibody class (e.g., IgM or IgG1) that is encoded by the heavy chain constant region genes.

A "humanized antibody" has a sequence that differs from the sequence of an antibody derived from a non-human species by one or more amino acid substitutions, deletions, and/or additions, such that the humanized antibody is less likely to induce an anti-antibody immune response, and/or induces a less severe anti-antibody immune response, as compared to the non-human species antibody, when it is administered to a human subject. In some embodiments, certain amino acids in the framework and constant domains of the heavy and/or light chains of the non-human species antibody are mutated to produce the humanized antibody. In some embodiments, the constant domain(s) from a human antibody are fused to the variable domain(s) of a non-human species. In some embodiments, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies can be found in U.S. Pat. Nos. 6,054,297, 5,886,152 and 5,877,293, which are incorporated herein by reference in the entirety.

As used herein, the term "chimeric antibody" can refer to antibodies in which the variable region sequences can be derived from one species and the constant region sequences can be derived from another species, such as an antibody in which the variable region sequences can be derived from a mouse antibody and the constant region sequences can be derived from a human antibody.

As used herein, an antibody that "specifically binds human PD-1" can refer to an antibody that binds to a human PD-1 protein (and possibly a PD-1 protein from one or more non-human species) but does not substantially bind to non-PD-1 proteins. In some embodiments, the antibody binds to a human PD-1 protein with "high affinity," e.g., with a EC50 of $1\times10^{-7}$ M or less, more preferably $5\times10^{-8}$ M or less, more preferably $3\times10^{-8}$ M or less, more preferably $1\times10^{-8}$ M or less, more preferably $5\times10^{-9}$ M or less or even more preferably $1\times10^{-9}$ M or less. The phrases "an antibody recognizing an antigen" and "an antibody specific for an antigen" are used interchangeably herein with the term "an antibody which binds specifically to an antigen."

As used herein, the term "does not substantially bind" to a protein or cells, can mean that it cannot bind or does not bind with a high affinity to the protein or cells, i.e., binds to the protein or cells with an EC50 of $2\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

As used herein, the term "high affinity" for an IgG antibody can refer to an antibody having an Kd of $1\times10^{-6}$ M or less, more preferably $1\times10^{-7}$ M or less, even more preferably $1\times10^{-8}$ M or less, even more preferably $1\times10^{-9}$ M or less, even more preferably $1\times10^{-10}$ M or less for a target antigen. However, "high affinity" binding can vary for other antibody isotypes.

As used herein, the term "pharmaceutical formulation" refers to a preparation which is in such form as to permit the biological activity of an active ingredient contained therein to be effective, and which contains no additional components which are unacceptably toxic to a subject to which the formulation would be administered.

As used herein, the term "inhibit" refers to any decrease in, for example a particular action, function, or interaction. For example, a biological function, such as the function of a protein and/or binding of one protein to another, is inhibited if it is decreased as compared to a reference state, such as a control like a wild-type state or a state in the absence of an applied agent. For example, the binding of a PD-1 protein to one or more of its ligands, such as PD-L1 and/or PD-L2, and/or resulting PD-1 signaling and immune effects is inhibited or deficient if the binding, signaling, and other immune effects are decreased due to contact with an agent, such as an anti-PD-1 antibody, in comparison to when the PD-1 protein is not contacted with the agent. Such inhibition or deficiency can be induced, such as by application of agent at a particular time and/or place, or can be constitutive, such as by continual administration. Such inhibition or deficiency can also be partial or complete (e.g., essentially no measurable activity in comparison to a reference state, such as a control like a wild-type state). Essentially complete inhibition or deficiency is referred to as blocked.

As used herein, the term "subject" can refer to any human or non-human animal. The subject can be male or female and can be any suitable age, including infant, juvenile, adolescent, adult, and geriatric subjects. The term "nonhuman animal" includes all vertebrates, e.g., mammals and non-mammals, such as nonhuman primates, sheep, dogs, cats, cows, horses, chickens, rabbits, mice, rats, amphibians, and reptiles, although mammals are preferred, such as non-human primates, sheep, dogs, cats, cows and horses.

PD-1 and Immune System

The immune system can differentiate between normal cells in the body and those it sees as "foreign," which allows the immune system to attack the foreign cells while leaving the normal cells alone. This mechanism sometimes involves proteins called immune checkpoints. Immune checkpoints are molecules in the immune system that either turn up a signal (co-stimulatory molecules) or turn down a signal.

Checkpoint inhibitors can prevent the immune system from attacking normal tissue and thereby preventing autoimmune diseases. Many tumor cells also express checkpoint inhibitors. These tumor cells escape immune surveillance by co-opting certain immune-checkpoint pathways, particularly in T cells that are specific for tumor antigens (Creelan, Benjamin C. "Update on immune checkpoint inhibitors in lung cancer." Cancer Control 21.1 (2014): 80-89). Because many immune checkpoints are initiated by ligand-receptor interactions, they can be readily blocked by antibodies against the ligands and/or their receptors.

PD-1 (Programmed Cell Death 1; PDCD1; or Programmed Death 1) is an immune checkpoint and guards against autoimmunity through a dual mechanism of promoting apoptosis (programmed cell death) in antigen-specific T-cells in lymph nodes while simultaneously reducing apoptosis in regulatory T cells (anti-inflammatory, suppressive T cells).

PD-1 is mainly expressed on the surfaces of T cells and primary B cells; two ligands of PD-1 (PD-L1 and PD-L2) are widely expressed in antigen-presenting cells (APCs). The interaction of PD-1 with its ligands plays an important role in the negative regulation of the immune response. Inhibition the binding between PD-1 and its ligand can make the tumor cells exposed to the killing effect of the immune system, and thus can reach the effect of killing tumor tissues and treating cancers.

PD-L1 (CD274) is expressed on the neoplastic cells of many different cancers. By binding to PD-1 on T-cells leading to its inhibition, PD-L1 expression is a major mechanism by which tumor cells can evade immune attack. PD-L1 over-expression may conceptually be due to 2 mechanisms, intrinsic and adaptive. Intrinsic expression of PD-L1 on cancer cells is related to cellular/genetic aberrations in these neoplastic cells. Activation of cellular signaling including the AKT and STAT pathways results in increased PD-L1 expression. In primary mediastinal B-cell lymphomas, gene fusion of the MHC class II transactivator (CIITA) with PD-L1 or PD-L2 occurs, resulting in overexpression of these proteins. Amplification of chromosome 9p23-24, where PD-L1 and PD-L2 are located, leads to increased expression of both proteins in classical Hodgkin lymphoma. Adaptive mechanisms are related to induction of PD-L1 expression in the tumor microenvironment. PD-L1 can be induced on neoplastic cells in response to interferon γ. In microsatellite instability colon cancer, PD-L1 is mainly expressed on myeloid cells in the tumors, which then suppress cytotoxic T-cell function.

The use of PD-1 blockade to enhance anti-tumor immunity originated from observations in chronic infection models, where preventing PD-1 interactions reversed T-cell exhaustion. Similarly, blockade of PD-1 prevents T-cell PD-1/tumor cell PD-L1 or T-cell PD-1/tumor cell PD-L2 interaction, leading to restoration of T-cell mediated anti-tumor immunity.

A detailed description of PD-1, and the use of anti-PD-1 antibodies to treat cancers are described, e.g., in Topalian, Suzanne L., et al. "Safety, activity, and immune correlates of anti-PD-1 antibody in cancer." New England Journal of Medicine 366.26 (2012): 2443-2454; Hirano, Fumiya, et al. "Blockade of B7-H1 and PD-1 by monoclonal antibodies potentiates cancer therapeutic immunity." Cancer research 65.3 (2005): 1089-1096; Raedler, Lisa A. "Keytruda (pembrolizumab): first PD-1 inhibitor approved for previously treated unresectable or metastatic melanoma." American health & drug benefits 8. Spec Feature (2015): 96; Kwok, Gerry, et al. "Pembrolizumab (Keytruda)." (2016): 2777-2789; US 20170247454; U.S. Pat. Nos. 9,834,606 B; and 8,728,474; each of which is incorporated by reference in its entirety.

The present disclosure provides anti-PD-1 antibodies, antigen-binding fragments thereof, and methods of using these anti-PD-1 antibodies and antigen-binding fragments to inhibit tumor growth and to treat cancers.

Anti-PD-1 Antibodies and Antigen-Binding Fragments

The disclosure provides antibodies and antigen-binding fragments thereof that specifically bind to PD-1. The antibodies and antigen-binding fragments described herein are capable of binding to PD-1. In some embodiments, these antibodies can block PD-1 signaling pathway thus increase immune response. In some embodiments, these antibodies can initiate complement-dependent cytotoxicity (CMC) or antibody-dependent cellular cytotoxicity (ADCC).

The disclosure provides e.g., mouse anti-PD-1 antibodies (e.g., F02), and the chimeric antibodies thereof, and the humanized antibodies thereof (e.g., H11, Ab8, Ab2, Ab5, Ab7, Ab4).

The CDR sequences for F02, and F02 derived antibodies or antigen-binding fragments thereof include VH CDR1, VH CDR2, and VH CDR3 comprising or consisting of SEQ ID NOs: 8, 9, 10 respectively, and VL CDR1, VL CDR2, and VL CDR3 comprising or consisting of SEQ ID NOs: 5, 6, 7, respectively.

The CDR sequences for H11, and H11 derived antibodies or antigen-binding fragments thereof include VH CDR1, VH CDR2, and VH CDR3 comprising or consisting of SEQ ID NOs: 22, 23, 24, respectively, and VL CDR1, VL CDR2, and VL CDR3 comprising or consisting of SEQ ID NOs: 19, 20, 21, respectively.

The CDR sequences for Ab8, and Ab8 derived antibodies or antigen-binding fragments thereof include VH CDR1, VH CDR2, and VH CDR3 comprising or consisting of SEQ ID NOs: 74, 75, 76, respectively, and VL CDR1, VL CDR2, and VL CDR3 comprising or consisting of SEQ ID NOs: 71, 72, 73, respectively.

The CDR sequences for Ab2, and Ab2 derived antibodies or antigen-binding fragments thereof include VH CDR1, VH CDR2, and VH CDR3 comprising or consisting of SEQ ID NOs: 34, 35, 36, respectively, and VL CDR1, VL CDR2, and VL CDR3 comprising or consisting of SEQ ID NOs: 31, 32, 33, respectively.

The CDR sequences for Ab5, and Ab5 derived antibodies or antigen-binding fragments thereof include VH CDR1, VH CDR2, and VH CDR3 comprising or consisting of SEQ ID NOs: 54, 55, 56, respectively, and VL CDR1, VL CDR2, and VL CDR3 comprising or consisting of SEQ ID NOs: 51, 52, 53, respectively.

The CDR sequences for Ab7, and Ab7 derived antibodies or antigen-binding fragments thereof include VH CDR1, VH CDR2, and VH CDR3 comprising or consisting of SEQ ID NOs: 64, 65, 66, respectively, and VL CDR1, VL CDR2, and VL CDR3 comprising or consisting of SEQ ID NOs: 61, 62, 63, respectively.

The CDR sequences for Ab8, and Ab8 derived antibodies or antigen-binding fragments thereof include VH CDR1, VH CDR2, and VH CDR3 comprising or consisting of SEQ ID NOs: 44, 45, 46, respectively, and VL CDR1, VL CDR2, and VL CDR3 comprising or consisting of SEQ ID NOs: 41, 42, 43, respectively.

The amino acid sequence for the heavy chain variable region of F02 antibody is set forth in SEQ ID NO: 4. The amino acid sequence for the light chain variable region of F02 antibody is set forth in SEQ ID NO: 2.

The amino acid sequence for the heavy chain variable region of H11 antibody is set forth in SEQ ID NO: 18. The amino acid sequence for the light chain variable region of H11 antibody is set forth in SEQ ID NO: 16.

The amino acid sequence for the heavy chain variable region of Ab8 antibody is set forth in SEQ ID NO: 70. The amino acid sequence for the light chain variable region of Ab8 antibody is set forth in SEQ ID NO: 68.

The amino acid sequence for the heavy chain variable region of Ab2 antibody is set forth in SEQ ID NO: 30. The amino acid sequence for the light chain variable region of Ab2 antibody is set forth in SEQ ID NO: 28.

The amino acid sequence for the heavy chain variable region of Ab5 antibody is set forth in SEQ ID NO: 50. The amino acid sequence for the light chain variable region of Ab5 antibody is set forth in SEQ ID NO: 48.

The amino acid sequence for the heavy chain variable region of Ab7 antibody is set forth in SEQ ID NO: 60. The amino acid sequence for the light chain variable region of Ab7 antibody is set forth in SEQ ID NO: 58.

The amino acid sequence for the heavy chain variable region of Ab4 antibody is set forth in SEQ ID NO: 40. The amino acid sequence for the light chain variable region of Ab4 antibody is set forth in SEQ ID NO: 38.

The amino acid sequences for heavy chain variable regions and light variable regions of the humanized antibodies are also provided. As there are different ways to humanize a mouse antibody (e.g., a sequence can be modified with different amino acid substitutions), the heavy chain and the light chain of an antibody can have more than one version of humanized sequences. In some embodiments, the humanized heavy chain variable region is at least 80%, 85%, 90%, 91%, 92%, 93%, 94%, 95%, 96%, 97%, 98%, or 99% identical to SEQ ID NO: 4, 18, 70, 30, 50, 60, or 40. In some embodiments, the humanized light chain variable region is at least 80%, 85%, 90%, 91%, 92%, 93%, 94%, 95%, 96%, 97%, 98%, or 99% identical to SEQ ID NO: 2, 16, 68, 28, 48, 58, or 38. The heavy chain variable region sequence can be paired with the light chain variable region sequence, and together they bind to PD-1.

Humanization percentage means the percentage identity of the heavy chain or light chain variable region sequence as compared to human antibody sequences in International Immunogenetics Information System (IMGT) database. The top hit means that the heavy chain or light chain variable region sequence is closer to a particular species than to other species. For example, top hit to human means that the sequence is closer to human than to other species. Top hit to human and *Macaca fascicularis* means that the sequence has the same percentage identity to the human sequence and the *Macaca fascicularis* sequence, and these percentages identities are highest as compared to the sequences of other species. In some embodiments, humanization percentage is greater than 80%, 81%, 82%, 83%, 84%, 85%, 86%, 87%, 88%, 89%, 90%, 91%, 92%, 93%, 94%, or 95%. A detailed description regarding how to determine humanization percentage and how to determine top hits is known in the art, and is described, e.g., in Jones, et al. "The INNs and outs of antibody nonproprietary names." MAbs. Vol. 8. No. 1. Taylor & Francis, 2016, which is incorporated herein by reference in its entirety. A high humanization percentage often has various advantages, e.g., more safe and more effective in humans, more likely to be tolerated by a human subject, and/or less likely to have side effects.

Furthermore, in some embodiments, the antibodies or antigen-binding fragments thereof described herein can also contain one, two, or three heavy chain variable region CDRs selected from the group of SEQ ID NOs: 8-10, SEQ ID NOs: 22-24, SEQ ID NOs: 74-76, SEQ ID NOs: 34-36, SEQ ID NOs: 54-56, SEQ ID NOs: 64-66, and SEQ ID NOs: 44-46; and/or one, two, or three light chain variable region CDRs selected from the group of SEQ ID NOs: 5-7, SEQ ID NOs: 19-21, SEQ ID NOs: 71-73, SEQ ID NOs: 31-33, SEQ ID NOs: 51-53, SEQ ID NOs: 61-63, and SEQ ID Nos: 41-43.

In some embodiments, the antibodies can have a heavy chain variable region (VH) comprising complementarity determining regions (CDRs) 1, 2, 3, wherein the CDR1 region comprises or consists of an amino acid sequence that is at least 80%, 85%, 90%, or 95% identical to a selected VH CDR1 amino acid sequence, the CDR2 region comprises or consists of an amino acid sequence that is at least 80%, 85%, 90%, or 95% identical to a selected VH CDR2 amino acid sequence, and the CDR3 region comprises or consists of an amino acid sequence that is at least 80%, 85%, 90%, or 95% identical to a selected VH CDR3 amino acid sequence. In some embodiments, the antibodies can have a light chain variable region (VL) comprising CDRs 1, 2, 3, wherein the CDR1 region comprises or consists of an amino acid sequence that is at least 80%, 85%, 90%, or 95% identical to a selected VL CDR1 amino acid sequence, the CDR2 region comprises or consists of an amino acid sequence that is at least 80%, 85%, 90%, or 95% identical to a selected VL CDR2 amino acid sequence, and the CDR3 region comprises or consists of an amino acid sequence that is at least 80%, 85%, 90%, or 95% identical to a selected VL CDR3 amino acid sequence. The selected VH CDRs 1, 2, 3 amino acid sequences and the selected VL CDRs, 1, 2, 3 amino acid sequences are shown in FIG. 9.

In some embodiments, the antibody or an antigen-binding fragment described herein can contain a heavy chain variable domain containing one, two, or three of the CDRs of SEQ ID NO: 8 with zero, one or two amino acid insertions, deletions, or substitutions; SEQ ID NO: 9 with zero, one or two amino acid insertions, deletions, or substitutions; SEQ ID NO: 10 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 22 with zero, one or two amino acid insertions, deletions, or substitutions; SEQ ID NO: 23 with zero, one or two amino acid insertions, deletions, or substitutions; SEQ ID NO: 24 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 74 with zero, one or two amino acid insertions, deletions, or substitutions; SEQ ID NO: 75 with zero, one or two amino acid insertions, deletions, or substitutions; SEQ ID NO: 76 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 34 with zero, one or two amino acid insertions, deletions, or substitutions; SEQ ID NO: 35 with zero, one or two amino acid insertions, deletions, or substitutions; SEQ ID NO: 36 with zero, one or two amino acid insertions, deletions, or substitutions.

In some embodiments, the antibody or an antigen-binding fragment described herein can contain a light chain variable domain containing one, two, or three of the CDRs of SEQ ID NO: 5 with zero, one or two amino acid insertions, deletions, or substitutions; SEQ ID NO: 6 with zero, one or two amino acid insertions, deletions, or substitutions; SEQ ID NO: 7 with zero, one or two amino acid insertions, deletions, or substitutions.

In some embodiments, the antibody or an antigen-binding fragment described herein can contain a light chain variable domain containing one, two, or three of the CDRs of SEQ ID NO: 19 with zero, one or two amino acid insertions, deletions, or substitutions; SEQ ID NO: 20 with zero, one or two amino acid insertions, deletions, or substitutions; SEQ ID NO: 21 with zero, one or two amino acid insertions, deletions, or substitutions.

In some embodiments, the antibody or an antigen-binding fragment described herein can contain a light chain variable domain containing one, two, or three of the CDRs of SEQ ID NO: 71 with zero, one or two amino acid insertions, deletions, or substitutions; SEQ ID NO: 72 with zero, one or two amino acid insertions, deletions, or substitutions; SEQ ID NO: 73 with zero, one or two amino acid insertions, deletions, or substitutions.

In some embodiments, the antibody or an antigen-binding fragment described herein can contain a light chain variable domain containing one, two, or three of the CDRs of SEQ ID NO: 31 with zero, one or two amino acid insertions, deletions, or substitutions; SEQ ID NO: 32 with zero, one or two amino acid insertions, deletions, or substitutions; SEQ ID NO: 33 with zero, one or two amino acid insertions, deletions, or substitutions.

The insertions, deletions, and substitutions can be within the CDR sequence, or at one or both terminal ends of the CDR sequence. In some embodiments, the CDR is determined based on Kabat numbering scheme.

The disclosure also provides antibodies or antigen-binding fragments thereof that bind to PD-1. The antibodies or antigen-binding fragments thereof contain a heavy chain variable region (VH) comprising or consisting of an amino acid sequence that is at least 80%, 85%, 90%, or 95% identical to a selected VH sequence, and a light chain variable region (VL) comprising or consisting of an amino acid sequence that is at least 80%, 85%, 90%, or 95% identical to a selected VL sequence. In some embodiments, the selected VH sequence is SEQ ID NO: 4, and the selected VL sequence is SEQ ID NO: 2. In some embodiments, the selected VH sequence is SEQ ID NO: 18 and the selected VL sequence is SEQ ID NO: 16. In some embodiments, the selected VH sequence is SEQ ID NO: 70 and the selected VL sequence is SEQ ID NO: 68. In some embodiments, the selected VH sequence is SEQ ID NO: 30 and the selected VL sequence is SEQ ID NO: 28. In some embodiments, the selected VH sequence is SEQ ID NO: 50 and the selected VL sequence is SEQ ID NO: 48. In some embodiments, the selected VH sequence is SEQ ID NO: 60 and the selected VL sequence is SEQ ID NO: 58. In some embodiments, the selected VH sequence is SEQ ID NO: 40 and the selected VL sequence is SEQ ID NO: 38.

The disclosure also provides nucleic acid comprising a polynucleotide encoding a polypeptide comprising an immunoglobulin heavy chain or an immunoglobulin light chain. The immunoglobulin heavy chain or immunoglobulin light chain comprises CDRs, or have sequences as shown in FIG. 9. When the polypeptides are paired with corresponding polypeptide (e.g., a corresponding heavy chain variable region or a corresponding light chain variable region), the paired polypeptides bind to PD-1 (e.g., human PD-1).

The anti-PD-1 antibodies and antigen-binding fragments can also be antibody variants (including derivatives and conjugates) of antibodies or antibody fragments and multi-specific (e.g., bi-specific) antibodies or antibody fragments. Additional antibodies provided herein are polyclonal, monoclonal, multi-specific (multimeric, e.g., bi-specific), human antibodies, chimeric antibodies (e.g., human-mouse chimera), single-chain antibodies, intracellularly-made antibodies (i.e., intrabodies), and antigen-binding fragments thereof. The antibodies or antigen-binding fragments thereof can be of any type (e.g., IgG, IgE, IgM, IgD, IgA, and IgY), class (e.g., IgG1, IgG2, IgG3, IgG4, IgA1, and IgA2), or subclass. In some embodiments, the antibody or antigen-binding fragment thereof is an IgG antibody or antigen-binding fragment thereof.

Fragments of antibodies are suitable for use in the methods provided so long as they retain the desired affinity and specificity of the full-length antibody. Thus, a fragment of an antibody that binds to PD-1 will retain an ability to bind to PD-1. An Fv fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer. Collectively, the six CDRs or a subset thereof confer antigen binding specificity to the antibody. However, even a single variable domain (or half of an Fv comprising only three CDRs specific for an antigen) can have the ability to recognize and bind antigen, although usually at a lower affinity than the entire binding site. Single-chain Fv or (scFv) antibody fragments comprise the VH and VL domains (or regions) of antibody, wherein these domains are present in a single polypeptide chain. Generally, the scFv polypeptide further comprises a polypeptide linker between the VH and VL domains, which enables the scFv to form the desired structure for antigen binding.

The present disclosure also provides an antibody or antigen-binding fragment thereof that cross-competes with any antibody or antigen-binding fragment as described herein. The cross-competing assay is known in the art, and is described e.g., in Moore et al., "Antibody cross-competition analysis of the human immunodeficiency virus type 1 gp120 exterior envelope glycoprotein." Journal of virology 70.3 (1996): 1863-1872, which is incorporated herein reference in its entirety. In one aspect, the present disclosure also provides an antibody or antigen-binding fragment thereof that binds to the same epitope or region as any antibody or antigen-binding fragment as described herein. The epitope binning assay is known in the art, and is described e.g., in Estep et al. "High throughput solution-based measurement of antibody-antigen affinity and epitope binning." MAbs. Vol. 5. No. 2. Taylor & Francis, 2013, which is incorporated herein reference in its entirety.

In one aspect, this disclosure provides an isolated human PD-1 binding monoclonal antibody, or antigen-binding portion thereof comprising: (a) a light chain variable region comprising an amino acid sequence comprising SEQ ID NO:2; and (b) a heavy chain variable region comprising an amino acid sequence comprising SEQ ID NO:4; wherein the antibody or portion blocks the interaction between PD-1 and PD-L1 and also the interaction between PD-1 and PD-L2.

In another aspect, this disclosure provides an isolated monoclonal antibody, or antigen-binding portion thereof comprising: (a) a light chain variable region comprising an amino acid sequence comprising SEQ ID NO:2; and (b) a heavy chain variable region comprising an amino acid sequence comprising SEQ ID NO:4; wherein the antibody specifically binds to PD-1 and blocks the interaction between PD-1 and PD-L1. In some embodiments, the monoclonal antibody, or an antigen-binding portion thereof stimulates an anti-tumor immune response. In some embodiments, the monoclonal antibody can be a chimeric antibody.

In another aspect, this disclosure provides antibodies that comprise the heavy chain and light chain CDR1, CDR2 and CDR3 of clone #11. The amino acid sequences of the VL CDR1 of clone #11 is shown in SEQ ID NO:5. The amino acid sequences of the VL CDR2s of clone #11 is SEQ ID NO:6. The amino acid sequences of the VL CDR3s of clone #11 is shown in SEQ ID NO:7. The amino acid sequence of the VH CDR1 of clone #11 is shown in SEQ ID NO:8. The amino acid sequence of the VH CDR2 of clone #11 is shown in SEQ ID NO:9. The amino acid sequence of the VH CDR3 of clone #11 is shown in SEQ ID NO:10. The CDR regions can be delineated using the Kabat system (Kabat et al. (1991) Sequences of Proteins of Immunological Interest, Fifth Edition, U.S. Department of Health and Human Services, NIH Publication No. 91-3242).

In another aspect, this disclosure provides polynucleotide sequences encoding the light chain variable domain (VL) and heavy chain variable domains (VH) of the monoclonal antibody clone #11. The VL polynucleotide sequence is shown in SEQ ID NO:1. The VH polynucleotide sequence is shown in SEQ ID NO:3.

Antibodies can be affinity matured by light-chain shuffling combined with or without random mutagenesis of its heavy chain variable domain and panning against PD-1. The VL CDR1, CDR2 and CDR3 of the antibodies mentioned in this disclosure can be optimized with light-chain shuffling to create other anti-PD-1 binding molecules of the disclosure.

An antibody of the disclosure further can be prepared using an antibody having one or more of the VH and/or VL sequences disclosed herein as starting material to engineer a modified antibody, which modified antibody can have altered properties from the starting antibody. An antibody can be engineered by modifying one or more residues within one or both variable regions (i.e., VH and/or VL), for example within one or more CDR regions and/or within one or more framework regions. Additionally, or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs).

Because CDR sequences can be responsible for most antibody-antigen interactions, it can be possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al. (1998) Nature 332:323-327; Jones et al. (1986) Nature 321: 522-525; Queen et al. (1989) Proc. Natl. Acad. See. U.S.A. 86: 10029-10033; U.S. Pat. Nos. 5,225, 539; 5,530,101; 5,585,089; 5,693,762 and 6,180,370.)

Accordingly, another embodiment of the disclosure pertains to an isolated monoclonal antibody, or antigen-binding portion thereof, comprising a light chain variable region comprising CDR1, CDR2, and CDR3 sequences comprising an amino acid sequence of SEQ ID NO:5, SEQ ID NO:6, and SEQ ID NO:7, respectively, and a heavy chain variable region a comprising CDR1, CDR2, and CDR3 sequences comprising an amino acid sequence of SEQ ID NO:8, SEQ ID NO:9 and SEQ ID NO:10, respectively. Thus, such antibodies contain the VH and VL CDR sequences of anti-PD-1 monoclonal antibody from hybridoma clone #11 and can contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al. (1991), cited supra; Tomlinson et al. (1992) "The Repertoire of Human Germline VH Sequences Reveals about Fifty Groups of VH Segments with Different Hypervariable Loops" J. Mol. Biol. 227:776-798; and Cox et al. (1994) "A Directory of Human Germ-line VH Segments Reveals a Strong Bias in their Usage" Eur. J. Immunol. 24:827-836; the contents of each of which are expressly incorporated herein by reference. As another example, the germline DNA sequences for human heavy and light chain variable region genes can be found in the GenBank database. For example, the following heavy chain germline sequences found in the HCo7 HuMAb mouse are available in the accompanying GenBankAccession NOS.:1-69 (NG_0010109, NT_024637 & BC070333), 3-33 (NG_0010109 & NT_024637) and 3-7 (NG_0010109 &NT_024637). As another example, the following heavy chain germline sequences found in the HCo12 HuMAb mouse are available in the accompanying GenBankAccession NOS.: 1-69 (NG_0010109, NT_024637 & BC070333), 5-51 (NG_0010109 & NT_024637), 4-34 (NG_0010109 & NT_024637), 3-30.3 (CAJ556644) & 3-23 (AJ406678).

Antibody protein sequences are compared against a compiled protein sequence database using one of the sequence similarity searching methods called the Gapped BLAST (Altschul et al. (1997)), which is well known to those skilled in the art. The compositions and methods of the presently disclosure are not limited to variants of the exemplary sequences disclosed herein but include those having at least 90%, at least 95% and at least 99% sequence identity to an exemplary sequence disclosed herein.

Antibodies and Antigen Binding Fragments

The present disclosure provides various antibodies and antigen-binding fragments thereof derived from anti-PD-1 antibodies described herein. In general, antibodies (also called immunoglobulins) are made up of two classes of polypeptide chains, light chains and heavy chains. A non-limiting examples of antibody of the present disclosure can be an intact, four immunoglobulin chain antibody comprising two heavy chains and two light chains. The heavy chain of the antibody can be of any isotype including IgM, IgG, IgE, IgA, or IgD or sub-isotype including IgG1, IgG2, IgG2a, IgG2b, IgG3, IgG4, IgE1, IgE2, etc. The light chain can be a kappa light chain or a lambda light chain. An antibody can comprise two identical copies of a light chain and two identical copies of a heavy chain. The heavy chains, which each contain one variable domain (or variable region, $V_H$) and multiple constant domains (or constant regions), bind to one another via disulfide bonding within their constant domains to form the "stem" of the antibody. The light chains, which each contain one variable domain (or variable region, $V_L$) and one constant domain (or constant region), each bind to one heavy chain via disulfide binding. The variable region of each light chain is aligned with the variable region of the heavy chain to which it is bound. The variable regions of both the light chains and heavy chains contain three hypervariable regions sandwiched between more conserved framework regions (FR).

These hypervariable regions, known as the complementary determining regions (CDRs), form loops that comprise the antigen binding surface of the antibody. The four framework regions largely adopt a beta-sheet conformation and the CDRs form loops connecting the beta-sheet structure, and in some cases forming part of, the beta-sheet structure. The CDRs in each chain are held in close proximity by the framework regions and, with the CDRs from the other chain, contribute to the formation of the antigen-binding region.

Methods for identifying the CDR regions of an antibody by analyzing the amino acid sequence of the antibody are well known, and a number of definitions of the CDRs are commonly used. The Kabat definition is based on sequence variability, and the Chothia definition is based on the location of the structural loop regions. These methods and definitions are described in, e.g., Martin, "Protein sequence and structure analysis of antibody variable domains," Antibody engineering, Springer Berlin Heidelberg, 2001. 422-439; Abhinandan, et al. "Analysis and improvements to Kabat and structurally correct numbering of antibody variable domains," Molecular immunology 45.14 (2008): 3832-

3839; Wu, T.T. and Kabat, E.A. (1970) J. Exp. Med. 132: 211-250; Martin et al., Methods Enzymol. 203:121-53 (1991); Morea et al., Biophys Chem. 68(1-3):9-16 (October 1997); Morea et al., J Mol Biol. 275(2):269-94 (Jan. 1998); Chothia et al., Nature 342(6252):877-83 (December 1989); Ponomarenko and Bourne, BMC Structural Biology 7:64 (2007); each of which is incorporated herein by reference in its entirety. Unless otherwise indicated, Kabat definition is used in the present disclosure.

The CDRs are important for recognizing an epitope of an antigen. As used herein, an "epitope" is the smallest portion of a target molecule capable of being specifically bound by the antigen binding domain of an antibody. The minimal size of an epitope may be about three, four, five, six, or seven amino acids, but these amino acids need not be in a consecutive linear sequence of the antigen's primary structure, as the epitope may depend on an antigen's three-dimensional configuration based on the antigen's secondary and tertiary structure.

In some embodiments, the antibody is an intact immunoglobulin molecule (e.g., IgG1, IgG2a, IgG2b, IgG3, IgM, IgD, IgE, IgA). The IgG subclasses (IgG1, IgG2, IgG3, and IgG4) are highly conserved, differ in their constant region, particularly in their hinges and upper CH2 domains. The sequences and differences of the IgG subclasses are known in the art, and are described, e.g., in Vidarsson, et al, "IgG subclasses and allotypes: from structure to effector functions." Frontiers in immunology 5 (2014); Irani, et al. "Molecular properties of human IgG subclasses and their implications for designing therapeutic monoclonal antibodies against infectious diseases." Molecular immunology 67.2 (2015): 171-182; Shakib, Farouk, ed. The human IgG subclasses: molecular analysis of structure, function and regulation. Elsevier, 2016; each of which is incorporated herein by reference in its entirety.

The antibody can also be an immunoglobulin molecule that is derived from any species (e.g., human, rodent, mouse, camelid). Antibodies disclosed herein also include, but are not limited to, polyclonal, monoclonal, monospecific, polyspecific antibodies, and chimeric antibodies that include an immunoglobulin binding domain fused to another polypeptide. The term "antigen binding domain" or "antigen binding fragment" is a portion of an antibody that retains specific binding activity of the intact antibody, i.e., any portion of an antibody that is capable of specific binding to an epitope on the intact antibody's target molecule. It includes, e.g., Fab, Fab', F(ab')2, and variants of these fragments. Thus, in some embodiments, an antibody or an antigen binding fragment thereof can be, e.g., a scFv, a Fv, a Fd, a dAb, a bispecific antibody, a bispecific scFv, a diabody, a linear antibody, a single-chain antibody molecule, a multi-specific antibody formed from antibody fragments, and any polypeptide that includes a binding domain which is, or is homologous to, an antibody binding domain. Non-limiting examples of antigen binding domains include, e.g., the heavy chain and/or light chain CDRs of an intact antibody, the heavy and/or light chain variable regions of an intact antibody, full length heavy or light chains of an intact antibody, or an individual CDR from either the heavy chain or the light chain of an intact antibody.

Fragments of antibodies are suitable for use in the methods described herein are also provided. The Fab fragment contains a variable and constant domain of the light chain and a variable domain and the first constant domain (CH1) of the heavy chain. F(ab')2 antibody fragments comprise a pair of Fab fragments which are generally covalently linked near their carboxy termini by hinge cysteines between them. Other chemical couplings of antibody fragments are also known in the art.

Diabodies are small antibody fragments with two antigen-binding sites, which fragments comprise a VH connected to a $V_L$ in the same polypeptide chain (VH and $V_L$). By using a linker that is too short to allow pairing between the two domains on the same chain, the domains are forced to pair with the complementary domains of another chain and create two antigen-binding sites.

Linear antibodies comprise a pair of tandem Fd segments (VH-CH1-VH-CH1) which, together with complementary light chain polypeptides, form a pair of antigen binding regions. Linear antibodies can be bispecific or monospecific.

Antibodies and antibody fragments of the present disclosure can be modified in the Fc region to provide desired effector functions or serum half-life.

Multimerization of antibodies may be accomplished through natural aggregation of antibodies or through chemical or recombinant linking techniques known in the art. For example, some percentage of purified antibody preparations (e.g., purified $IgG_1$ molecules) spontaneously form protein aggregates containing antibody homodimers and other higher-order antibody multimers.

Alternatively, antibody homodimers may be formed through chemical linkage techniques known in the art. For example, heterobifunctional crosslinking agents including, but not limited to SMCC (succinimidyl 4-(maleimidomethyl)cyclohexane-1-carboxylate) and SATA (N-succinimidyl S-acethylthio-acetate) can be used to form antibody multimers. An exemplary protocol for the formation of antibody homodimers is described in Ghetie et al. (*Proc. Natl. Acad. Sci. U.S.A.* 94: 7509-7514, 1997). Antibody homodimers can be converted to Fab'2 homodimers through digestion with pepsin. Another way to form antibody homodimers is through the use of the autophilic T15 peptide described in Zhao et al. (*J. Immunol.* 25:396-404, 2002).

In some embodiments, the multi-specific antibody is a bi-specific antibody. Bi-specific antibodies can be made by engineering the interface between a pair of antibody molecules to maximize the percentage of heterodimers that are recovered from recombinant cell culture. For example, the interface can contain at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. This method is described, e.g., in WO 96/27011, which is incorporated by reference in its entirety.

Bi-specific antibodies include cross-linked or "heteroconjugate" antibodies. For example, one of the antibodies in the heteroconjugate can be coupled to avidin and the other to biotin. Heteroconjugate antibodies can also be made using any convenient cross-linking methods. Suitable cross-linking agents and cross-linking techniques are well known in the art and are disclosed in U.S. Pat. No. 4,676,980, which is incorporated herein by reference in its entirety.

Methods for generating bi-specific antibodies from antibody fragments are also known in the art. For example, bi-specific antibodies can be prepared using chemical linkage. Brennan et al. (Science 229:81, 1985) describes a procedure where intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab' TNB derivatives is then reconverted to the Fab' thiol by reduction with mercaptoethylamine, and is mixed with an equimolar amount of another Fab' TNB derivative to form the bi-specific antibody.

Any of the antibodies or antigen-binding fragments described herein may be conjugated to a stabilizing molecule (e.g., a molecule that increases the half-life of the antibody or antigen-binding fragment thereof in a subject or in solution). Non-limiting examples of stabilizing molecules include: a polymer (e.g., a polyethylene glycol) or a protein (e.g., serum albumin, such as human serum albumin). The conjugation of a stabilizing molecule can increase the half-life or extend the biological activity of an antibody or an antigen-binding fragment in vitro (e.g., in tissue culture or when stored as a pharmaceutical composition) or in vivo (e.g., in a human).

In some embodiments, the antibodies or antigen-binding fragments described herein can be conjugated to a therapeutic agent. The antibody-drug conjugate comprising the antibody or antigen-binding fragment thereof can covalently or non-covalently bind to a therapeutic agent. In some embodiments, the therapeutic agent is a cytotoxic or cytostatic agent (e.g., cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4, dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs).

In some embodiments, the antigen binding fragment can form a part of a chimeric antigen receptor (CAR). In some embodiments, the chimeric antigen receptor are fusions of single-chain variable fragments (scFv) as described herein, fused to CD3-zeta transmembrane- and endodomain. In some embodiments, the chimeric antigen receptor also comprises intracellular signaling domains from various costimulatory protein receptors (e.g., CD28, 41BB, ICOS). In some embodiments, the chimeric antigen receptor comprises multiple signaling domains, e.g., CD3z-CD28-41BB or CD3z-CD28-OX40, to increase potency. Thus, in one aspect, the disclosure further provides cells (e.g., T cells) that express the chimeric antigen receptors as described herein.

In some embodiments, the scFV has one heavy chain variable domain, and one light chain variable domain. In some embodiments, the scFV has two heavy chain variable domains, and two light chain variable domains.

Antibody Characteristics

The antibodies or antigen-binding fragments thereof described herein can block the binding between PD-1 and PD-1 ligands (e.g., PD-L1 or PD-L2). In some embodiments, by binding to PD-1, the antibody can inhibit PD-1 signaling pathway. In some embodiments, the antibody can upregulate immune response.

In some embodiments, the antibodies or antigen-binding fragments thereof as described herein can increase immune response, activity or number of immune cells (e.g., T cells, CD8+ T cells, CD4+ T cells, macrophages, antigen presenting cells) by at least 10%, 20%, 30%, 40%, 50%, 60%, 70%, 80%, 90%, 100%, 2 folds, 3 folds, 5 folds, 10 folds, or 20 folds.

In some implementations, the antibody (or antigen-binding fragments thereof) specifically binds to PD-1 (e.g., human PD-1 (SEQ ID NO: 77), Rhesus monkey PD-1 (NP_001107830.1), mouse PD-1 (NP_032824.1), and/or chimeric PD-1) with a dissociation rate (koff) of less than 0.1 s$^{-1}$, less than 0.01 s$^{-1}$, less than 0.001 s$^{-1}$, less than 0.0001 s$^{-1}$, or less than 0.00001 s$^{-1}$. In some embodiments, the dissociation rate (koff) is greater than 0.01 s$^{-1}$, greater than 0.001 s$^{-1}$, greater than 0.0001 s$^{-1}$, greater than 0.00001 s$^{-1}$, or greater than 0.000001 s$^{-1}$.

In some embodiments, kinetic association rates (kon) is greater than $1\times10^2$/Ms, greater than $1\times10^3$/Ms, greater than $1\times10^4$/Ms, greater than $1\times10^5$/Ms, or greater than $1\times10^6$/Ms. In some embodiments, kinetic association rates (kon) is less than $1\times10^5$/Ms, less than $1\times10^6$/Ms, or less than $1\times10^7$/Ms.

Affinities can be deduced from the quotient of the kinetic rate constants (KD=koff/kon). In some embodiments, KD (Kd) is less than $1\times10^{-6}$M, less than $1\times10^{-7}$M, less than $1\times10^{-8}$M, less than $1\times10^{-9}$ M, or less than $1\times10^{-10}$ M. In some embodiments, the KD is less than 50 nM, 30 nM, 20 nM, 15 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. In some embodiments, KD is greater than $1\times10^{-7}$ M, greater than $1\times10^{-8}$ M, greater than $1\times10^{-9}$ M, greater than $1\times10^{-10}$ M, greater than $1\times10^{-11}$M, or greater than $1\times10^{-12}$M.

General techniques for measuring the affinity of an antibody for an antigen include, e.g., ELISA, RIA, and surface plasmon resonance (SPR). In some embodiments, the antibody binds to human PD-1 (SEQ ID NO: 77). In some embodiments, the antibody binds to monkey PD-1 (e.g., NP_001271065.1 from *Macaca fascicularis*), chimeric PD-1, and/or mouse PD-1 (e.g., NP_032824.1). In some embodiments, the antibody does not bind to monkey PD-1, chimeric PD-1, and/or mouse PD-1.

In some embodiments, the antibodies or antigen-binding fragments thereof as described herein are PD-1 antagonist. In some embodiments, the antibodies or antigen binding fragments decrease PD-1 signal transduction in a target cell that expresses PD-1.

In some embodiments, the antibodies or antigen binding fragments can enhance APC (e.g., DC cell) function, for example, inducing surface expression of costimulatory and MHC molecules, inducing production of proinflammatory cytokines, and/or enhancing T cell triggering function.

In some embodiments, the Fc region is human IgG1, human IgG2, human IgG3, or human IgG4. In some embodiments, the antibody is a human IgG1 antibody.

In some embodiments, the antibodies or antigen binding fragments do not have a functional Fc region. For example, the antibodies or antigen binding fragments are Fab, Fab', F(ab')2, and Fv fragments. In some embodiments, the Fc region has LALA mutations (L234A and L235A mutations in EU numbering), or LALA-PG mutations (L234A, L235A, P329G mutations in EU numbering).

The binding of an antibody as described herein to PD-1 can also be assessed using one or more techniques well established in the art. For example, in a preferred embodiment, an antibody can be tested by ELISA assays, for example using a recombinant PD-1 protein. Still other suitable binding assays include but are not limited to a flow cytometry assay in which the antibody is reacted with a cell line that expresses human PD-1, such as HEK293T cells that have been transfected to express PD-1 (e.g., human PD-1) on their cell surface. Additionally or alternatively, the binding of the antibody, including the binding kinetics (e.g., KD value) can be tested in BIAcore binding assays and the like.

Preferably, an antibody of the disclosure binds to a PD-1 protein with an EC50 of $5\times10^{-8}$ M or less, binds to a PD-1 protein with a EC50 of $2\times10^{-8}$M or less, binds to a PD-1 protein with a EC50 of $5\times10^{-9}$ M or less, binds to a PD-1 protein with a EC50 of $4\times10^{-9}$ M or less, binds to a PD-1 protein with a EC50 of $3\times10^{-9}$ M or less, binds to a PD-1 protein with a EC50 of $2\times10^{-9}$M or less, binds to a PD-1 protein with a EC50 of $1\times10^{-9}$ M or less.

Methods of Making Anti-PD-1 Antibodies

An isolated fragment of human PD-1 can be used as an immunogen to generate antibodies using standard techniques for polyclonal and monoclonal antibody preparation. Polyclonal antibodies can be raised in animals by multiple injections (e.g., subcutaneous or intraperitoneal injections) of an antigenic peptide or protein. In some embodiments, the antigenic peptide or protein is injected with at least one adjuvant. In some embodiments, the antigenic peptide or protein can be conjugated to an agent that is immunogenic in the species to be immunized. Animals can be injected with the antigenic peptide or protein more than one time (e.g., twice, three times, or four times).

The full-length polypeptide or protein can be used or, alternatively, antigenic peptide fragments thereof can be used as immunogens. The antigenic peptide of a protein comprises at least 8 (e.g., at least 10, 15, 20, or 30) amino acid residues of the amino acid sequence of PD-1 and encompasses an epitope of the protein such that an antibody raised against the peptide forms a specific immune complex with the protein. As described above, the full length sequence of human PD-1 is known in the art (SEQ ID NO: 77).

An immunogen typically is used to prepare antibodies by immunizing a suitable subject (e.g., human or transgenic animal expressing at least one human immunoglobulin locus). An appropriate immunogenic preparation can contain, for example, a recombinantly-expressed or a chemically-synthesized polypeptide (e.g., a fragment of human PD-1). The preparation can further include an adjuvant, such as Freund's complete or incomplete adjuvant, or a similar immunostimulatory agent.

Polyclonal antibodies can be prepared as described above by immunizing a suitable subject with a PD-1 polypeptide, or an antigenic peptide thereof (e.g., part of PD-1) as an immunogen. The antibody titer in the immunized subject can be monitored over time by standard techniques, such as with an enzyme-linked immunosorbent assay (ELISA) using the immobilized PD-1 polypeptide or peptide. If desired, the antibody molecules can be isolated from the mammal (e.g., from the blood) and further purified by well-known techniques, such as protein A of protein G chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler et al. (*Nature* 256:495-497, 1975), the human B cell hybridoma technique (Kozbor et al., *Immunol. Today* 4:72, 1983), the EBV-hybridoma technique (Cole et al., Monoclonal Antibodies and Cancer Therapy, Alan R. Liss, Inc., pp. 77-96, 1985), or trioma techniques. The technology for producing hybridomas is well known (see, generally, Current Protocols in Immunology, 1994, Coligan et al. (Eds.), John Wiley & Sons, Inc., New York, N.Y.). Hybridoma cells producing a monoclonal antibody are detected by screening the hybridoma culture supernatants for antibodies that bind the polypeptide or epitope of interest, e.g., using a standard ELISA assay.

A nucleic acid molecule encoding the heavy or entire light chain of an anti-PD-1 antibody or portions thereof can be isolated from any source that produces such an antibody. In various embodiments, the nucleic acid molecules are isolated from a B cell isolated from an animal immunized with PD-1 or from an immortalized cell derived from such a B cell that expresses an anti-PD-1 antibody. Methods of isolating mRNA encoding an antibody are well-known in the art. See, e.g., Sambrook et al. The mRNA may be used to produce cDNA for use in the polymerase chain reaction (PCR) or cDNA cloning of antibody genes. In a preferred embodiment, the nucleic acid molecule is isolated from a hybridoma that has as one of its fusion partners a human immunoglobulin producing cell from a non-human transgenic animal. In another embodiment, the nucleic acid can be isolated from a non-human, nontransgenic animal. The nucleic acid molecules isolated from a non-human, non-transgenic animal may be used, e.g., for humanized antibodies.

Variants of the antibodies or antigen-binding fragments described herein can be prepared by introducing appropriate nucleotide changes into the DNA encoding a human, humanized, or chimeric antibody, or antigen-binding fragment thereof described herein, or by peptide synthesis. Such variants include, for example, deletions, insertions, or substitutions of residues within the amino acids sequences that make-up the antigen-binding site of the antibody or an antigen-binding domain. In a population of such variants, some antibodies or antigen-binding fragments will have increased affinity for the target protein, e.g., PD-1. Any combination of deletions, insertions, and/or combinations can be made to arrive at an antibody or antigen-binding fragment thereof that has increased binding affinity for the target. The amino acid changes introduced into the antibody or antigen-binding fragment can also alter or introduce new post-translational modifications into the antibody or antigen-binding fragment, such as changing (e.g., increasing or decreasing) the number of glycosylation sites, changing the type of glycosylation site (e.g., changing the amino acid sequence such that a different sugar is attached by enzymes present in a cell), or introducing new glycosylation sites.

Antibodies disclosed herein can be derived from any species of animal, including mammals. Non-limiting examples of native antibodies include antibodies derived from humans, primates, e.g., monkeys and apes, cows, pigs, horses, sheep, camelids (e.g., camels and llamas), chicken, goats, and rodents (e.g., rats, mice, hamsters and rabbits), including transgenic rodents genetically engineered to produce human antibodies.

Human and humanized antibodies include antibodies having variable and constant regions derived from (or having the same amino acid sequence as those derived from) human germline immunoglobulin sequences. Human antibodies may include amino acid residues not encoded by human germline immunoglobulin sequences (e.g., mutations introduced by random or site-specific mutagenesis in vitro or by somatic mutation in vivo), for example in the CDRs.

A humanized antibody, typically has a human framework (FR) grafted with non-human CDRs. Thus, a humanized antibody has one or more amino acid sequence introduced into it from a source which is non-human. These non-human amino acid residues are often referred to as "import" residues, which are typically taken from an "import" variable domain.

Ordinarily, amino acid sequence variants of the human, humanized, or chimeric anti-PD-1 antibody will contain an amino acid sequence having at least 75%, 80%, 85%, 90%, 95%, 96%, 97%, 98%, or 99% percent identity with a sequence present in the light or heavy chain of the original antibody.

Identity or homology with respect to an original sequence is usually the percentage of amino acid residues present within the candidate sequence that are identical with a sequence present within the human, humanized, or chimeric anti-PD-1 antibody or fragment, after aligning the sequences and introducing gaps, if necessary, to achieve the maximum percent sequence identity, and not considering any conservative substitutions as part of the sequence identity.

Additional modifications to the anti-PD-1 antibodies or antigen-binding fragments can be made. For example, a cysteine residue(s) can be introduced into the Fc region, thereby allowing interchain disulfide bond formation in this region. The homodimeric antibody thus generated may have any increased half-life in vitro and/or in vivo. Homodimeric antibodies with increased half-life in vitro and/or in vivo can also be prepared using heterobifunctional cross-linkers as described, for example, in Wolff et al. Wolff et al. ("Monoclonal antibody homodimers: enhanced antitumor activity in nude mice." Cancer research 53.11 (1993): 2560-2565). Alternatively, an antibody can be engineered which has dual Fc regions.

In some embodiments, a covalent modification can be made to the anti-PD-1 antibody or antigen-binding fragment thereof. These covalent modifications can be made by chemical or enzymatic synthesis, or by enzymatic or chemical cleavage. Other types of covalent modifications of the antibody or antibody fragment are introduced into the molecule by reacting targeted amino acid residues of the antibody or fragment with an organic derivatization agent that is capable of reacting with selected side chains or the N- or C-terminal residues.

In some embodiments, antibody variants are provided having a carbohydrate structure that lacks fucose attached (directly or indirectly) to an Fc region. For example, the amount of fucose in such antibody composition may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues; or position 314 in Kabat numbering); however, Asn297 may also be located about ±3 amino acids upstream or downstream of position 297, i.e., between positions 294 and 300, due to minor sequence variations in antibodies. Such fucosylation variants may have improved ADCC function. In some embodiments, to reduce glycan heterogeneity, the Fc region of the antibody can be further engineered to replace the Asparagine at position 297 with Alanine (N297A).

In some embodiments, to facilitate production efficiency by avoiding Fab-arm exchange, the Fc region of the antibodies was further engineered to replace the serine at position 228 (EU numbering) of IgG4 with proline (S228P). A detailed description regarding S228 mutation is described, e.g., in Silva et al. "The S228P mutation prevents in vivo and in vitro IgG4 Fab-arm exchange as demonstrated using a combination of novel quantitative immunoassays and physiological matrix preparation." Journal of Biological Chemistry 290.9 (2015): 5462-5469, which is incorporated by reference in its entirety.

Recombinant Vectors

The present disclosure also provides recombinant vectors (e.g., an expression vectors) that include an isolated polynucleotide disclosed herein (e.g., a polynucleotide that encodes a polypeptide disclosed herein), host cells into which are introduced the recombinant vectors (i.e., such that the host cells contain the polynucleotide and/or a vector comprising the polynucleotide), and the production of recombinant antibody polypeptides or fragments thereof by recombinant techniques.

As used herein, a "vector" is any construct capable of delivering one or more polynucleotide(s) of interest to a host cell when the vector is introduced to the host cell. An "expression vector" is capable of delivering and expressing the one or more polynucleotide(s) of interest as an encoded polypeptide in a host cell into which the expression vector has been introduced. Thus, in an expression vector, the polynucleotide of interest is positioned for expression in the vector by being operably linked with regulatory elements such as a promoter, enhancer, and/or a poly-A tail, either within the vector or in the genome of the host cell at or near or flanking the integration site of the polynucleotide of interest such that the polynucleotide of interest will be translated in the host cell introduced with the expression vector.

A vector can be introduced into the host cell by methods known in the art, e.g., electroporation, chemical transfection (e.g., DEAE-dextran), transformation, transfection, and infection and/or transduction (e.g., with recombinant virus). Thus, non-limiting examples of vectors include viral vectors (which can be used to generate recombinant virus), naked DNA or RNA, plasmids, cosmids, phage vectors, and DNA or RNA expression vectors associated with cationic condensing agents.

In some implementations, a polynucleotide disclosed herein (e.g., a polynucleotide that encodes a polypeptide disclosed herein) is introduced using a viral expression system (e.g., vaccinia or other pox virus, retrovirus, or adenovirus), which may involve the use of a non-pathogenic (defective), replication competent virus, or may use a replication defective virus. In some embodiments, lentivirus is used to introduce the nucleic acids into the cells.

For expression, the DNA insert comprising an antibody-encoding or polypeptide-encoding polynucleotide disclosed herein can be operatively linked to an appropriate promoter (e.g., a heterologous promoter), such as the phage lambda PL promoter, the E. coli lac, trp and tac promoters, the SV40 early and late promoters and promoters of retroviral LTRs, to name a few. Other suitable promoters are known to the skilled artisan. In some embodiments, the promoter is a cytomegalovirus (CMV) promoter. The expression constructs can further contain sites for transcription initiation, termination and, in the transcribed region, a ribosome binding site for translation. The coding portion of the mature transcripts expressed by the constructs may include a translation initiating at the beginning and a termination codon (UAA, UGA, or UAG) appropriately positioned at the end of the polypeptide to be translated.

As indicated, the expression vectors can include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces, and Salmonella typhimurium cells; fungal cells, such as yeast cells; insect cells such as Drosophila S2 and Spodoptera Sf9 cells; animal cells such as CHO, COS, Bowes melanoma, and HK 293 cells; and plant cells. Appropriate culture mediums and conditions for the host cells described herein are known in the art.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986), which is incorporated herein by reference in its entirety.

Transcription of DNA encoding an antibody of the present disclosure by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at base pairs 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals. In some embodiments, the signal peptide is SEQ ID NO: 78 or SEQ ID NO: 79.

The polypeptide (e.g., antibody) can be expressed in a modified form, such as a fusion protein (e.g., a GST-fusion) or with a histidine-tag, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties can be added to the polypeptide to facilitate purification. Such regions can be removed prior to final preparation of the polypeptide. The addition of peptide moieties to polypeptides to engender secretion or excretion, to improve stability and to facilitate purification, among others, are familiar and routine techniques in the art.

In one aspect, the disclosure provides a nucleic acid that is at least 80%, 85%, 90%, 91%, 92%, 93%, 94%, 95%, 96%, 97%, 98%, 99% identical to SEQ ID NO: 1, 3, 15, 17, 27, 29, 37, 39, 47, 49, 47, 49, 67, or 69.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, or 200 amino acid residues.

In some embodiments, the amino acid sequence (i) comprises an amino acid sequence; or (ii) consists of an amino acid sequence, wherein the amino acid sequence is any one of the sequences as described herein. In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of illustration, the comparison of sequences and determination of percent identity between two sequences can be accomplished using a Blossum 62 scoring matrix with a gap penalty of 12, a gap extend penalty of 4, and a frameshift gap penalty of 5.

Methods of Treatment

The antibodies, antibody compositions and methods of the present disclosure have numerous in vitro and in vivo utilities involving, for example, detection of PD-1 or enhancement of immune response by blockade of PD-1. In a preferred embodiment, the antibodies of the present disclosure are human antibodies. For example, these molecules can be administered to cells in culture, in vitro or ex vivo, or to human subjects, e.g., in vivo, to enhance immunity in a variety of situations. Accordingly, in one aspect, the disclosure provides a method of modifying an immune response in a subject comprising administering to the subject the antibody, or antigen-binding portion thereof, of the disclosure such that the immune response in the subject is modified. Preferably, the response is enhanced, stimulated or up-regulated.

As used herein, the term "subject" is intended to include human and non-human animals. Non-human animals include all vertebrates, e.g. mammals and non-mammals, such as non-human primates, sheep, dogs, cats, cows, horses, chickens, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the T-cell mediated immune response. In a particular embodiment, the methods are particularly suitable for treatment of cancer cells in vivo. To achieve antigen-specific enhancement of immunity, the anti-PD-1 antibodies can be administered together with an antigen of interest. When antibodies to PD-1 are administered together with another agent, the two can be administered in either order or simultaneously.

The disclosure further provides methods for detecting the presence of human PD-1 antigen in a sample, or measuring the amount of human PD-1 antigen, comprising contacting the sample, and a control sample, with a human monoclonal antibody, or an antigen-binding portion thereof, which specifically binds to human PD-1, under conditions that allow for formation of a complex between the antibody or portion thereof and human PD-1. The formation of a complex is then detected, wherein a difference complex formation between the sample compared to the control sample is indicative the presence of human PD-1 antigen in the sample.

Blockade of PD-1 by antibodies can enhance the immune response to cancerous cells in the patient. In one aspect, the present disclosure relates to treatment of a subject in vivo using an anti-PD-1 antibody such that growth of cancerous tumors is inhibited. An anti-PD-1 antibody may be used alone to inhibit the growth of cancerous tumors. Alternatively, an anti-PD-1 antibody may be used in conjunction with other immunogenic agents, standard cancer treatments, or other antibodies, as described below.

Accordingly, in one embodiment, the disclosure provides a method of inhibiting growth of tumor cells in a subject, comprising administering to the subject a therapeutically effective amount of an anti-PD-1 antibody, or antigen-binding portion thereof. Preferably, the antibody is a human anti-PD-1 antibody (such as any of the human anti-human PD-1 antibodies described herein). Additionally or alternatively, the antibody may be a chimeric or humanized anti-PD-1 antibody.

Preferred cancers whose growth may be inhibited using the antibodies of the disclosure include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the disclosure includes refractory or recurrent malignancies whose growth may be inhibited using the antibodies of the disclosure.

Examples of other cancers that may be treated using the methods of the disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al. (2005) Int. Immunol. 17:133-144).

Optionally, antibodies to PD-1 can be combined with an immunogenic agent, such as cancerous cells, purified tumor antigens (including recombinant proteins, peptides, and carbohydrate molecules), cells, and cells transfected with genes encoding immune stimulating cytokines (He et al (2004) J. Immunol. 173:4919-28). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF (discussed further below). In humans, some tumors have been shown to be immuno genie such as melanomas. It is anticipated that by raising the threshold of T cell activation by PD-1 blockade, we may expect to activate tumor responses in the host. PD-1 blockade is likely to be most effective when combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Poon, K. 2000, ASCO Educational Book Spring: 730-738; see also Restifo, N. and Sznol, M., Cancer Vaccines, Ch. 61, pp. 3023-3043 in De Vita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43).

A PD-1 blockade may also be combined with standard cancer treatments. A PD-1 blockade may be effectively combined with chemotherapeutic regimes. In these instances, it may be possible to reduce the dose of chemotherapeutic reagent administered (Mokyr, M. et al. (1998) Cancer Research 58: 5301-5304). An example of such a combination is an anti-PD-1 antibody in combination with decarbazine for the treatment of melanoma. Another example of such a combination is an anti-PD-1 antibody in combination with interleukin-2 (IL-2) for the treatment of melanoma. The scientific rationale behind the combined use of PD-1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-1 blockade through cell death are radiation, surgery, and hormone deprivation. Each of these protocols creates a source of tumor antigen in the host. Angiogenesis inhibitors may also be combined with the PD-1 blockade. Inhibition of angiogenesis leads to tumor cell death which may feed tumor antigen into host antigen presentation pathways.

PD-1 blocking antibodies can also be used in combination with bispecific antibodies that target Fc alpha or Fc gamma receptor-expressing effectors cells to tumor cells (see, e.g., U.S. Pat. Nos. 5,922,845 and 5,837,243). Bispecific antibodies can be used to target two separate antigens. For example anti-Fc receptor/anti-tumor antigen (e.g., Her-2/neu) bispecific antibodies have been used to target macrophages to sites of tumor. This targeting may more effectively activate tumor-specific responses. The T cell arm of these responses would be augmented by the use of PD-1 blockade. Alternatively, antigen may be delivered directly to DCs by the use of bispecific antibodies which bind to a tumor antigen and a dendritic cell-specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) J. Exp. Med. 163: 1037-1050), IL-10 (Howard, M. & O'Garra, A. (1992) Immunology Today 13: 198-200), and Fas ligand (Hahne, M. et al. (1996) Science 274: 1363-1365). Antibodies to each of these entities may be used in combination with anti-PD-1 antibodies of the present disclosure to counteract the effects of the immunosuppressive agent and favor tumor immune responses by the host.

Other antibodies which may be used to activate host immune responsiveness can be used in combination with anti-PD-1. These include molecules on the surface of dendritic cells which activate DC function and antigen presentation. Anti-CD40 antibodies are able to substitute effectively for T cell helper activity (Ridge, J. et al. (1998) Nature 393:474-478) and can be used in conjunction with PD-1 antibodies (Ito, N. et al. (2000) Immunobiology 201 (5) 527-40). Activating antibodies to T cell costimulatory molecules such as CTLA-4 (e.g., U.S. Pat. No. 5,811,097), OX-40 (Weinberg, A. et al. (2000)Immunol 164: 2160-2169), 4-1BB (Melero, I. et al. (1997) Nature Medicine 3: 682-685 (1997), and ICOS (Hutloff, A. et al. (1999) Nature 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-1 blockade can be used to increase the effectiveness of the donor engrafted tumor-specific T cells. There are also several experimental treatment protocols that involve ex vivo activation and expansion of antigen-specific T cells and adoptive transfer of these cells into recipients in order to antigen-specific T cells against tumor (Greenberg, R. & Riddell, S. (1999) Science 285: 546-51). These methods may also be used to activate T cell responses to infectious agents such as CMV. Ex vivo activation in the presence of anti-PD-1 antibodies may be expected to increase the frequency and activity of the adoptively transferred T cells.

In one aspect, the disclosure provides methods for treating a cancer in a subject, methods of reducing the rate of the increase of volume of a tumor in a subject over time, methods of reducing the risk of developing a metastasis, or methods of reducing the risk of developing an additional metastasis in a subject. In some embodiments, the treatment can halt, slow, retard, or inhibit progression of a cancer. In some embodiments, the treatment can result in the reduction of in the number, severity, and/or duration of one or more symptoms of the cancer in a subject.

In some embodiments, the antibody has a tumor growth inhibition percentage (TGI %) that is greater than 10%, 20%, 30%, 40%, 50%, 60%, 70%, 80%, 90%, 100%, 110%, 120%, 130%, 140%, 150%, 160%, 170%, 180%, 190%, or 200%. In some embodiments, the antibody has a tumor growth inhibition percentage that is less than 60%, 70%, 80%, 90%, 100%, 110%, 120%, 130%, 140%, 150%, 160%, 170%, 180%, 190%, or 200%. The TGI % can be determined, e.g., at 3, 4, 5, 6, 7, 8, 9, 10, 11, 12, 13, 14, 15, 16, 17, 18, 19, 20, 21, 22, 23, 24, 25, 26, 27, 28, 29, or 30 days after the treatment starts, or 1, 2, 3, 4, 5, 6, 7, 8, 9, 10, 11, or 12 months after the treatment starts. As used herein, the tumor growth inhibition percentage (TGI %) is calculated using the following formula:

$$TGI\ (\%) = [1-(Ti-T0)/(Vi-V0)] \times 100$$

Ti is the average tumor volume in the treatment group on day i. T0 is the average tumor volume in the treatment group on day zero. Vi is the average tumor volume in the control group on day i. V0 is the average tumor volume in the control group on day zero.

In some embodiments, the tumor inhibitory effects of the antibodies or antigen-binding fragments thereof as described herein are comparable to Pembrolizumab, Nivolumab, or Cemiplimab. In some embodiments, the tumor inhibitory effects of the antibodies or antigen-binding fragments thereof as described herein are at least 10%, 20%, 30%, 40%, 50%, 60%, 70%, 80%, 90%, 1 fold, 2 folds, or 5 folds more than Pembrolizumab, Nivolumab, or Cemiplimab.

In one aspect, the disclosure features methods that include administering a therapeutically effective amount of an antibody or antigen-binding fragment thereof disclosed herein to a subject in need thereof (e.g., a subject having, or identified or diagnosed as having, a cancer), e.g., breast cancer (e.g., triple-negative breast cancer), carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, colorectal cancer, gastric cancer, testicular cancer, thyroid cancer, bladder cancer, urethral cancer, or hematologic malignancy. In some embodiments, the cancer is unresectable melanoma or metastatic melanoma, non-small cell lung carcinoma (NSCLC), small cell lung cancer (SCLC), bladder cancer, or metastatic hormone-refractory prostate cancer. In some embodiments, the subject has a solid tumor. In some embodiments, the cancer is squamous cell carcinoma of the head and neck (SCCHN), renal cell carcinoma (RCC), triple-negative breast cancer (TNBC), or colorectal carcinoma. In some embodiments, the subject has Hodgkin's lymphoma. In some embodiments, the subject has triple-negative breast cancer (TNBC), gastric cancer, urothelial cancer, Merkel-cell carcinoma, or head and neck cancer. In some embodiments, the cancer is melanoma, pancreatic carcinoma, mesothelioma, hematological malignancies, especially Non-Hodgkin's lymphoma, lymphoma, chronic lymphocytic leukemia, or advanced solid tumors.

In some embodiments, the compositions and methods disclosed herein can be used for treatment of patients at risk for a cancer. Patients with cancer can be identified with various methods known in the art.

In one aspect, the disclosure provides methods for treating, preventing, or reducing the risk of developing disorders associated with an abnormal or unwanted immune response, e.g., an autoimmune disorder.

As used herein, by an "effective amount" is meant an amount or dosage sufficient to effect beneficial or desired results including halting, slowing, retarding, or inhibiting progression of a disease, e.g., a cancer. An effective amount will vary depending upon, e.g., an age and a body weight of a subject to which the antibody, antigen binding fragment, antibody-encoding polynucleotide, vector comprising the polynucleotide, and/or compositions thereof is to be administered, a severity of symptoms and a route of administration, and thus administration can be determined on an individual basis.

In some embodiments, one or more additional therapeutic agents can be administered to the subject. In some embodiments, the additional therapeutic agent can comprise one or more therapeutic agents selected from the group consisting of Trabectedin, nab-paclitaxel, Trebananib, Pazopanib, Cediranib, Palbociclib, everolimus, fluoropyrimidine, IFL, regorafenib, Reolysin, Alimta, Zykadia, Sutent, temsirolimus, axitinib, everolimus, sorafenib, Votrient, Pazopanib, IMA-901, AGS-003, cabozantinib, Vinflunine, an Hsp90 inhibitor, Ad-GM-CSF, Temazolomide, IL-2, IFNa, vinblastine, Thalomid, dacarbazine, cyclophosphamide, lenalidomide, azacytidine, lenalidomide, bortezomid, amrubicine, carfilzomib, pralatrexate, and enzastaurin.

In some embodiments, the additional therapeutic agent can comprise one or more anti-cancer drugs (e.g., chemotherapies) selected from the group consisting of Abemaciclib, Abiraterone Acetate, Abraxane, Acalabrutinib, Actemra (Tocilizumab), Adcetris (Brentuximab Vedotin), Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran, Aloxi (Palonosetron Hydrochloride), Alunbrig (Brigatinib), Ameluz (Aminolevulinic Acid Hydrochloride), Amifostine, Aminolevulinic Acid Hydrochloride, Anastrozole, Apalutamide, Aprepitant, Aranesp (Darbepoetin Alfa), Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Asparlas (Calaspargase Pegol-mknl), Atezolizumab, Avastin (Bevacizumab), Avelumab, Axicabtagene Ciloleucel, Axitinib, Azacitidine, Azedra (Iobenguane I 131), Bavencio (Avelumab), Beleodaq (Belinostat), Belinostat, Bendamustine Hydrochloride, Bendeka (Bendamustine Hydrochloride), Besponsa (Inotuzumab Ozogamicin), Bevacizumab, Bexarotene, Bicalutamide, BiCNU (Carmustine), Binimetinib, Bleomycin Sulfate, Blinatumomab, Blincyto (Blinatumomab), Bortezomib, Bosulif (Bosutinib), Bosutinib, Braftovi (Encorafenib), Brentuximab Vedotin, Brigatinib, BuMel, Busulfan, Busulfex (Busulfan), Cabazitaxel, Cablivi (Caplacizumab-yhdp), Cabometyx (Cabozantinib-S-Malate), Cabozantinib-S-Malate, Calaspargase Pegol-mknl, Calquence (Acalabrutinib), Campath (Alemtuzumab), Camptosar (Irinotecan Hydrochloride), Capecitabine, Caplacizumab-yhdp, Carac (Fluorouracil—Topical), Carboplatin, CARBOPLATIN-TAXOL, Carfilzomib, Carmustine, Carmustine Implant, Casodex (Bicalutamide), Cemiplimab-rwlc, Ceritinib, Cerubidine (Daunorubicin Hydrochloride), Cervarix (Recombinant HPV Bivalent Vaccine), Cetuximab, Chlorambucil, CHLORAMBUCIL-PREDNISONE, Cisplatin, Cladribine, Clofarabine, Clolar (Clofarabine), Cobimetinib, Cometriq (Cabozantinib-S-Malate), Copanlisib Hydrochloride, Copiktra (Duvelisib), Cosmegen (Dactinomycin), Cotellic (Cobimetinib), Crizotinib, Cyclophosphamide, Cyramza (Ramucirumab), Cytarabine, Cytarabine Liposome, Cytosar-U (Cytarabine), Dabrafenib, Dacarbazine, Dacogen (Decitabine), Dacomitinib, Dactinomycin, Daratumumab, Darbepoetin Alfa, Darzalex (Daratumumab), Dasatinib, Daunorubicin Hydrochloride, Daunorubicin Hydrochloride and Cytarabine Liposome, Daurismo (Glasdegib Maleate), Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), Durvalumab, Duvelisib, Efudex (Fluorouracil—Topical), Eligard (Leuprolide Acetate), Elitek (Rasburicase), Ellence (Epirubicin Hydrochloride), Elotuzumab, Eloxatin (Oxaliplatin), Eltrombopag Olamine, Elzonris (Tagraxofusp-erzs), Emapalumab-lzsg, Emend (Aprepitant), Empliciti (Elotuzumab), Enasidenib Mesylate, Encorafenib, Enzalutamide, Epirubicin Hydrochloride, Epoetin Alfa, Epogen (Epoetin Alfa), Erbitux (Cetuximab), Eribulin Mesylate, Erivedge (Vismodegib), Erleada (Apalutamide), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista (Raloxifene Hydrochloride), Evomela (Melphalan Hydrochloride), Exemestane, 5-FU (Fluorouracil), Fareston (Toremifene), Farydak (Panobinostat), Faslodex (Fulvestrant), Femara (Letrozole), Filgrastim, Firmagon (Degarelix), Fludarabine Phosphate, Fluoroplex (Fluorouracil—Topical), Fluorouracil Injection, Fluorouracil—Topical, Flutamide, Folotyn (Pralatrexate), Fostamatinib Disodium, Fulvestrant, Fusilev (Leucovorin Calcium), Gamifant (Emapalumab-lzsg), Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gilteritinib Fumarate, Glasdegib Maleate, Gleevec (Imatinib Mesylate), Gliadel Wafer (Carmustine Implant), Glucarpidase, Goserelin Acetate, Granisetron, Granisetron Hydrochloride, Granix (Filgrastim), Halaven (Eribulin Mesylate), Hemangeol (Propranolol Hydrochloride), Herceptin Hylecta (Trastuzumab and Hyaluronidase-oysk), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, Iclusig (Ponatinib Hydrochloride), Idarubicin Hydrochloride, Idelalisib, Idhifa (Enasidenib Mesylate), Ifex (Ifosfamide), Ifosfamide, IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iobenguane I 131, Ipilimumab, Iressa (Gefitinib), Irinotecan Hydrochloride, Irinotecan Hydrochloride Liposome, Istodax (Romidepsin), Ivosidenib, Ixabepilone, Ixazomib Citrate, Ixempra (Ixabepilone), Jakafi (Ruxolitinib Phosphate), Jevtana (Cabazitaxel), Kadcyla (Ado-Trastuzumab Emtansine), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Larotrectinib Sulfate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Levulan Kerastik (Aminolevulinic Acid Hydrochloride), Libtayo (Cemiplimab-rwlc), LipoDox (Doxorubicin Hydrochloride Liposome), Lomustine, Lonsurf (Trifluridine and Tipiracil Hydrochloride), Lorbrena (Lorlatinib), Lorlatinib, Lumoxiti (Moxetumomab Pasudotox-tdfk), Lupron (Leuprolide Acetate), Lupron Depot (Leuprolide Acetate), Lutathera (Lutetium Lu 177-Dotatate), Lutetium (Lu 177-Dotatate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Mektovi (Binimetinib), Melphalan, Melphalan Hydrochloride, Mercaptopurine, Mesna, Mesnex (Mesna), Methotrexate, Methylnaltrexone Bromide, Midostaurin, Mitomycin C, Mitoxantrone Hydrochloride, Mogamulizumab-kpkc, Moxetumomab Pasudotox-tdfk, Mozobil (Plerixafor), Mustargen (Mechlorethamine Hydrochloride), Myleran (Busulfan), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nplate (Romiplostim), Obinutuzumab, Odomzo (Sonidegib), Ofatumumab, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), Osimertinib, Oxaliplatin, Paclitaxel, Paclitaxel Albumin-stabilized Nanoparticle Formulation, Palbociclib, Palifermin, Palonosetron Hydrochloride, Palonosetron Hydrochloride and Netupitant, Pamidronate Disodium, Panitumumab, Panobinostat, Pazopanib Hydrochloride, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Plerixafor, Pomalidomide, Pomalyst (Pomalidomide), Ponatinib Hydrochloride, Portrazza (Necitumumab), Poteligeo (Mogamulizumab-kpkc), Pralatrexate, Prednisone, Procarbazine Hydrochloride, Procrit (Epoetin Alfa), Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, Ravulizumab-cwvz, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), Retacrit (Epoetin Alfa), Revlimid (Lenalidomide), Rheumatrex (Methotrexate), Ribociclib, Rittman (Rituximab), Rituxan Hycela (Rituximab and Hyaluronidase Human), Rituximab, Rituximab and Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sancuso (Granisetron), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), Sterile Talc Powder (Talc), Steritalc (Talc), Stivarga (Regorafenib), Sunitinib Malate, Sustol (Granisetron), Sutent (Sunitinib Malate), Sylatron (Peginterferon Alfa-2b), Sylvant (Siltuximab), Synribo (Omacetaxine Mepesuccinate), Tabloid (Thioguanine), Tafinlar (Dabrafenib), Tagraxofusp-erzs, Tagrisso (Osimertinib), Talazoparib Tosylate, Talimogene Laherparepvec, Talzenna (Talazoparib Tosylate), Tamoxifen Citrate, Tarabine PFS (Cytarabine), Tarceva (Erlotinib Hydrochloride), Targretin (Bexarotene), Tasigna (Nilotinib), Tavalisse (Fostamatinib Disodium), Taxol (Paclitaxel), Taxotere (Docetaxel), Tecentriq (Atezolizumab), Temodar (Temozolomide), Temozolomide, Temsirolimus, Thalidomide, Thalomid (Thalidomide), Thioguanine, Thiotepa, Tibsovo (Ivosidenib), Tisagenlecleucel, Tocilizumab, Tolak (Fluorouracil—Topical), Topotecan Hydrochloride, Toremifene, Torisel (Temsirolimus), Totect (Dexrazoxane Hydrochloride), Trabectedin, Trametinib, Trastuzumab, Trastuzumab and Hyaluronidase-oysk, Treanda (Bendamustine Hydrochloride), Trexall (Methotrexate), Trifluridine and Tipiracil Hydrochloride, Trisenox (Arsenic Trioxide), Tykerb (Lapatinib Ditosylate), Ultomiris (Ravulizumab-cwvz), Unituxin (Dinutuximab), Uridine Triacetate, Valrubicin, Valstar (Valrubicin), Vandetanib, VAMP, Varubi (Rolapitant Hydrochloride), Vectibix (Panitumumab), VeIP, Velcade (Bortezomib), Vemurafenib, Venclexta (Venetoclax), Venetoclax, Verzenio (Abemaciclib), Vidaza (Azacitidine), Vinblastine Sulfate, Vincristine Sulfate, Vincristine Sulfate Liposome, Vinorelbine Tartrate, Vismodegib, Vistogard (Uridine Triacetate), Vitrakvi (Larotrectinib Sulfate), Vizimpro (Dacomitinib), Voraxaze (Glucarpidase), Vorinostat, Votrient (Pazopanib Hydrochloride), Vyxeos (Daunorubicin Hydrochloride and Cytarabine Liposome), Xalkori (Crizotinib), Xeloda (Capecitabine), Xgeva (Denosumab), Xofigo (Radium 223 Dichloride), Xospata (Gilteritinib Fumarate), Xtandi (Enzalutamide), Yervoy (Ipilimumab), Yescarta (Axicabtagene Ciloleucel), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), or Zytiga (Abiraterone Acetate). Many of these anti-cancer drugs, including their dosage information, are described on the National Cancer Institute website, which is incorporated by reference in their entirety.

In some embodiments, the chemotherapeutic agent is 5-fluorouracil, bleomycin, capecitabine, cisplatin, cyclophosphamide, dacarbazine, doxorubicin, etoposide, folinic acid, methotrexate, oxaliplatin, prednisolone, procarbazine, vinblastine, vinorelbine, docetaxel, epirubicin, or mustine.

In some embodiments, the method as described herein can increase the efficacy of the anti-cancer drug (e.g., chemotherapy) by at least 50%, 60%, 70%, 80%, 90%, 1 fold, 2 folds, 3 folds, or 5 folds (e.g., as compared to the efficacy when only the anti-cancer drug is administered to the subject at the same dose). Because the efficacy of the anti-cancer drug has been improved, in some embodiments, the therapeutically effective dose of the anti-cancer drug (e.g., chemotherapeutic agent) is about or at least 10%, 20%, 30%, 40%, or 50% lower than a typical dose (e.g., an FDA-approved dose) for the anti-cancer drug, thereby minimizing side effects. In addition, because the efficacy of the anti-cancer drug has been improved, in some embodiments, the therapeutically effective dose of the anti-cancer drug can be administered to the subject less frequently. For example, during a treatment period, the interval between administrations can be increased by about or at least 10%, 20%, 30%, 40%, 50%, 60%, 70%, 80%, 90%, 1 fold, 2 folds, 3 folds, or 5 folds than the administration interval in an FDA-approved treatment plan for the anti-cancer drug. In some embodiments, the total number of administrations can be reduced in a treatment period. For example, the total number of administrations can be reduced by about or at least 10%, 20%, 30%, 40%, or 50%. In some embodiments, because of the improved efficacy, the length of the treatment period can be shortened, e.g., by about or at least 10%, 20%, 30%, 40%, or 50% than the length of an FDA-approved treatment plan.

In some embodiments, the additional therapeutic agent can be adoptive cell therapies. Adoptive cell therapies include a type of immunotherapy in which T cells (a type of immune cell) are given to a patient to help the body fight diseases, such as cancer. In cancer therapy, T cells are usually taken from the patient's own blood or tumor tissue, grown in large numbers in the laboratory, and then given back to the patient to help the immune system fight the cancer. In some embodiments, the adoptive cell therapies include chimeric antigen receptor T-cell (CAR T-cell) therapy, tumor-infiltrating lymphocyte (TIL) therapy, engineered TCR therapy, or natural killer (NK) cell therapy. In some embodiments, the adoptive cell therapies can be called adoptive cell transfer, cellular adoptive immunotherapy, or T-cell transfer therapy.

In some embodiments, the additional therapeutic agent can comprise one or more therapeutic agents selected from the group consisting of an adjuvant, a TLR agonist, tumor necrosis factor (TNF) alpha, IL-1, HMGB1, an IL-10 antagonist, an IL-4 antagonist, an IL-13 antagonist, an IL-17 antagonist, an HVEM antagonist, an ICOS agonist, a treatment targeting CX3CL1, a treatment targeting CXCL9, a treatment targeting CXCL10, a treatment targeting CCL5, an LFA-1 agonist, an ICAM1 agonist, and a Selectin agonist.

In some embodiments, carboplatin, nab-paclitaxel, paclitaxel, cisplatin, pemetrexed, gemcitabine, FOLFOX, or FOLFIRI are administered to the subject.

In some embodiments, the additional therapeutic agent is an anti-OX40 antibody, an anti-PD-1 antibody, an anti-PD-L1 antibody, an anti-PD-L2 antibody, an anti-LAG-3 antibody, an anti-TIGIT antibody, an anti-BTLA antibody, an anti-CTLA-4 antibody, or an anti-GITR antibody.

Treating Infectious Diseases

The disclosure also provides methods of treating patients that have been exposed to toxins or pathogens. Accordingly, another aspect of the disclosure provides a method of treating an infectious disease in a subject, comprising administering to the subject an anti-PD-1 antibody, or antigen-binding portion thereof, such that the subject is treated for the infectious disease. Preferably, the antibody is a human anti-human PD-1 antibody (such as any of the human anti-PD-1 antibodies described herein). Additionally or alternatively, the antibody can be a chimeric or humanized antibody.

Similar to the use as discussed above, antibody mediated PD-1 blockade can be used alone, or as an adjuvant, in combination with vaccines, to stimulate the immune response to pathogens, toxins, and self-antigens. Examples of pathogens for which this therapeutic approach can be used, include, e.g., pathogens for which there is currently no effective vaccine, or pathogens for which conventional vaccines are not completely effective. These include, but are not limited to HIV, Hepatitis (A, B, or C), Influenza, Herpes, Giardia, Malaria, *Leishmania, Staphylococcus aureus, Pseudomonas Aeruginosa*. The PD-1 blockade is particularly useful against established infections by pathogens such as HIV that present mutated antigens over the course of the infections. These new epitopes can be recognized by the immune system when the anti-human PD-1 antibody is administered to the subject, thus provoking a strong T cell response that is not dampened by negative signals through PD-1.

Some examples of pathogenic viruses causing infections treatable by methods of the disclosure include HIV, hepatitis (A, B, or C), herpes virus (e.g., VZV, HSV-1, HAV-6, HSY-II, and CMY, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include *chlamydia, rickettsia* bacteria, mycobacteria, staphylococci, streptococci, pneumonococci, meningococci and gonococci, *klebsiella, proteus, serratia, pseudomonas, legionella*, diphtheria, *salmonella*, bacilli, cholera, tetanus, botulism, anthrax, plague, leptospirosis, and Lymes disease bacteria.

Some examples of pathogenic fungi causing infections treatable by methods of the disclosure include *Candida (albicans, krusei, glabrata, tropicalis,* etc.), *Cryptococcus neoformans, Aspergillus (fumigatus, niger,* etc.), Genus Mucorales *(mucor, absidia,* rhizophus), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the disclosure include *Entamoeba histolytica, Balantidium coli, Naegleriafowleri, Acanthamoeba* sp., *Giardia Zambia, Cryptosporidium* sp., *Pneumocystis carinii, Plasmodium vivax, Babesia microti, Trypanosoma brucei, Trypanosoma cruzi, Leishmania donovani, Toxoplasma gondi,* and *Nippostrongylus brasiliensis*.

In all of the above methods, PD-1 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Bolliger (1993) Proc. Natl. Acad. Sci. USA 90:6444-6448; Poljak (1994) Structure 2:1121-1123).

Bispecific antibodies or antigen-binding fragments can be produced by a variety of methods including fusion of hybridomas or linking of Fab' fragments. See, e.g., Songsivilai & Lachmarm, Clin. Exp. Immunol. 79: 315-321 (1990), Kostelny et al., J. Immunol. 148:1547-1553 (1992). In addition, bispecific antibodies can be formed as "diabodies" or "Janusins." In some embodiments, the bispecific antibody binds to two different epitopes of PD-1. In some embodiments, the bispecific antibody has a first heavy chain and a first light chain from a monoclonal antibody of hybridoma clone #11, and an additional antibody heavy chain and light chain. In some embodiments, the additional light chain and heavy chain also are from one of the above-identified monoclonal antibodies, but can be different from the first heavy and light chains.

Pharmaceutical Formulations

In another aspect, the present disclosure provides a composition, e.g., a pharmaceutical composition, containing one or a combination of monoclonal antibodies, or antigen-binding portion(s) thereof, of the present disclosure, formulated together with a pharmaceutically acceptable carrier. Such compositions may include one or a combination of (e.g., two or more different) antibodies, or immunoconjugates or bispecific molecules of the disclosure. For example, a pharmaceutical composition of the disclosure can comprise a combination of antibodies (or immunoconjugates or bispecific antibodies) that bind to different epitopes on the target antigen or that have complementary activities.

Pharmaceutical compositions of the disclosure also can be administered in combination therapy, i.e., combined with other agents. For example, the combination therapy can include an anti-PD-1 antibody of the present disclosure combined with at least one other anti-inflammatory or immunosuppressant agent. Examples of therapeutic agents that can be used in combination therapy are described in greater detail below in the section on uses of the antibodies of the disclosure.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The pharmaceutical compositions of the disclosure may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions. Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-PD-1 antibody of the disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-PD-1 antibody of the disclosure preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

In another aspect, the instant disclosure provides a pharmaceutical kit of parts comprising an anti-PD-1 antibody and an anti-CTLA-4 antibody, as described herein. The kit may also further comprise instructions for use in the treatment of a hyperproliferative disease (such as cancer as described herein). In another embodiment, the anti-PD-1 and anti-CTLA-4 antibodies may be co-packaged in unit dosage form.

In certain embodiments, two or more monoclonal antibodies with different binding specificities (e.g., anti-PD-1 and anti-CTLA-4) are administered simultaneously, in which case the dosage of each antibody administered falls within the ranges indicated. Antibody can be administered as a single dose or more commonly can be administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

A composition of the present disclosure can be administered via one or more routes of administration using one or more of a variety of methods known in the art. As will be appreciated by the skilled artisan, the route and/or mode of administration will vary depending upon the desired results. Preferred routes of administration for antibodies of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and poly lactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a preferred embodiment, a therapeutic composition of the disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the disclosure can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEES Lett. 357: 140; M. Owais et al. (1995) Antimicrob. Agents Chemother. 39: 180); surfactant protein A receptor (Briscoe et al. (1995) Am. J. Physiol. 1233:134); p120 (Schreier et al. (1994) J. Biol. Chem. 269:9090); see also K. Keinanen; M. L. Laukkanen (1994)FEBS Lett. 346:123; J. J. Killion; I. J. Fidler (1994) Immunomethods 4:273.

Also provided herein are pharmaceutical compositions that contain at least one (e.g., one, two, three, or four) of the antibodies or antigen-binding fragments described herein. Two or more (e.g., two, three, or four) of any of the antibodies or antigen-binding fragments described herein can be present in a pharmaceutical composition in any combination. The pharmaceutical compositions may be formulated in any manner known in the art.

The pharmaceutical compositions can be included in a container, pack, or dispenser together with instructions for administration. The disclosure also provides methods of manufacturing the antibodies or antigen binding fragments thereof for various uses as described herein.

EXAMPLES

The invention is further described in the following examples, which do not limit the scope of the invention described in the claims.

Example 1. Generating Mouse Anti-PD-1 Antibodies

Experiments were performed to generate mouse antibodies against human PD-1. Mice were immunized with human PD-1. Spleen cells were collected. Hybridomas were screened for binding affinities. A hybridoma (clone #11) was selected for further experiments. The sequences of the antibodies were determined by sequencing (F02).

Western Blot analysis was performed with the anti-PD-1 antibody obtained from the selected hybridoma (clone #11) (FIG. 1). HEK-293T cells were purchased from American Type Culture Collection (ATCC). HEK-293T cells were transfected with the pCMV6-ENTRY control (Left lane) or pCMV6-ENTRY with PDCD1 cDNA (Origene, Cat #RC210364; Right lane) for 48 hours and lysed. Equivalent amounts of cell lysates (5 µg per lane) were separated by SDS-PAGE and immunoblotted with the anti-PD-1 antibodies (1:2000). The results show that the anti-PD-1 antibodies can bind to human PD-1 with high affinity.

Example 2. Immunofluorescent Staining

Immunofluorescent staining was performed on cells expressing human PD-1. 293T-PD-1 cells were produced by lentiviral transduction of HEK-293T cells with a vector expressing human PD-1. Cells were cultured in Dulbecco's Modified Eagle Medium (DMEM) supplemented with 10% Fetal bovine serum (FBS).

Figures 2A, 2B:
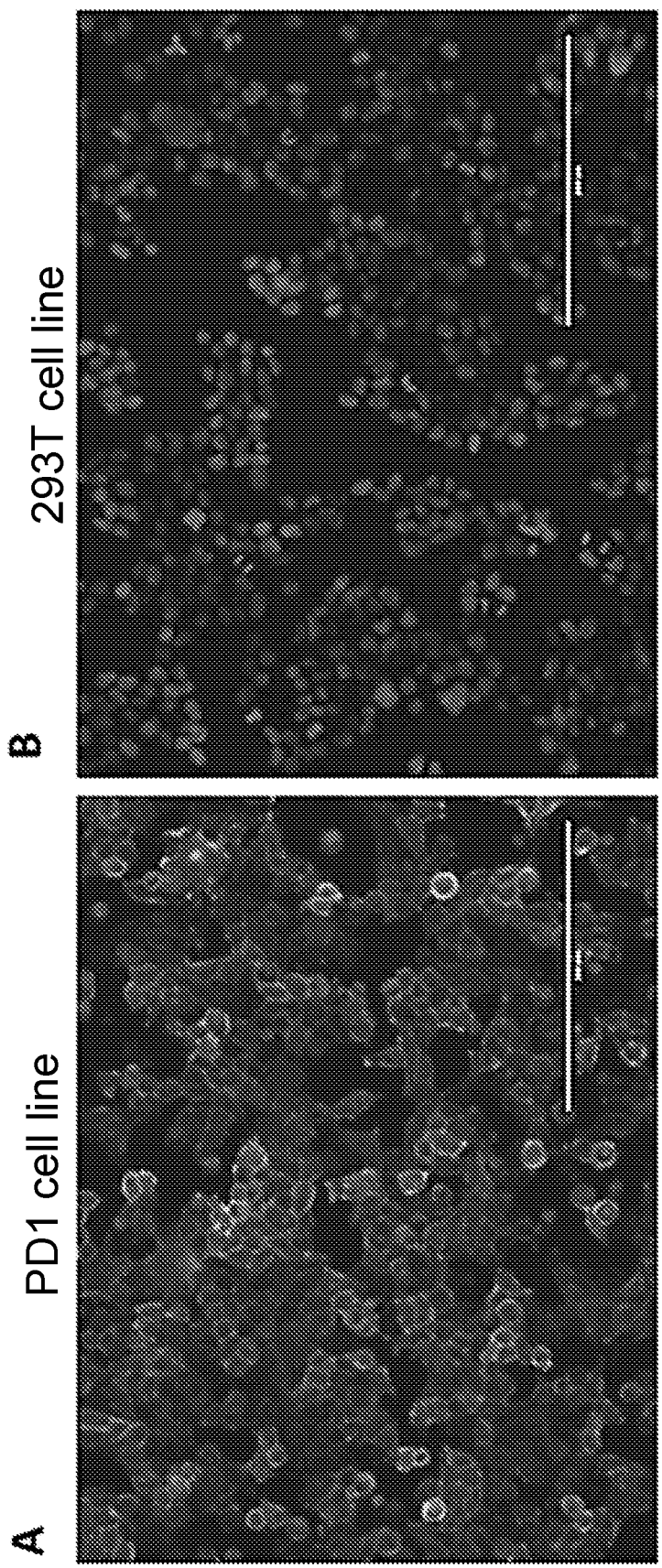
FIG. 2A shows the immunofluorescent staining of PDCD1 (RC210364)-stable-transfected HEK293T cells. PD-1 was labeled by mouse monoclonal anti-PD-1 antibody and the nucleus was labeled with Hoechst33342.
FIG. 2B shows the immunofluorescent staining of HEK293T cells as a negative control (1:100).

FIG. 2A shows the immunofluorescent staining of PDCD1 on RC210364-stable-transfected HEK293T cells with mouse monoclonal antibody anti-PD-1. The nucleus was labeled with Hoechst33342. The same experiments were performed on HEK293T cells as a negative control (1:100) (FIG. 2B).

Figures 3A, 3B:
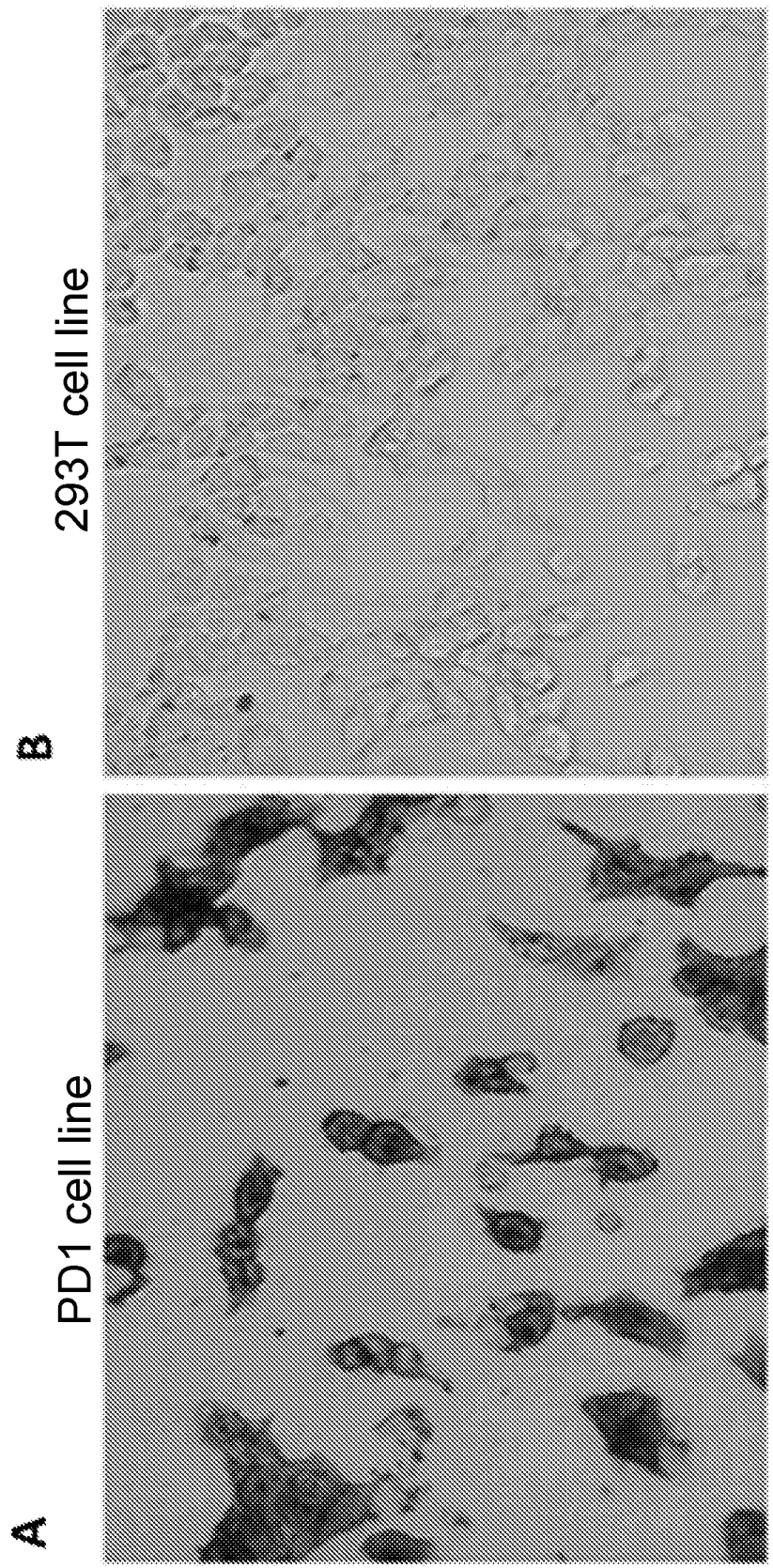
FIG. 3A shows immunocytochemistry staining of cells stably expressing PD-1 using the anti-PD-1 mouse monoclonal antibody (Left).
FIG. 3B shows immunocytochemistry staining of 293T cells as a negative control (1:900).

FIG. 3A shows immunocytochemistry staining of stable expression PD1 cells using anti-PD-1 mouse monoclonal antibody. FIG. 3B shows immunocytochemistry staining of 293T cells as a negative control (1:900).

Figure 4:
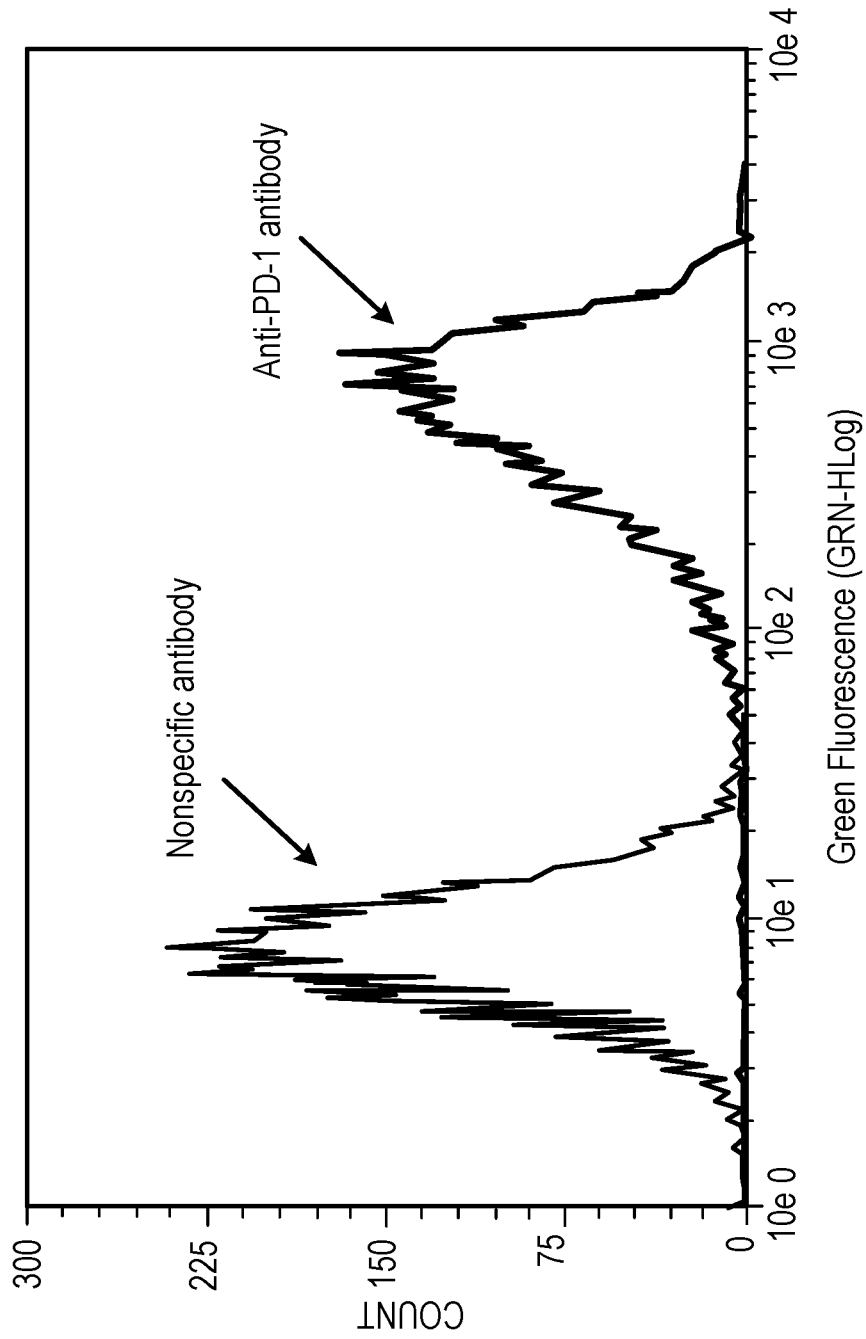
FIG. 4 shows flow cytometric analysis of cells stably expressing PD-1 using anti-PD-1 antibody (F02) compared to a nonspecific negative control antibody (1:50).

Flow cytometric analysis was also performed on cells expressing PD-1 using anti-PD-1 antibody and a nonspecific control antibody (1:50) (FIG. 4).

Figure 5:
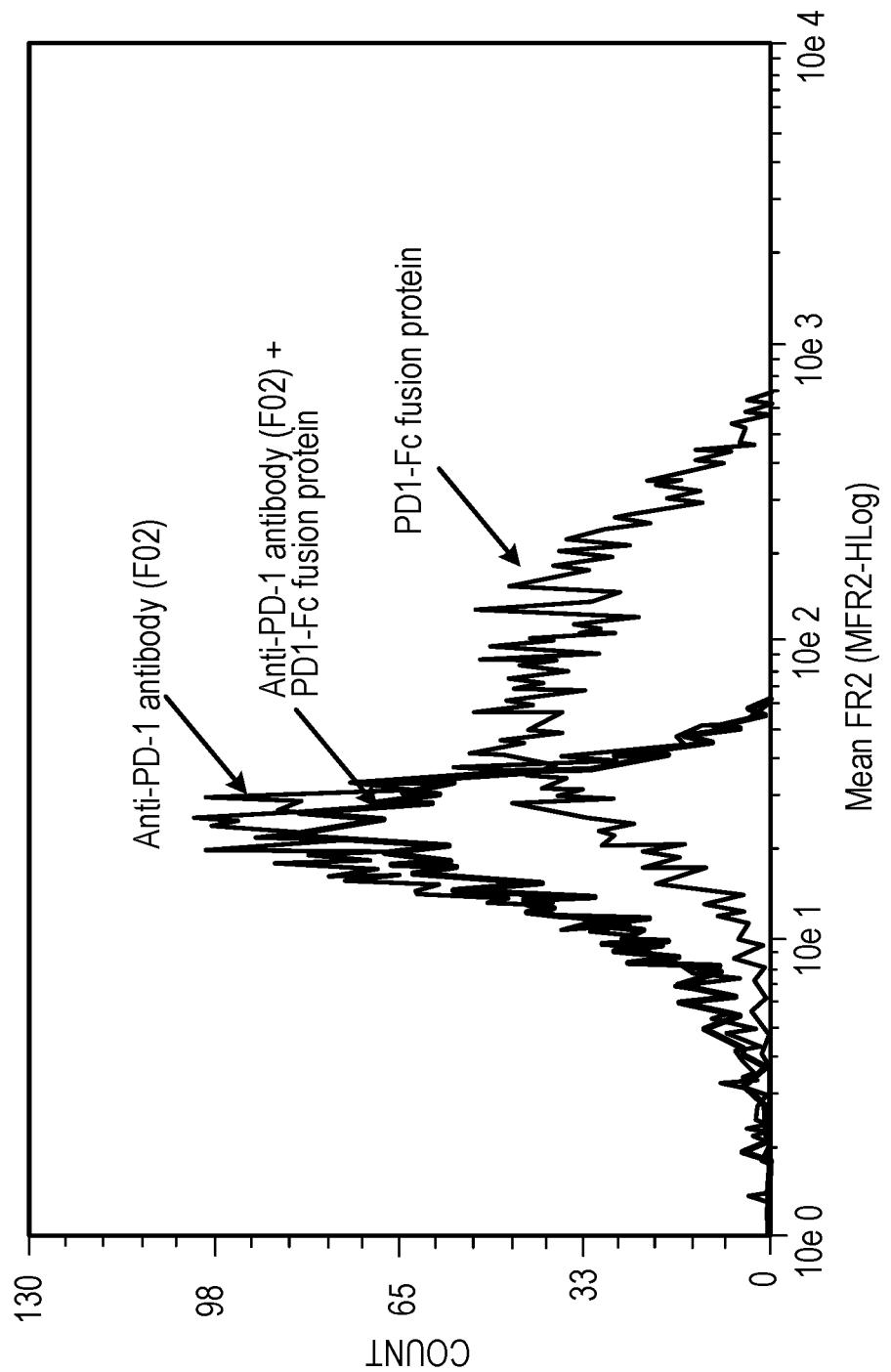
FIG. 5 shows flow cytometric analysis of cells stably expressing PD-L1 (RC213071) using anti-PD-1 antibody from hybridoma clone #11 (F02) or 0.3 ug/ml PD1-Fc fusion protein (TP700199) or both, and detected by anti-Fc (human) IgG-FITC (1:50). Binding of PD-L1 to PD-1 was completely blocked by anti-PD-1 antibody from hybridoma clone #11.

FIG. 5 shows flow cytometric analysis of cells with stable expression of PD-L1 (Origene, Cat #RC213071) using anti-PD-1 antibody from hybridoma clone #11 (F02) or 0.3 ug/ml PD1-Fc fusion protein (TP700199) or both, and detected by anti-Fc (human) IgG-FITC (1:50). Binding of PD-L1 to PD-1 was completely blocked by anti-PD-1 antibody from hybridoma clone #11. The result shows that the anti-PD-1 antibody can effectively block the binding of PD-L1 to PD-1.

Figure 6:
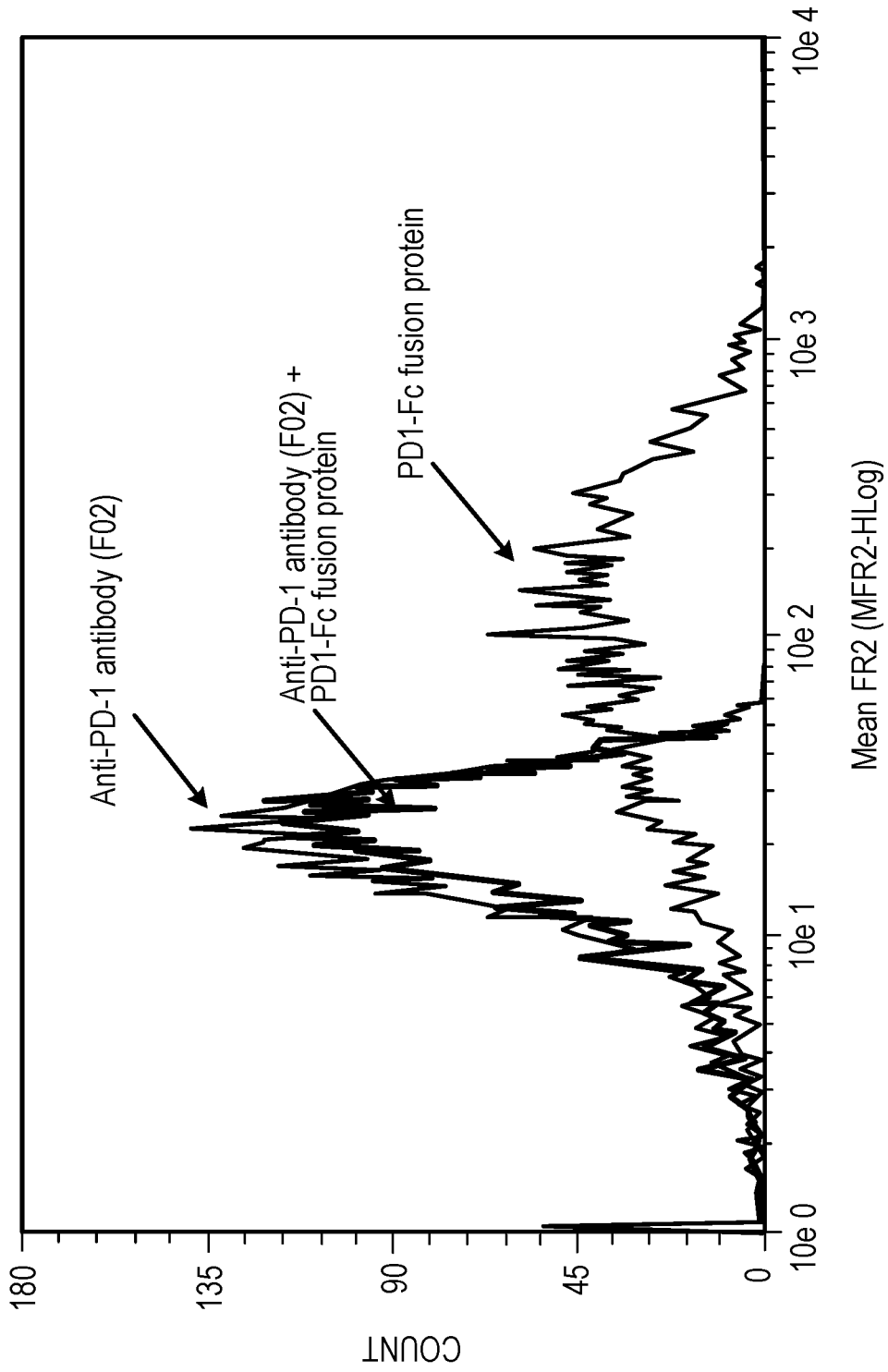
FIG. 6 shows flow cytometric analysis of PD-L2 (RC224141) transiently transfected HEK293T cells using anti-PD-1 antibody from hybridoma clone #11 (F02) or 1 µg/ml PD1-Fc fusion protein (TP700199) or both, and detected by anti-Fc (human) IgG-FITC (1:50). Binding of PD-L2 to PD-1 was completely blocked by anti-PD-1 antibody from hybridoma clone #11.
Figure 7A:
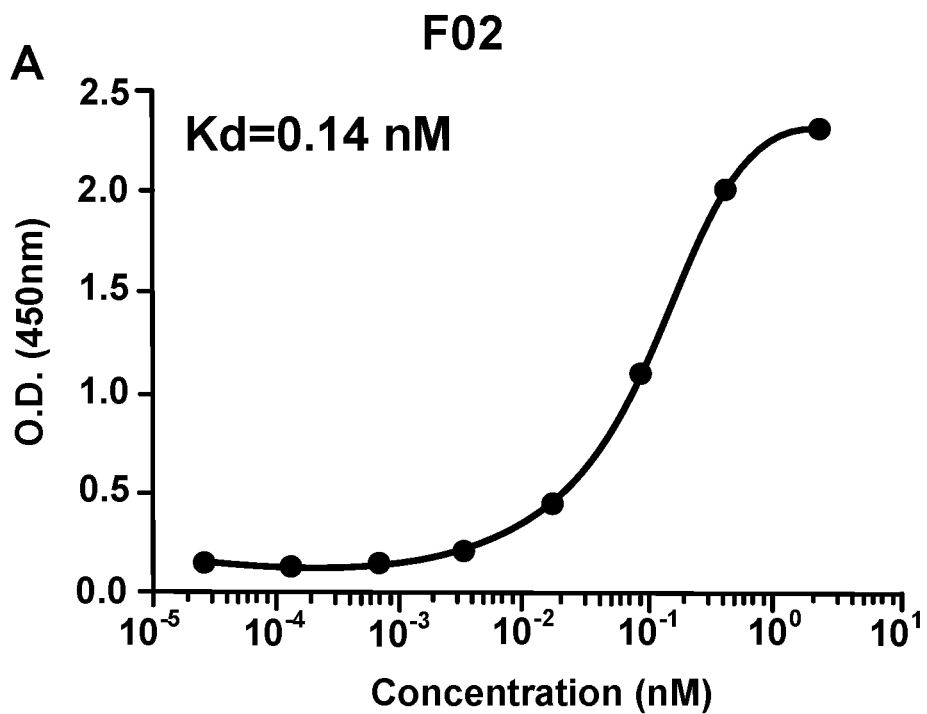
FIG. 7A shows a binding curve between F02 anti-PD-1 antibody and recombinant human PD-1 protein (rhPD-1). The binding affinity of F02 to rhPD-1 was determined by ELISA measurement. Kd value was determined as 0.14 nM.
Figure 7B:
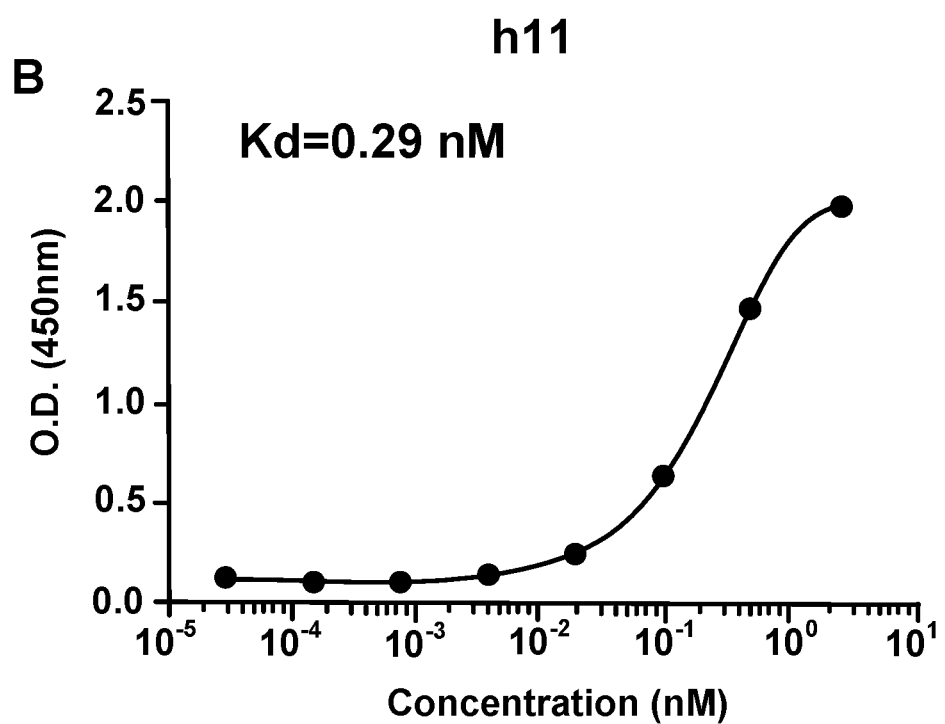
FIG. 7B shows a binding curve between h11 anti-PD-1 antibody and rhPD-1. The binding affinity of h11 to rhPD-1 was determined by ELISA measurement. Kd value was determined as 0.29 nM.
Figure 7C:
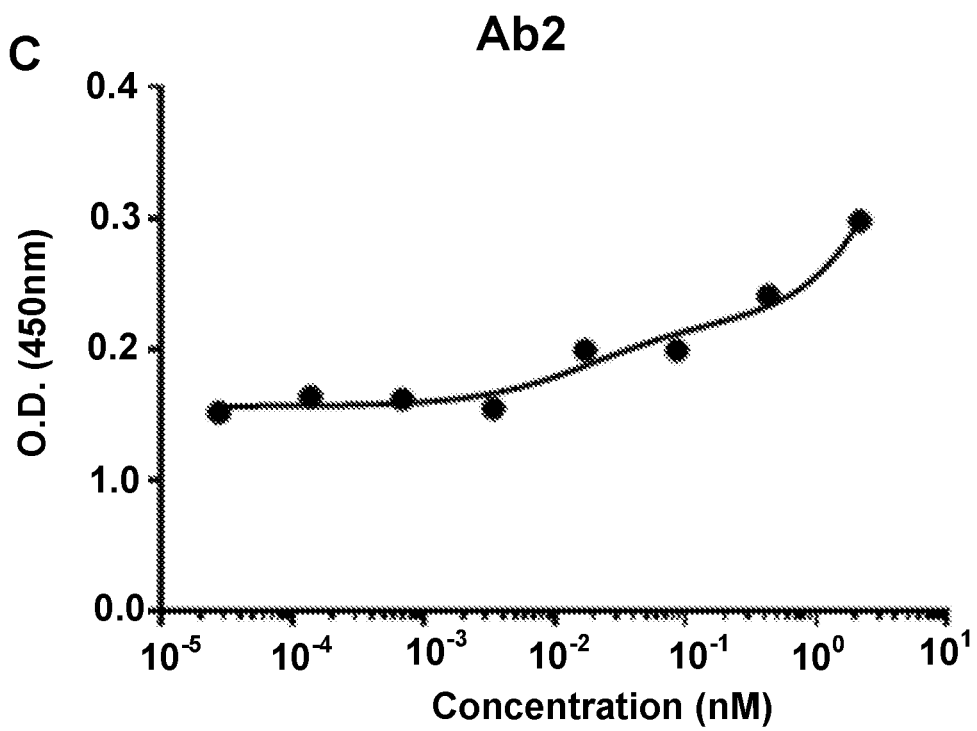
FIG. 7C shows a binding curve between Ab2 anti-PD-1 antibody and rhPD-1.
Figure 7D:
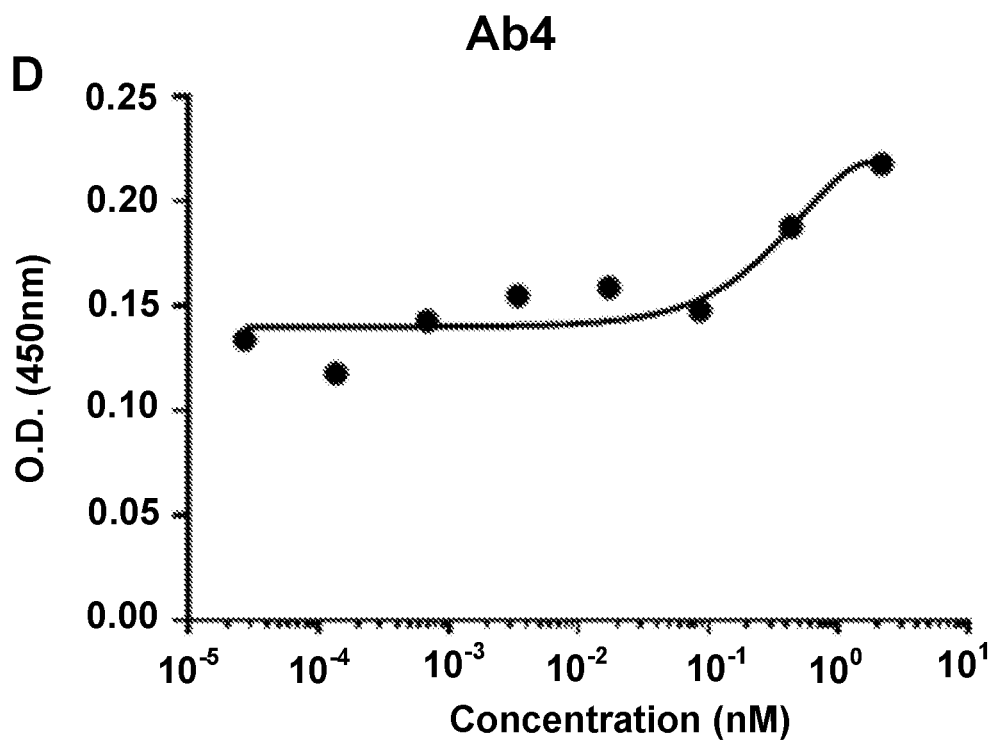
FIG. 7D shows a binding curve between Ab4 anti-PD-1 antibody and rhPD-1.
Figure 7E:
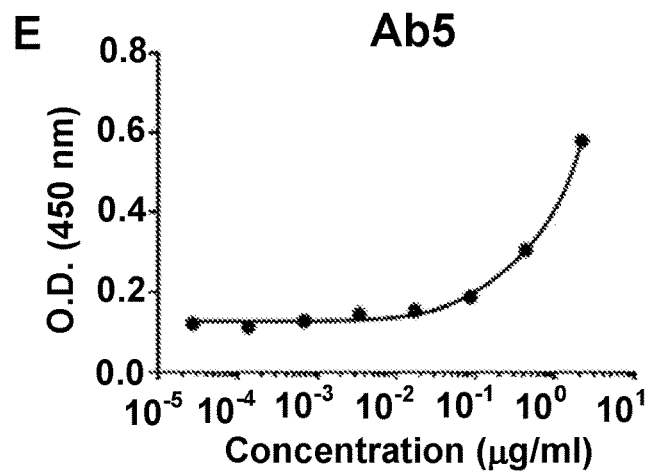
FIG. 7E shows a binding curve between Ab5 anti-PD-1 antibody and rhPD-1.
Figure 7F:
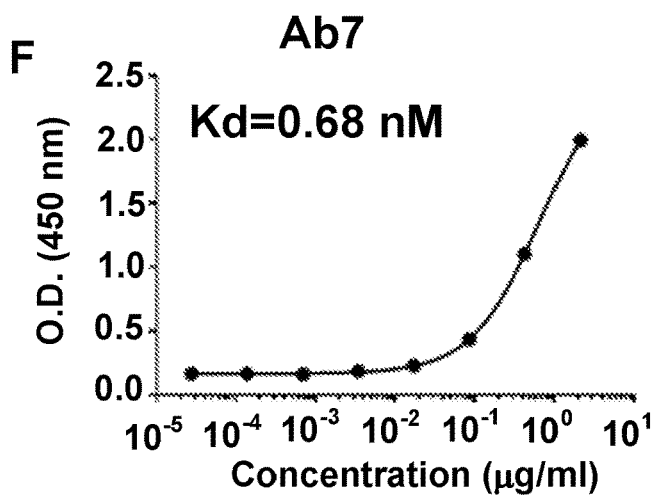
FIG. 7F shows a binding curve between Ab7 anti-PD-1 antibody and rhPD-1. Kd value was determined as 0.68 nM.
Figure 7G:
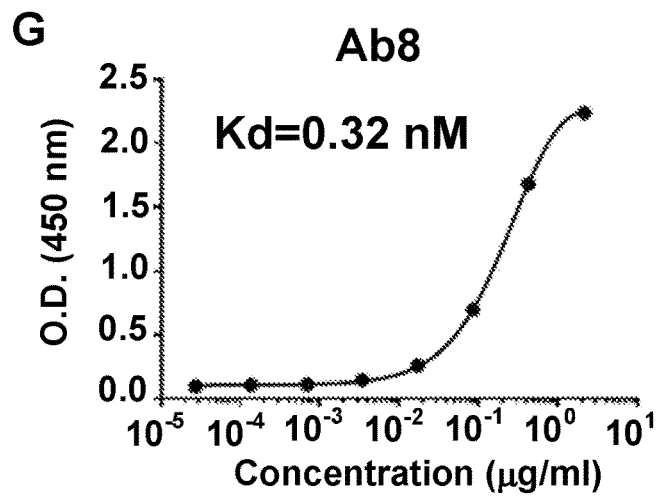
FIG. 7G shows a binding curve between Ab8 anti-PD-1 antibody and rhPD-1. Kd value was determined as 0.32 nM.
Figure 8A:
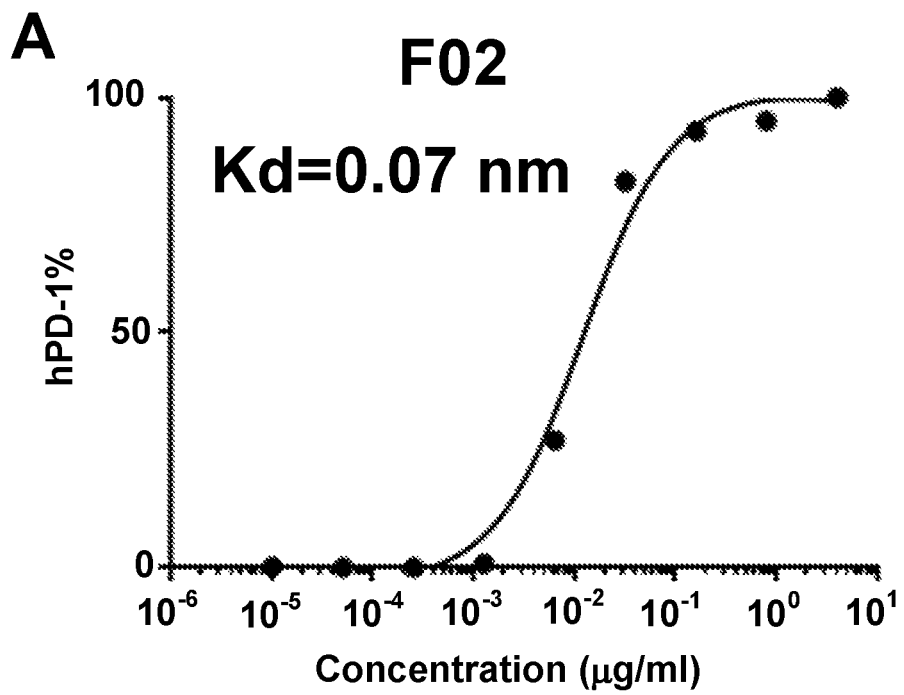
FIG. 8A shows a binding curve between F02 anti-PD-1 antibody and human PD-1 protein (hPD-1) on cell surface. The binding affinity of F02 to hPD-1 on cell surface was determined by flow cytometry assessment. Kd value was determined as 0.07 nM.
Figure 8B:
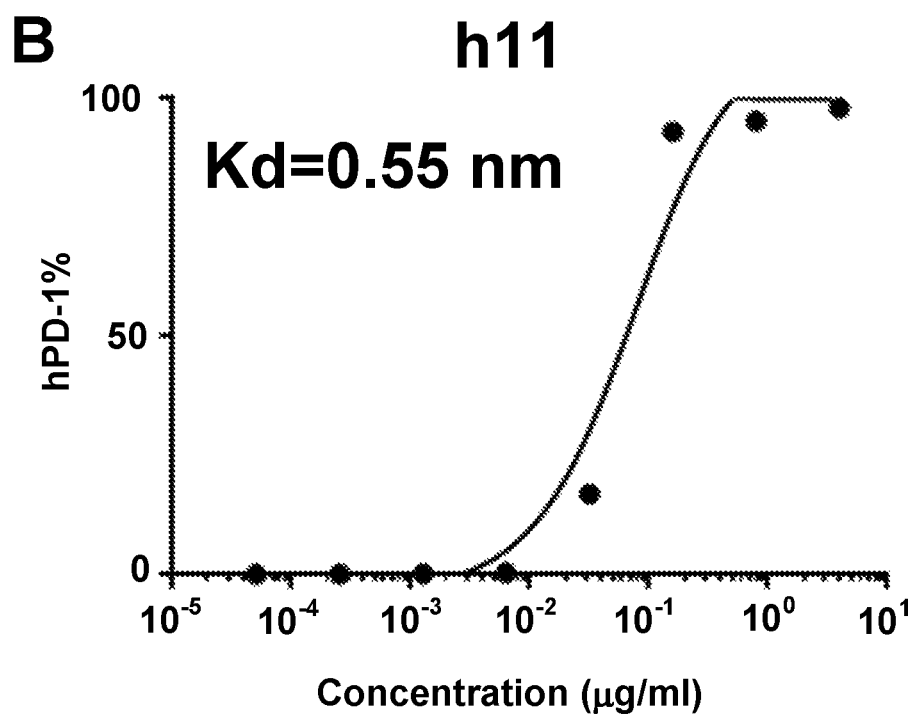
FIG. 8B shows a binding curve between h11 anti-PD-1 antibody and human PD-1 protein (hPD-1) on cell surface. The binding affinity of h11 to hPD-1 on cell surface was determined by flow cytometry assessment. Kd value was determined as 0.55 nM.
Figure 8C:
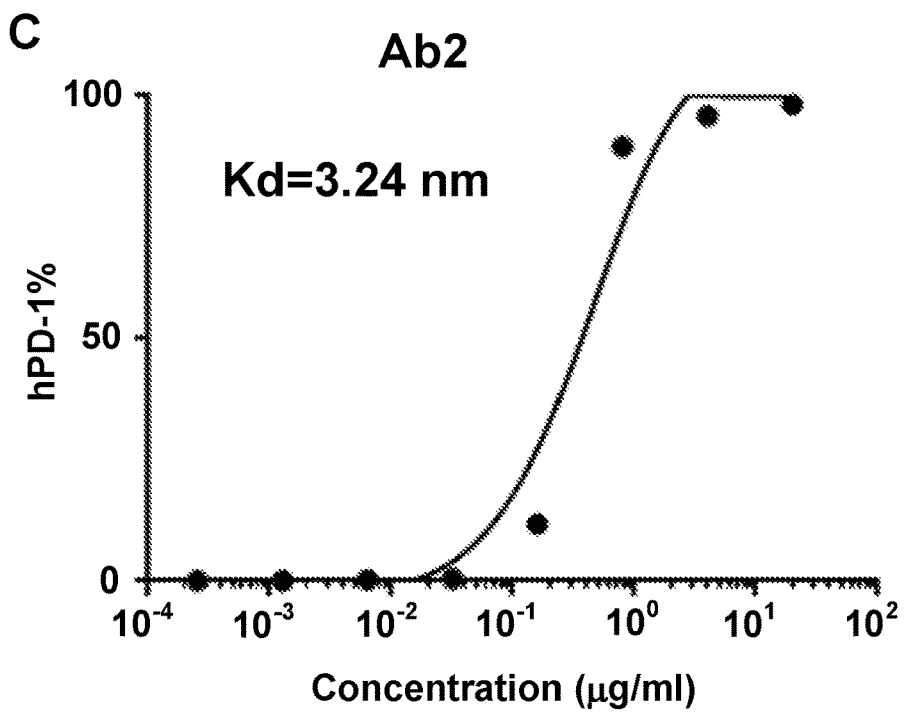
FIG. 8C shows a binding curve between Ab2 anti-PD-1 antibody and human PD-1 protein (hPD-1) on cell surface. Kd value was determined as 3.24 nM.
Figure 8D:
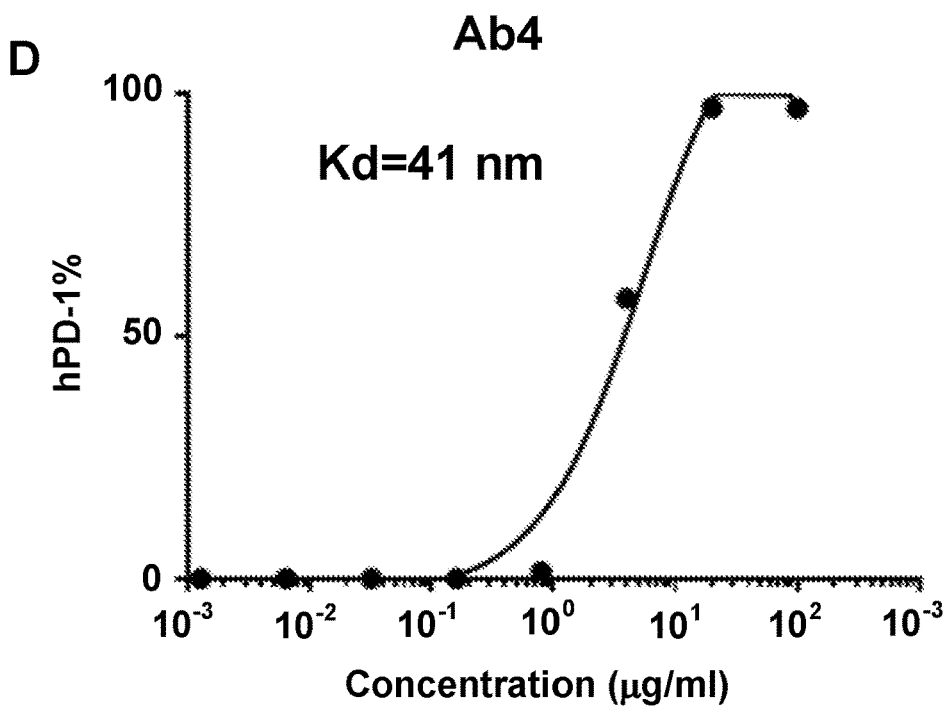
FIG. 8D shows a binding curve between Ab4 anti-PD-1 antibody and human PD-1 protein (hPD-1) on cell surface. Kd value was determined as 41 nM.
Figure 8E:
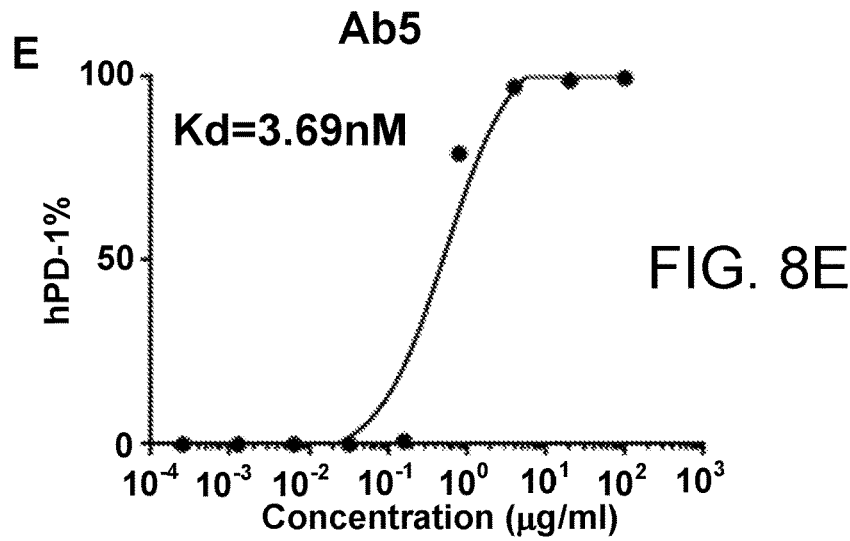
FIG. 8E shows a binding curve between Ab5 anti-PD-1 antibody and human PD-1 protein (hPD-1) on cell surface. Kd value was determined as 3.69 nM.
Figure 8F:
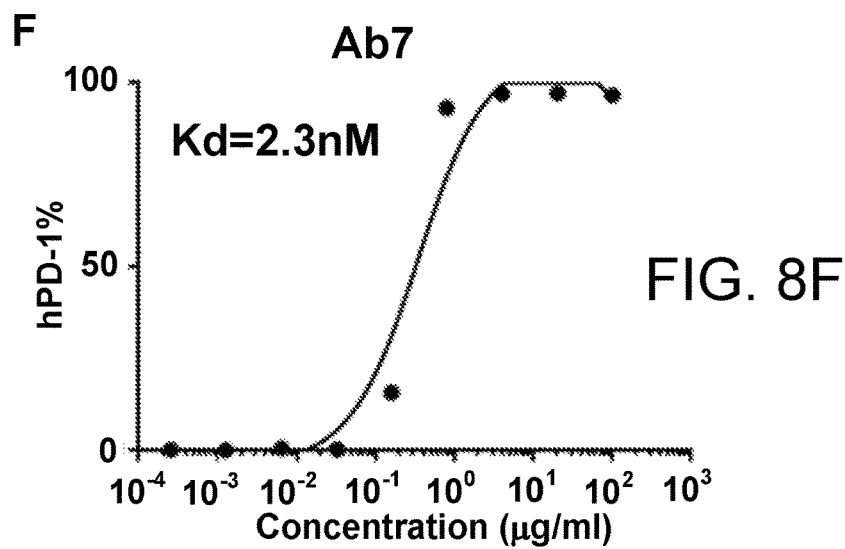
FIG. 8F shows a binding curve between Ab7 anti-PD-1 antibody and human PD-1 protein (hPD-1) on cell surface. Kd value was determined as 2.3 nM.
Figure 8G:
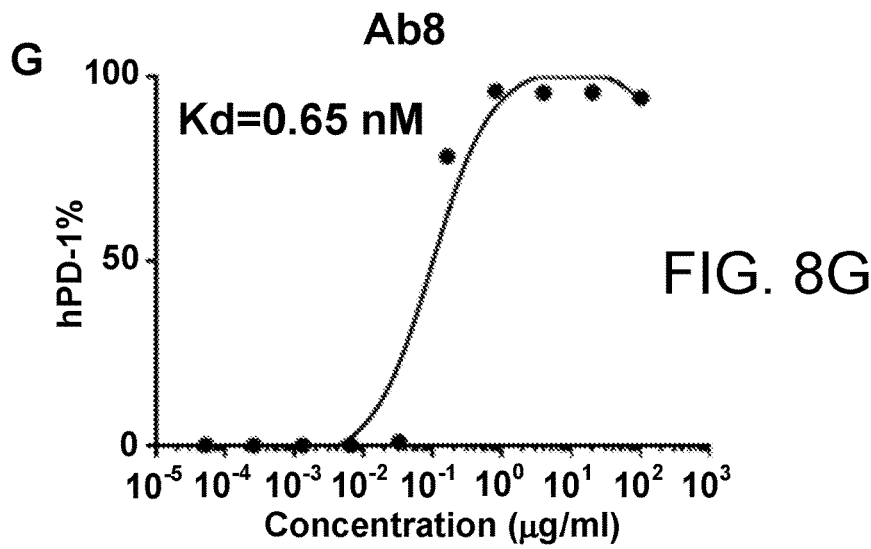
FIG. 8G shows a binding curve between Ab8 anti-PD-1 antibody and human PD-1 protein (hPD-1) on cell surface. Kd value was determined as 0.65 nM.

FIG. 6 shows flow cytometric analysis of PD-L2 (RC224141) transiently transfected HEK293T cells using anti-PD-1 antibody from hybridoma clone #11 or 1 µg/ml PD1-Fc fusion protein (TP700199) or both, and detected by anti-Fc (human) IgG-FITC (1:50). Binding of PD-L2 to PD-1 was completely blocked by anti-PD-1 antibody from hybridoma clone #11. The result shows that the anti-PD-1 antibody can effectively block the binding of PD-L2 to PD-1.

Example 3. Humanization of Antibodies

In general, antibody specific sequences (CDRs) from the mouse parent antibody were grafted onto human donor sequences. The donor sequences were selected according to bioinformatics software that utilizes extensive antibody database to calculate a unique humanness score for each combination. These antibodies were cloned into an expression vector and transfected into cells lines for recombinant protein expression. Antibody affinity to the target protein, PD-1, was tested in vitro by ELISA and cell-based binding assays.

The humanization of antibodies was achieved by CDR grafting and resurfacing strategies. Moreover, de-immunization strategy was also used. Bioinformatics tools including antibody modelling and critical framework residues identification were utilized to design humanized heavy and light chains. Those with the maximal humanization scores were combined to obtain full antibodies. Many of these antibodies will have an affinity that is comprisable to the original antibody.

The humanized VH and VL were cloned into transient expression vectors. The final constructs were confirmed by sequencing. Further, the candidate pairs (including one chimeric pair for control) of heavy and light chain were co-transfected into CHO or HEK293 cells for transient expression. The expressed antibodies were purified, followed by measurement of their epitope specificity and affinity by ELISA or cell based-binding assay.

Example 4. Binding Affinity of Anti-PD1 to Recombinant Human PD-1 (rhPD-1)

5 μg/ml of anti-PD1 antibody in 100 μl coating buffer was coated in the microwells at 4° C. overnight. By following the ELISA procedure, a 5-fold serial dilution of recombinant biotinylated human PD-1 was added to the assay plate pre-coated with anti-PD1 antibodies. The bound human PD-1 protein was then detected with Sav-HRP reagent. The results were analyzed through Prism 7 and Kd values were determined by the program.

As shown in FIGS. 7A-7G, most of the anti-PD1 antibodies could bind to the recombinant human PD-1 with a Kd value, which was determined by ELISA, at nM range. For example, the estimated Kd for h11 is 0.29 nM, the estimated Kd for Ab7 is 0.68 nM, and the estimated Kd for Ab8 is 0.32 nM. The hl 1, Ab7 and Ab8 antibodies exhibited comparable Kd values to the original mouse clone F02.

Example 5. Binding Affinity of Anti-PD1 to Human PD-1 (hPD-1) on Cell Surface 293T-PD-1 cells ($0.03 \times 10^6$/well) were incubated with different concentrations of each tested anti-PD1 antibody at 4° C. for 60 minutes. The cells were then stained with a secondary antibody (APC-anti-Hu IgG Fc for humanized antibodies and FITC-anti-Mouse IgG F(ab')2 for F02) for 30 minutes (1:50), followed by flow cytometric analysis. The results were analyzed through Prism 7 and Kd values were determined by the program.

As shown in FIGS. 8A-8G, all of the anti-PD1 antibodies can bind to the PD-1 protein expressed on the 293T-PD-1 cells. The Kd values, determined by flow cytometry, for all the antibodies were at nM range. For example, the estimated Kd for h11 is 0.55 nM, the estimated Kd for Ab2 is 3.24 nM, the estimated Kd for Ab4 is 41 nM, the estimated Kd for Ab5 is 3.69 nM, the estimated Kd for Ab7 is 2.3 nM, and the estimated Kd for Ab8 is 0.65 nM.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody or antigen-binding fragment thereof that binds to PD-1 (Programed Cell Death Protein 1) comprising:
   a heavy chain variable region (VH) comprising complementarity determining regions (CDRs) 1, 2, and 3, wherein the VH CDR1 region comprises an amino acid sequence that is identical to a selected VH CDR1 amino acid sequence, the VH CDR2 region comprises an amino acid sequence that is identical to a selected VH CDR2 amino acid sequence, and the VH CDR3 region comprises an amino acid sequence that is % identical to a selected VH CDR3 amino acid sequence; and
   a light chain variable region (VL) comprising CDRs 1, 2, and 3, wherein the VL CDR1 region comprises an amino acid sequence that is identical to a selected VL CDR1 amino acid sequence, the VL CDR2 region comprises an amino acid sequence that is identical to a selected VL CDR2 amino acid sequence, and the VL CDR3 region comprises an amino acid sequence that is identical to a selected VL CDR3 amino acid sequence,
   wherein the selected VH CDRs 1, 2, and 3 amino acid sequences and the selected VL CDRs, 1, 2, and 3 amino acid sequences are one of the following:
   (1) the selected VH CDRs 1, 2, 3 amino acid sequences are set forth in SEQ ID NOs: 8, 9, 10, respectively, and the selected VL CDRs 1, 2, 3 amino acid sequences are set forth in SEQ ID NOs: 5, 6, 7, respectively;
   (2) the selected VH CDRs 1, 2, 3 amino acid sequences are set forth in SEQ ID NOs: 22, 23, 24, respectively, and the selected VL CDRs 1, 2, 3 amino acid sequences are set forth in SEQ ID NOs: 19, 20, 21, respectively;
   (3) the selected VH CDRs 1, 2, 3 amino acid sequences are set forth in SEQ ID NOs: 74, 75, 76, respectively, and the selected VL CDRs 1, 2, 3 amino acid sequences are set forth in SEQ ID NOs: 71, 72, 73, respectively; and
   (4) the selected VH CDRs 1, 2, 3 amino acid sequences are set forth in SEQ ID NOs: 34, 35, 36, respectively, and the selected VL CDRs 1, 2, 3 amino acid sequences are set forth in SEQ ID NOs: 31, 32, 33, respectively.

2. The antibody or antigen-binding fragment thereof of claim 1, wherein the VH comprises CDRs 1, 2, 3 with the amino acid sequences set forth in SEQ ID NOs: 8, 9, and 10, respectively, and the VL comprises CDRs 1, 2, 3 with the amino acid sequences set forth in SEQ ID NOs: 5, 6, and 7, respectively.

3. The antibody or antigen-binding fragment thereof of claim 1, wherein the VH comprises CDRs 1, 2, 3 with the amino acid sequences set forth in SEQ ID NOs: 22, 23, and 24, respectively, and the VL comprises CDRs 1, 2, 3 with the amino acid sequences set forth in SEQ ID NOs: 19, 20, and 21, respectively.

4. The antibody or antigen-binding fragment thereof of claim 1, wherein the VH comprises CDRs 1, 2, 3 with the amino acid sequences set forth in SEQ ID NOs: 74, 75, and 76, respectively, and the VL comprises CDRs 1, 2, 3 with the amino acid sequences set forth in SEQ ID NOs: 71, 72, and 73, respectively.

5. The antibody or antigen-binding fragment thereof of claim 1, wherein the VH comprises CDRs 1, 2, 3 with the amino acid sequences set forth in SEQ ID NOs: 34, 35, and 36, respectively, and the VL comprises CDRs 1, 2, 3 with the amino acid sequences set forth in SEQ ID NOs: 31, 32, and 33, respectively.

6. The antibody or antigen-binding fragment thereof of claim 1, wherein the antibody or antigen-binding fragment specifically binds to human PD-1.

7. The antibody or antigen-binding fragment thereof of claim 1, wherein the antibody or antigen-binding fragment is a humanized antibody or antigen-binding fragment thereof.

8. The antibody or antigen-binding fragment thereof of claim 1,
   wherein the antibody or antigen-binding fragment is a single-chain variable fragment (scFv) or a multi-specific antibody.

9. A nucleic acid comprising a polynucleotide encoding a polypeptide comprising:
   (1) an immunoglobulin heavy chain or a fragment thereof comprising a heavy chain variable region (VH) comprising complementarity determining regions (CDRs) 1, 2, and 3 comprising the amino acid sequences set forth in SEQ ID NOs: 8, 9, and 10, respectively, and wherein the VH, when paired with a light chain variable region (VL) comprising the amino acid sequence set forth in SEQ ID NO: 2 binds to PD-1;
   (2) an immunoglobulin light chain or a fragment thereof comprising a VL comprising CDRs 1, 2, and 3 comprising the amino acid sequences set forth in SEQ ID NOs: 5, 6, and 7, respectively, and wherein the VL, when paired with a VH comprising the amino acid sequence set forth in SEQ ID NO: 4 binds to PD-1;
   (3) an immunoglobulin heavy chain or a fragment thereof comprising a heavy chain variable region (VH) comprising CDRs 1, 2, and 3 comprising the amino acid sequences set forth in SEQ ID NOs: 22, 23, and 24, respectively, and wherein the VH, when paired with a light chain variable region (VL) comprising the amino acid sequence set forth in SEQ ID NO: 16 binds to PD-1;
   (4) an immunoglobulin light chain or a fragment thereof comprising a VL comprising CDRs 1, 2, and 3 comprising the amino acid sequences set forth in SEQ ID NOs: 19, 20, and 21, respectively, and wherein the VL, when paired with a VH comprising the amino acid sequence set forth in SEQ ID NO: 18 binds to PD-1;

(5) an immunoglobulin heavy chain or a fragment thereof comprising a heavy chain variable region (VH) comprising CDRs 1, 2, and 3 comprising the amino acid sequences set forth in SEQ ID NOs: 74, 75, and 76, respectively, and wherein the VH, when paired with a light chain variable region (VL) comprising the amino acid sequence set forth in SEQ ID NO: 68 binds to PD-1;

(6) an immunoglobulin light chain or a fragment thereof comprising a VL comprising CDRs 1, 2, and 3 comprising the amino acid sequences set forth in SEQ ID NOs: 71, 72, and 73, respectively, and wherein the VL, when paired with a VH comprising the amino acid sequence set forth in SEQ ID NO: 70 binds to PD-1;

(7) an immunoglobulin heavy chain or a fragment thereof comprising a VH comprising CDRs 1, 2, and 3 comprising the amino acid sequences set forth in SEQ ID NOs: 34, 35, and 36, respectively, and wherein the VH, when paired with a VL comprising the amino acid sequence set forth in SEQ ID NO: 28 binds to PD-1;

(8) an immunoglobulin light chain or a fragment thereof comprising a VL comprising CDRs 1, 2, and 3 comprising the amino acid sequences set forth in SEQ ID NOs: 31, 32, and 33, respectively, and wherein the VL, when paired with a VH comprising the amino acid sequence set forth in SEQ ID NO: 30 binds to PD-1;

(9) an immunoglobulin heavy chain or a fragment thereof comprising a VH comprising CDRs 1, 2, and 3 comprising the amino acid sequences set forth in SEQ ID NOs: 54, 55, and 56, respectively, and wherein the VH, when paired with a VL comprising the amino acid sequence set forth in SEQ ID NO: 48 binds to PD-1;

(10) an immunoglobulin light chain or a fragment thereof comprising a VL comprising CDRs 1, 2, and 3 comprising the amino acid sequences set forth in SEQ ID NOs: 51, 52, and 53, respectively, and wherein the VL, when paired with a VH comprising the amino acid sequence set forth in SEQ ID NO: 50 binds to PD-1;

(11) an immunoglobulin heavy chain or a fragment thereof comprising a VH comprising CDRs 1, 2, and 3 comprising the amino acid sequences set forth in SEQ ID NOs: 64, 65, and 66, respectively, and wherein the VH, when paired with a VL comprising the amino acid sequence set forth in SEQ ID NO: 58 binds to PD-1;

(12) an immunoglobulin light chain or a fragment thereof comprising a VL comprising CDRs 1, 2, and 3 comprising the amino acid sequences set forth in SEQ ID NOs: 61, 62, and 63, respectively, and wherein the VL, when paired with a VH comprising the amino acid sequence set forth in SEQ ID NO: 60 binds to PD-1;

(13) an immunoglobulin heavy chain or a fragment thereof comprising a VH comprising CDRs 1, 2, and 3 comprising the amino acid sequences set forth in SEQ ID NOs: 44, 45, and 46, respectively, and wherein the VH, when paired with a VL comprising the amino acid sequence set forth in SEQ ID NO: 38 binds to PD-1; or

(14) an immunoglobulin light chain or a fragment thereof comprising a VL comprising CDRs 1, 2, and 3 comprising the amino acid sequences set forth in SEQ ID NOs: 41, 42, and 43, respectively, and wherein the VL, when paired with a VH comprising the amino acid sequence set forth in SEQ ID NO: 40 binds to PD-1.

10. A vector comprising one or more of the nucleic acids of claim 9.

11. A cell comprising one or more of the nucleic acids of claim 9.

12. A method of producing an antibody or an antigen-binding fragment thereof, the method comprising
culturing the cell of claim 11 under conditions sufficient for the cell to produce the antibody or the antigen-binding fragment.

13. An antibody or antigen-binding fragment thereof that binds to PD-1 comprising a heavy chain variable region (VH) comprising SEQ ID NO: 4, 18, 30, 40, 50, 60, or 70, and a light chain variable region (VL) comprising SEQ ID NO: 2, 16, 28, 38, 48, 58 or 68.

14. The antibody or antigen-binding fragment thereof of claim 13, wherein the VH comprises the sequence of SEQ ID NO: 4 and the VL comprises the sequence of SEQ ID NO: 2.

15. The antibody or antigen-binding fragment thereof of claim 13, wherein the VH comprises the sequence of SEQ ID NO: 18 and the VL comprises the sequence of SEQ ID NO: 16.

16. The antibody or antigen-binding fragment thereof of claim 13, wherein the VH comprises the sequence of SEQ ID NO: 70 and the VL comprises the sequence of SEQ ID NO: 68.

17. The antibody or antigen-binding fragment thereof of claim 13, wherein the VH comprises the sequence of SEQ ID NO: 30 and the VL comprises the sequence of SEQ ID NO: 28.

18. The antibody or antigen-binding fragment thereof of claim 13, wherein the VH comprises the sequence of SEQ ID NO: 50 and the VL comprises the sequence of SEQ ID NO: 48.

19. The antibody or antigen-binding fragment thereof of claim 13, wherein the VH comprises the sequence of SEQ ID NO: 60 and the VL comprises the sequence of SEQ ID NO: 58.

20. The antibody or antigen-binding fragment thereof of claim 13, wherein the VH comprises the sequence of SEQ ID NO: 40 and the VL comprises the sequence of SEQ ID NO: 38.

21. An antibody or antigen-binding fragment thereof comprising VH CDRs 1, 2, 3, and VL CDRs 1, 2, 3 of an antibody or antigen-binding fragment thereof comprising a heavy chain variable region (VH) comprising SEQ ID NO: 4, 18, 30, 40, 50, 60, or 70, and a light chain variable region (VL) comprising SEQ ID NO: 2, 16, 28, 38, 48, 58 or 68.

22. An antibody-drug conjugate comprising the antibody or antigen-binding fragment thereof of claim 1 covalently bound to a therapeutic agent.

23. A method of treating a subject having cancer, the method comprising administering a therapeutically effective amount of a composition comprising the antibody or antigen-binding fragment thereof of claim 1, to the subject.

24. The method of claim 23, wherein the subject has a solid tumor, a hematologic cancer, lymphoma, melanoma, non-small cell lung cancer, head and neck squamous cell carcinoma, relapsed or refractory classical Hodgkin lymphoma, squamous cell lung cancer, renal cell carcinoma, cutaneous squamous cell carcinoma, urothelial carcinoma, merkel-cell carcinoma, or mesothelioma.

25. A method of decreasing the rate of tumor growth, the method comprising
contacting an immune cell with an effective amount of a composition comprising an antibody or antigen-binding fragment thereof of claim 1, to the subject.

26. A method of killing a tumor cell, the method comprising contacting an immune cell with an effective amount of a composition comprising the antibody or antigen-binding fragment thereof of claim 1, to the subject.

27. A method of treating or reducing the risk of developing an infectious disease, the method comprising administering a therapeutically effective amount of a composition comprising the antibody or antigen-binding fragment thereof of claim 1, to the subject.

28. A pharmaceutical composition comprising the antibody or antigen-binding fragment thereof of claim 1, and a pharmaceutically acceptable carrier.

* * * * *

UNITED STATES PATENT AND TRADEMARK OFFICE
CERTIFICATE OF CORRECTION

PATENT NO. : 12,404,331 B2
APPLICATION NO. : 17/604555
DATED : September 2, 2025
INVENTOR(S) : Wei-Wu He et al.

It is certified that error appears in the above-identified patent and that said Letters Patent is hereby corrected as shown below:

In the Claims

Column 99, Approximately Line 16, in Claim 1, delete "(Programed Cell Death Protein 1) comprising:" and insert the same on Column 99, Line 15, as a continuation of the same subpoint.

Column 99, Line 25, in Claim 1, after "is" delete "%".

Column 99, Line 36, in Claim 1, delete "CDRs," and insert -- CDRs --.

Signed and Sealed this
Fourteenth Day of October, 2025

John A. Squires
*Director of the United States Patent and Trademark Office*